(12) United States Patent
Bazoberry et al.

(10) Patent No.: US 12,214,126 B2
(45) Date of Patent: Feb. 4, 2025

(54) AUTOMATIC SYSTEM FOR THE CONSERVATION OF GAS AND OTHER SUBSTANCES

(71) Applicant: Boston Wine Devices, LLC, Chestnut Hill, MA (US)

(72) Inventors: Carlos Fernando Bazoberry, Chestnut Hill, MA (US); Brent H. Young, Boston, MA (US)

(73) Assignee: OXFO Corporation, Chestnut Hill, MA (US)

( * ) Notice: Subject to any disclaimer, the term of this patent is extended or adjusted under 35 U.S.C. 154(b) by 939 days.

(21) Appl. No.: 17/068,718

(22) Filed: Oct. 12, 2020

(65) Prior Publication Data

US 2021/0093813 A1 Apr. 1, 2021

Related U.S. Application Data

(63) Continuation-in-part of application No. 16/358,666, filed on Mar. 19, 2019, now Pat. No. 10,800,589.

(Continued)

(51) Int. Cl.
*A61M 16/00* (2006.01)
*A61M 16/20* (2006.01)
(Continued)

(52) U.S. Cl.
CPC .... *A61M 16/0078* (2013.01); *A61M 16/0003* (2014.02); *A61M 16/202* (2014.02);
(Continued)

(58) Field of Classification Search
CPC .......... A61M 16/0078; A61M 16/0081; A61M 16/0084; A61M 16/0075; A61M 15/0086;
(Continued)

(56) References Cited

U.S. PATENT DOCUMENTS

| 718,163 | A | | 1/1903 | Sherrard | |
|---|---|---|---|---|---|
| 2,591,120 | A | * | 4/1952 | Blease | ................ A61M 16/021 128/205.15 |

(Continued)

FOREIGN PATENT DOCUMENTS

| EP | 2727993 | A1 | 4/2014 |
|---|---|---|---|
| FR | 2756347 | | 5/1998 |

(Continued)

*Primary Examiner* — Bradley H Philips
*Assistant Examiner* — Savannah L Gabriel
(74) *Attorney, Agent, or Firm* — Thomas P. O'Connell; O'Connell Law Firm

(57) ABSTRACT

A system for conserving oxygen and other gasses supplied to a recipient. A supply conduit supplies gas from a source to a reservoir, which retains a volume of gas at ambient pressure. A conduit supplies gas from the reservoir to the recipient, and an inflation detection system detects when the reservoir is below a state of inflation and when the reservoir is inflated to the state of inflation. A valve system prevents gas from flowing from the source and into the reservoir when the reservoir is at the predetermined state of inflation, and the valve system permits gas to flow from the source and into the reservoir when the reservoir is below the predetermined state of inflation whereby gas within the reservoir can be continually replenished without pressurization above ambient pressure. The inflation detection system can be an electro-mechanical system. Alternatively, the inflation detection system can be a contactless system.

33 Claims, 60 Drawing Sheets

Related U.S. Application Data

(60) Provisional application No. 63/056,944, filed on Jul. 27, 2020.

(51) Int. Cl.
*A23L 3/3409* (2006.01)
*C12H 1/12* (2006.01)

(52) U.S. Cl.
CPC .......... *A61M 16/208* (2013.01); *A23L 3/3409* (2013.01); *A23V 2002/00* (2013.01); *A61M 2016/0024* (2013.01); *A61M 2202/0208* (2013.01); *A61M 2205/3341* (2013.01); *C12H 1/12* (2013.01)

(58) Field of Classification Search
CPC .. A61M 2205/3382; A61M 2205/3386; A61M 2205/3389; F17C 2201/018
See application file for complete search history.

(56) References Cited

U.S. PATENT DOCUMENTS

| | | |
|---|---|---|
| 3,343,701 A | 9/1967 | Mahoney |
| 3,883,043 A | 5/1975 | Lane |
| 4,101,747 A | 7/1978 | Houk |
| 4,197,843 A * | 4/1980 | Bird .................... A61M 16/00 128/203.14 |
| 4,392,578 A | 7/1983 | Fipp et al. |
| 4,473,174 A | 9/1984 | Heuser |
| 4,477,477 A | 10/1984 | Arter |
| 4,595,121 A | 6/1986 | Schultz |
| 4,684,033 A | 8/1987 | Marcus |
| 4,702,396 A | 10/1987 | Gwiazda |
| 4,756,436 A | 7/1988 | Morita et al. |
| 4,838,442 A | 6/1989 | Merry |
| 4,856,680 A | 8/1989 | Sitton |
| 4,984,711 A | 1/1991 | Ellis |
| 5,049,106 A | 9/1991 | Kim et al. |
| 5,139,179 A | 8/1992 | Cecil |
| 5,240,853 A | 8/1993 | Copeland et al. |
| 5,398,675 A * | 3/1995 | Henkin ............ A61M 16/0081 128/205.15 |
| 5,458,165 A | 10/1995 | Liebmann, Jr. |
| 5,566,730 A | 10/1996 | Liebmann, Jr. |
| 5,662,099 A * | 9/1997 | Tobia .................... A61M 16/01 128/205.15 |
| 5,667,110 A | 9/1997 | McCann et al. |
| 6,364,161 B1 | 4/2002 | Pryor |
| 6,607,100 B2 | 8/2003 | Phelps et al. |
| 6,991,136 B2 | 1/2006 | de la Guardia |
| 7,051,901 B2 | 5/2006 | Hickert |
| 7,096,677 B2 | 8/2006 | Luzaich et al. |
| 7,232,354 B2 | 6/2007 | Olson et al. |
| 7,370,651 B2 | 5/2008 | Holder |
| 7,395,949 B2 | 7/2008 | Ehret et al. |
| 7,588,032 B2 | 9/2009 | Cannon |
| 7,712,637 B2 | 5/2010 | Lambrecht |
| 8,033,431 B2 | 10/2011 | Sommerfield et al. |
| 8,141,746 B2 | 3/2012 | Lambrecht |
| 8,225,959 B2 | 7/2012 | Lambrecht |
| 8,490,832 B2 | 7/2013 | Lambrecht |
| 8,640,919 B2 | 2/2014 | Lambrecht |
| 8,746,502 B2 | 6/2014 | Lambrecht |
| 9,061,878 B2 | 6/2015 | Lambrecht |
| 9,139,412 B2 | 9/2015 | Lambrecht |
| 9,181,021 B2 | 11/2015 | Manera |
| 10,201,674 B2 | 2/2019 | Acker et al. |
| 2006/0144225 A1* | 7/2006 | Downie ............... A61M 1/3666 95/90 |
| 2006/0157515 A1 | 7/2006 | Oswald |
| 2007/0039977 A1 | 2/2007 | Donaldson |
| 2007/0125377 A1* | 6/2007 | Heinonen ........... A61M 16/204 128/204.21 |
| 2007/0181602 A1 | 8/2007 | Taradalsky |
| 2008/0015475 A1* | 1/2008 | Lau ....................... A61M 16/12 128/205.13 |
| 2008/0170963 A1 | 7/2008 | Cantrell |
| 2008/0272085 A1 | 11/2008 | Laporta |
| 2009/0095776 A1 | 4/2009 | Turner et al. |
| 2009/0218365 A1 | 9/2009 | Taradalsky et al. |
| 2009/0224000 A1 | 9/2009 | Lopez et al. |
| 2010/0012612 A1 | 1/2010 | Miyanaga |
| 2011/0204093 A1 | 8/2011 | Lee |
| 2012/0214371 A1 | 8/2012 | Pisor |
| 2013/0153685 A1 | 6/2013 | Drobot et al. |
| 2014/0012150 A1* | 1/2014 | Milne ................ A61M 16/0051 600/529 |
| 2014/0158557 A1 | 6/2014 | Dolan et al. |
| 2014/0220463 A1 | 8/2014 | Daniel |
| 2014/0224833 A1 | 8/2014 | Lambrecht |
| 2014/0312059 A1 | 10/2014 | Dziuk et al. |
| 2015/0011953 A1* | 1/2015 | Schmidt .................. A61M 1/73 604/318 |
| 2016/0193438 A1 | 7/2016 | White et al. |
| 2018/0008790 A1* | 1/2018 | Costella ............. A61B 5/0876 |
| 2018/0330565 A1 | 11/2018 | Koretz et al. |
| 2020/0268994 A1* | 8/2020 | Boulanger .......... A61M 16/203 |

FOREIGN PATENT DOCUMENTS

| | | |
|---|---|---|
| JP | 2006327683 A | 12/2006 |
| JP | 2007169113 A | 7/2007 |
| KR | 10-2012-0002672 | 1/2012 |
| WO | WO200104718 | 1/2001 |

* cited by examiner

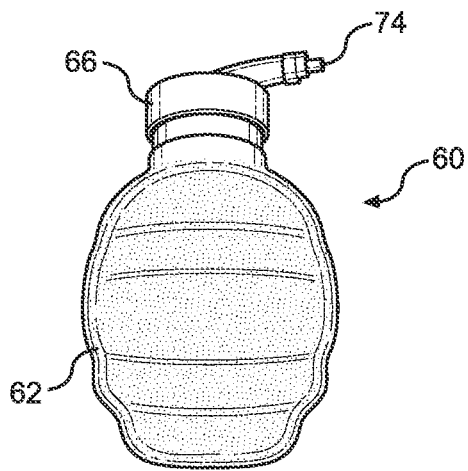
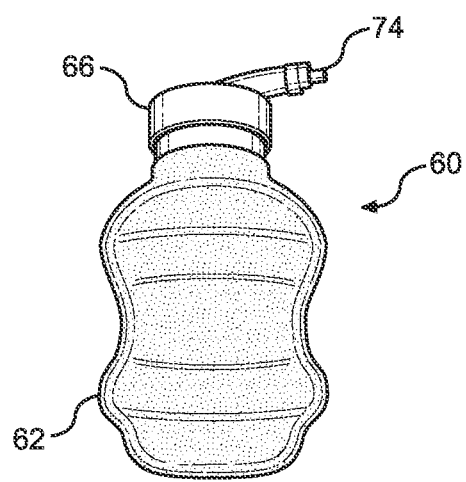
FIG. 20A  FIG. 20B
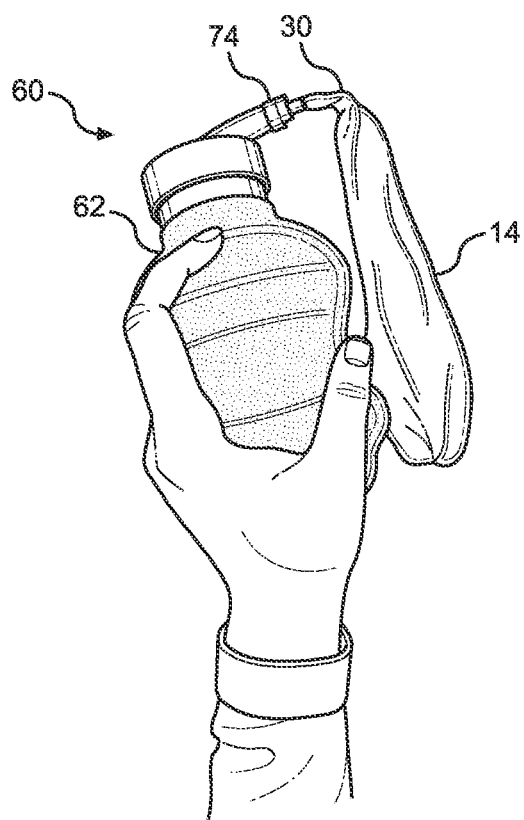
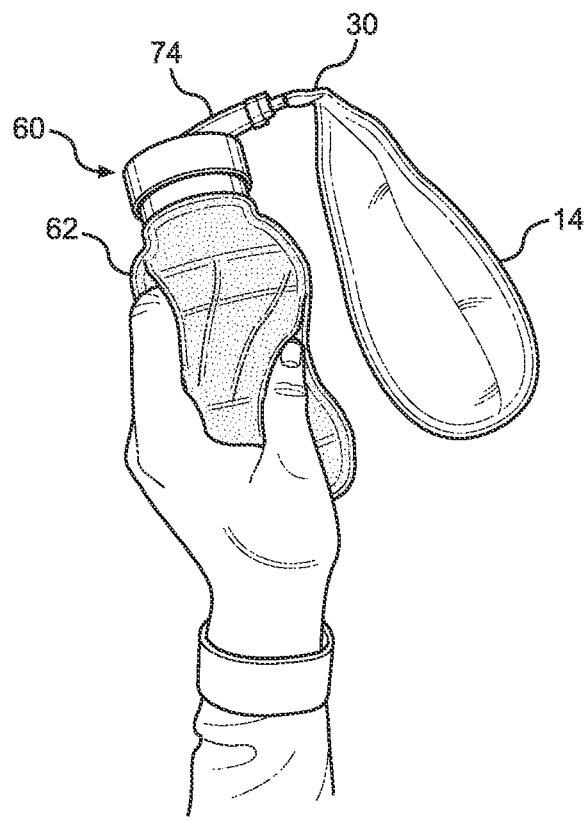
FIG. 20C  FIG. 20D

AUTOMATIC SYSTEM FOR THE CONSERVATION OF GAS AND OTHER SUBSTANCES

RELATED APPLICATIONS

This application is a Continuation-in-Part of application Ser. No. 16/358,666, filed Mar. 19, 2019, which was a continuation-in-part of application Ser. No. 15/057,117, filed Feb. 29, 2016, which was a continuation-in-part of application Ser. No. 14/211,137, filed Mar. 14, 2014, which claimed priority to Provisional Application No. 61/781,477, filed Mar. 14, 2013, and this application claims priority to Provisional Patent Application No. 63/056,944, filed Jul. 27, 2020. The entirety of each of the foregoing is incorporated herein by reference.

FIELD OF THE INVENTION

The present invention relates generally to the delivery of gases from a source to a recipient. More particularly, disclosed herein are a system and method for conserving gases and other substances when delivering them from a donor reservoir to a recipient by volumetric displacement at ambient pressure with automatic refilling of the donor reservoir from a source. In embodiments of the system and method, gases or other substances are transferred from a donor reservoir to a recipient on demand by the recipient via a pressure difference between them with automatic refilling of the donor reservoir with gas at ambient pressure.

BACKGROUND OF THE INVENTION

The supply of oxygen can be a critical need for hospital patients and others. Meanwhile, in developing countries and during times of increased demand in all places, shortages of oxygen and excessive costs can place extreme limits on availability and can jeopardize the health and safety of patients in need. For instance, during the COVID-19 pandemic that is ongoing during the writing of this document, the demand for oxygen has left hospitals and other caregiving institutions in dire need of the life-saving gas. One headline from the AP News network on Jun. 24, 2020 warned, "Scarce Medical Oxygen Worldwide Leaves Many Gasping for Life." One day later, Reuters observed, "WHO Warns of Oxygen Shortage as COVID Cases Set to Top 10 Mln" with the World Health Organization estimating based on there being approximately one million new coronavirus cases worldwide per week that the world will need 620,000 cubic meters of oxygen per day, which roughly equals 88,000 large cylinders, for COVID-19 patients alone.

One way that supplemental oxygen is supplied to patients is via a fluidic connection, typically extension tubing, between a pressurized source of oxygen, such as an oxygen cylinder or tank, and the patient. The pressurized source supplies a constant flow of oxygen to the patient as it travels from the tank continuously through the connector tubing, regardless of whether the patient is breathing in or out. As a result, even while the patient exhales and thus cannot intake oxygen, the oxygen constantly flows and is wasted. Indeed, half or even more of the constantly supplied oxygen in this continuous pressure feed method is wasted and expelled to the atmosphere.

It is thus apparent that conserving oxygen resources with one patient may well save the life of another. Moreover, conserving oxygen will not only reduce the overall need per patient but will also tend to reduce the cost of oxygen per unit. Meanwhile, each patient requires a sufficient supply of oxygen. The challenge is thus how to provide oxygen in sufficient supply on demand while minimizing waste.

To comprehend a solution to that challenge, one must understand what drives the flow of air containing oxygen into the lungs, how flow is normally initiated and maintained between the patient and ambient air, and how alveolar pressure varies while pleural pressure decreases throughout inspiration. Air, like other fluids, moves from a region of higher pressure to a region of lower pressure. The flow of air into the lungs requires the establishment of a pressure gradient between the atmosphere and the alveoli. This driving pressure gradient is accomplished by the contraction of the inspiratory muscles. Contraction of the inspiratory muscles expands the chest wall, lowering the pressures in the thoracic cavity so that intra-pleural and alveolar pressure decrease according to Boyle's law. Muscle contraction results in a change in thoracic volume, leading to a change in alveolar pressure, which in turn provides the driving pressure for air flow into the lungs.

Normally, the lungs absorb oxygen from the air during breathing. However, certain conditions can prevent a person from getting enough oxygen. As a result, oxygen therapy with oxygen delivery equipment is required. Patients can receive oxygen therapy from a source of oxygen through tubes resting in their nose, through a facemask, or through a tube placed in their trachea or windpipe. Oxygen treatment increases the amount of oxygen the lungs receive and deliver to the blood. Oxygen therapy may be prescribed for a patient when the patient has a condition that causes the patient's blood oxygen levels to be too low. Low blood oxygen may make patients feel short of breath, tired, or confused and can damage the patient's body. Oxygen therapy may be needed on a temporary basis, such as due to a treatable respiratory illness, or on a long-term basis. Often, the source of oxygen is a tank of compressed oxygen gas or liquid.

Oxygen tanks must be produced, transported, stored, and refilled on a continual basis. In exigent circumstances, such as during an epidemic or a pandemic involving respiratory distress, need can dangerously outpace supply. Moreover, in remote and economically challenged locations, providing ample replenishment of oxygen supplies can be highly costly, even catastrophically impossible. Meanwhile, with life-saving oxygen in preciously short supply and with oxygen constantly passed through tubing to the patient, at least half of the supplied oxygen is simply exhausted into the atmosphere, including during exhalation during which the entirety of the supplied oxygen is wasted.

It is thus apparent to the present inventors that providing a system and method that provides a ready supply of oxygen to a patient while minimizing or eliminating wasted oxygen, including during the expiratory breathing phase, would minimize the need of individual patients, maximize the effective supply of oxygen, and, in so doing, enable better health outcomes in a cost-efficient manner even in times of public health crises.

With these real needs recognized by the present inventors, reference will be had to the developments of one of the current inventors as disclosed and protected by U.S. Pat. No. 9,272,834, issued Mar. 1, 2016, U.S. Pat. No. 10,233,068, issued Mar. 19, 2019, and U.S. application Ser. No. 16/358, 666, filed Mar. 19, 2019, each being incorporated herein by reference in its entirety. In a markedly different field of endeavor in those cases, plural advances were disclosed in preserving and dispensing wine and other perishable substances in relation to their vessel containers. The '834 patent and the '068 patent were directed to preserving wine and other perishable substances by volumetric displacement between a flowable substance within an inner volume of a vessel and a preservative gas to permit a dispensing of a desired volume of the substance, such as wine, from the vessel and the concomitant introduction of the preservative gas into the inner volume of the vessel to prevent degradation of a volume of flowable substance remaining in the open inner volume of the vessel. With the '666 application, a system and method were disclosed for automatically replenishing preservative gas within an inflatable bladder for supply to a vessel during a dispensing of a flowable substance from the vessel by volumetric displacement.

In these earlier disclosures, it was noted how preserving wines and other beverages and perishable substances once they have been initially exposed to air was long a problem that confronted consumers who want to utilize only a portion of the substance leaving the rest for a later occasion. Indeed, many inventors sought to provide systems and methods for preserving retained liquids and other substances against degradation by exposure to air. Unfortunately, as noted, most attempts of the prior art have failed without expensive and complicated pressurized systems.

For instance, due to its chemical composition, wine is susceptible to degradation by an increase in acidity and spoiling when it is exposed to a significant amount of undesired oxygen. Indeed, to the experienced palate, oxygen typically produces a negative impact on the taste of wine within hours of oxygen exposure.

Some preservation methods of the prior art are relatively simple. For instance, many sought to limit a wine's exposure to the oxygen content in ambient air by merely re-corking an opened wine bottle and placing the bottle in a cool place or refrigerating the corked container. Although not overly difficult, such methods are of extremely limited effectiveness and reliability.

Other methods involved adding matter to the inner volume of the vessel to replace the volume of dispensed wine. Solids, liquids, and gases have been inserted into the open inner volumes of wine bottles and other vessels seeking to displace oxygen-rich air from the vessel to limit the amount of oxygen that is in the bottle available to interact with and deteriorate the wine. Some such methods involved inserting stones, glass beads, and other solid objects into the vessel. Others seek to displace or prevent the introduction of ambient air into the vessel by injecting oils or inert gases into the inner volume of the vessel. Still other inventors sought to confront degradation by filling a bladder inserted into the open inner volume and inflating the bladder to fill the inner volume as the liquid exits the vessel. Each such method and system disadvantageously tends to introduce undesirable contaminants, such as dirt, oil, bacteria, fungi, and other contaminants, to the inner volume of the vessel. The introduction of such contaminants runs directly counter to the goal of preserving the integrity of the contained wine or other substance and can itself contribute to spoilage while also representing a hazard to the health of the consumer.

One system involving an expandable bladder is disclosed in the Sep. 26, 1967 U.S. Pat. No. 3,343,701 to Mahoney for a Sealing and Exhausting Device for Containers. There, Mahoney teaches a system where a replacement stopper is inserted into a vessel. An expansible bulb is retained by a tube that passes through the stopper, and an exhaust tube passes through the stopper to permit the passage of air from the inner volume of the vessel as the bulb is expanded. Even beyond the undesirable insertion of a foreign object into what may be a very valuable bottle of wine, for instance, the system taught by Mahoney and many similar systems of the prior art still leave at some unadulterated, high-oxygen air in the vessel. Moreover, an unintentional depressurization of the bulb, such as by leaking or another malfunction, will leave the contents of the vessel fully exposed to ambient air and consequent degradation.

Further inflatable bladder systems are taught, for instance, in U.S. Pat. No. 4,392,578 to Fipp et al. and in U.S. Pat. No. 7,051,901 to Hickert. Fipp et al. teach a system similar to that disclosed by Mahoney where a stopper plug retains an expansible bladder, and a venting valve permits air within a bottle to be exhausted. A pump is provided to inflate the bladder. Fipp et al. go further than Mahoney by providing an inert gas reservoir for dispensing an inert gas into the vessel prior to the inflation of the bladder so that a protective layer is formed atop the retained liquid. In Hickert, air can be forced into an expansible bladder by a hand pump to cause the level of wine in the bottle to rise to contact the stopper. Again, however, the systems and methods of Fipp et al. and Hickert entail the insertion of a foreign bladder into direct contact with the vessel's contents, and the performance of the system hinges largely on the bladder's resistance to deflating.

Yet another system seeking to preserve the perishable contents of a bottle through an expansible bladder within the bottle is disclosed in U.S. Pat. No. 7,395,949 to Ehret et al. Here, the filling of the bladder is sought to be achieved by volumetric displacement where a pressure differential created when wine or other liquid is exhausted through a borehole in a stopper tends to draw ambient air into a second borehole in the stopper to inflate an expandable volumetric displacement balloon disposed within the inner volume of the bottle. Still, one must expose the contents of the vessel to the inserted balloon, which is designed to be used repeatedly. Furthermore, operation of the Ehret et al. system hinges on an ability to inflate the balloon and the balloon's continued ability to stay inflated even when unattended.

Other methods of the prior art involve evacuating air from the inner volume of the wine bottle or other vessel thereby to attempt to create and maintain a vacuum. Under such methods, a minimized amount of oxygen is left in the vessel so that, ideally, degradation of the vessel's contents is correspondingly minimized. However, inducing and maintaining a sufficient vacuum has typically proven challenging. Furthermore, an indication of when adequate vacuum pressure has been achieved or lost is normally nonexistent. Consequently, a user cannot be confident that the contents of the vessel are being preserved even when the process is initiated. Even if a proper vacuum is initially created, the vessel's contents can spoil during the very time that the user believes they are being protected.

It was further recognized that systems were known where an inflatable bladder is avoided by the direct injection of an inert gas under pressure into the inner volume of the vessel. Such systems can simultaneously achieve a dispensing of the liquid contents of the vessel and an insertion of the preservative gas as the pressurized gas displaces the liquid through an exhaust port. Some of these types of systems involve piercing the original cork with a trocar or other piercing device to create one or more fluid pathways between the inner volume of the vessel and the environment. One example of such a system is set forth in U.S. Pat. No. 4,984,711 to Ellis. There, a hollow screw with first and second passageways is driven through the cork. Gas under pressure is injected from a canister through one passageway, and liquid is discharged through the second passageway. This and similar approaches can be challenging and expensive to implement and maintain such that they are outside the budget of many individual consumers. Indeed, users are often left to guess whether they have injected a sufficient volume of the inert gas. Where too little gas is injected, the wine or other substance is inadequately protected. Consequently, many users are tempted to inject an extra burst of gas, which is wasteful and dangerous. Where too much gas is injected, excess pressure can accumulate in the bottle leading to leakage or even a dangerous bursting of the bottle. Furthermore, the gas canisters used in such systems are typically disposable, which contributes to environmental waste.

The prior art also discloses systems where an entire bottle or multiple bottles are maintained in a container that can be filled with preservative gas. An example of such a system is shown and described in U.S. Pat. No. 4,856,680 to Sitton. Under the teachings of the '680 patent, a chamber is provided to receive an opened bottle, and pressurized inert gas is introduced to preserve the contents of the bottle and, when sufficiently pressurized, to dispense liquid from the bottle through a fluid dispensing conduit. Properly maintained, such systems do insulate the contents of the bottle from excess exposure to oxygen-rich ambient air, but the acquisition and maintenance costs and complexities leave the systems accessible only to restaurants and similar businesses and a limited set of individuals.

It was appreciated that, despite the many attempts of the prior art to provide devices, systems, and methods to preserve the quality of wine and other substances in an opened vessel, there remained a recognized need for a system and method for preserving wine and other perishable substances that overcame the notable disadvantages that remained. One of the present inventors recognized a need for a preservation system and method that were effective and reliable not only on initial application but also during use and storage. Further needs were recognized for a preservation system and method that was elegant and uncomplicated in application and use and for a preservation system and method that was affordable during initial manufacture, sale, and continued usage. Still further, it was appreciated that it would be advantageous to provide such a system and method that did not require the insertion of foreign objects into the inner volume of the vessel.

To these ends, one of the present inventors devised of the systems and methods for preserving wine and other perishable substances and improvements and refinements thereto that are now protected by U.S. Pat. No. 9,272,834, issued Mar. 1, 2016, and U.S. Pat. No. 10,233,068, issued Mar. 19, 2019. These patents disclose and protect systems and methods for preserving perishable substances within a vessel by volumetric displacement between a flowable substance within an inner volume of a vessel and a preservative gas to permit a dispensing of a desired volume of the substance, such as wine, from the vessel and the concomitant introduction of the preservative gas into the inner volume of the vessel to prevent degradation of a volume of flowable substance remaining in the open inner volume of the vessel.

In the '834 and '068 patents, preservative gas is supplied for the displacement process through a compressible bladder. Preservative gas is drawn from the bladder in volumetric displacement of liquid poured from the vessel under the force of gravity. As disclosed, the bladder could be refilled with preservative gas as needed. The systems and methods of the above-referenced patents provide utility and advantages over the prior art.

However, the present inventor appreciated that there are circumstances where continually refilling or replacing preservative gas within a compressible bladder can be inconvenient or where greater volumes of preservative gas may be required than can be practically retained in a bladder retaining a given volume of gas. For instance, in bars and restaurants, it may be desirable to introduce preservative gas into several bottles of wine consecutively. In these and other situations where there is a continual high demand for gas from the compressible reservoir, replenishing or replacing compressible gas in the reservoir can be impractical. There are other circumstances where the reservoir may not have an inner volume sufficient in size to supply the preservative gas needed for preservation in a larger vessel.

With application Ser. No. 16/358,666, it was disclosed that a compressible bladder could be consistently and automatically replenished with preservative gas while permitting the preservative gas to be drawn from the compressible bladder in a volumetric displacement process to preserve a substance, such as wine, within a vessel. The preservative gas within the compressible bladder was consistently replenished to provide an available supply without introducing excess pressure into the bladder that would interfere with the drawing of gas from the bladder and into the vessel under the natural force of gravity.

While the inventions of the '834 and '068 patents and the '666 application represented substantial developments in the art of preserving wines and other perishable substances, the present inventors further appreciated the critical need for a system and method capable of providing a ready supply of oxygen to a patient while minimizing or eliminating wasted oxygen thereby to minimize the needs of individual patients, to maximize the effective supply of oxygen, and to enable better patient care and optimal health outcomes in a cost-efficient manner even in times of public health crises.

SUMMARY OF THE INVENTION

Knowing the critical need for ample supplies of oxygen to patients, a primary object of the present invention is to save lives.

The present inventors further set forth with a basic object of providing a system and method for supplying oxygen and other flowable substances to patients and other recipients in need that reduces wasted oxygen thereby to maximize the effective use of available oxygen supplies.

A further object of embodiments of the invention is to provide a system and method for supplying oxygen and other flowable substances to recipients that enable an ample supply of oxygen on-demand while minimizing or eliminating inefficient oxygen losses.

Another object of manifestations of the invention is to provide a system and method for supplying oxygen and other flowable substances to recipients that maximize efficiencies in usage and minimize supply costs.

With the applications that resulted in the '834 and '068 patents, one of the current inventors set forth with the basic object of providing a system and method for preserving wine and other perishable substances that was highly effective and reliable not only on initial application but also during use and storage.

Embodiments of that preservation system and method also sought to be elegant and uncomplicated in application and use such that confident and effective application can be achieved by neophyte and expert users alike.

A related object of the inventions of the '834 and '068 patents was to provide a system and method for the preservation of substances in vessels that does not require the insertion of foreign objects, such as inflatable bladders and the like, into the inner volume of the vessel thereby to avoid the structural and hygienic disadvantages deriving therefrom.

Yet another object of the invention was to provide a preservation system and method for wines and other perishable substances that can be affordable not only during initial manufacture and sale but also during continued usage.

Manifestations of the inventions of the '666 application have the further object of enabling a compressible bladder that could be consistently and automatically replenished with preservative gas while permitting the preservative gas to be drawn from the compressible bladder in a volumetric displacement process to preserve a substance within a vessel.

In particular embodiments of the invention of the '666 application, a further object was to enable preservative gas within a compressible bladder to be consistently replenished to provide an available supply but without pressurizing the bladder reservoir or introducing excess pressure into the bladder that would interfere with the drawing of gas from the bladder and into the vessel under the natural force of gravity.

A further object of manifestations of the invention of the '666 application was to provide a preservative gas system and method wherein the volume of liquid displaced in volumetric displacement in individual and multiple vessels could be measured, tracked, stored, and communicated to enable, without limitation, inventory management, marketing, accounting, spoilage prevention, and further advantageous uses.

These and further objects, advantages, and details of the present invention and those of the '834 and '068 patents and the '666 application will become obvious not only to one who reviews the present specification and drawings but also to those who have an opportunity to experience the systems and methods disclosed herein in operation. However, it will be appreciated that, although the accomplishment of plural of the foregoing objects in a single embodiment of the invention may be possible and indeed preferred, not all embodiments will seek or need to accomplish each and every potential advantage and function. Nonetheless, all such embodiments should be considered within the scope of the present invention.

One will appreciate that the foregoing discussion broadly outlines the more important goals and features of the invention to enable a better understanding of the detailed description that follows and to instill a better appreciation of the inventors' contribution to the art. Before any particular embodiment or aspect thereof is explained in detail, it must be made clear that the following details of construction and illustrations of inventive concepts are mere examples of the many possible manifestations of the invention.

In carrying forth one or more of the foregoing objects, an embodiment of the present invention can be characterized as a system for the conservation of oxygen supplied to a patient. The system has an expandable and compressible donor reservoir that has an outer wall, an inner volume for retaining a volume of oxygen, and at least one orifice for allowing a passage of oxygen into and out of the inner volume. As disclosed herein, the donor reservoir can comprise a shell of flexible material, such as a shell of foil. A supply conduit is adapted to receive oxygen from a source of oxygen. The supply conduit has a first end for supplying oxygen to the donor reservoir and a second end for being fluidically connected to the source of oxygen, and an ambient pressure conduit is adapted to supply oxygen along a fluid path from the donor reservoir to a recipient. The ambient pressure conduit has a first end in fluidic communication with the donor reservoir, such as through a connector, for receiving oxygen from the donor reservoir and a second end for being fluidically connected to the recipient. An inflation detection system is operable to detect a first condition wherein the donor reservoir is inflated with oxygen to a predetermined state of inflation and a second condition wherein the donor reservoir is below the predetermined state of inflation. Finally, a valve system is disposed between the source of oxygen and the donor reservoir. The valve system is operative in a closed condition to prevent oxygen from flowing from the source of oxygen and into the donor reservoir when the donor reservoir is in the first condition, and the valve system is operative in an open condition to permit oxygen to flow from the source of oxygen and into the donor reservoir when the donor reservoir is in the second condition. Under this construction, oxygen can be supplied to a patient, such as through a patient breathing mask as the recipient, from the donor reservoir, and the donor reservoir can be automatically replenished to the predetermined state of inflation.

In practices of the system, the valve system and the inflation detection system are operative to maintain the volume of oxygen in the donor reservoir substantially at ambient pressure. For instance, the donor reservoir can be considered to have a fully inflated condition, and the inflation detection system can be operative to detect when the donor reservoir is inflated to within a predetermined range of the fully inflated condition. The inflation detection system can then detect the first condition when the donor reservoir is inflated to within the predetermined range of the fully inflated condition, and the inflation detection system can detect the second condition when the donor reservoir is inflated below the predetermined range of the fully inflated condition.

In certain embodiments, the inflation detection system comprises an electro-mechanical system. For instance, the inflation detection system can comprise a switch disposed to be moved by the outer wall of the donor reservoir when the donor reservoir is inflated with oxygen to the predetermined state of inflation. The switch can be biased, such as by gravity, by a resiliently compressible member, or by any other effective method, toward the donor reservoir. The switch can be considered to have an activated state wherein the switch is disposed at or beyond an inward position with respect to the inner volume of the donor reservoir and a deactivated state when the switch is moved outwardly by the outer wall of the donor reservoir when the volume of oxygen in the donor reservoir reaches the predetermined state of inflation. The valve system is operative to prevent oxygen from flowing from the source of oxygen and into the donor reservoir when the switch is in the deactivated state, and the valve system is operative to permit oxygen to flow from the source of oxygen and into the donor reservoir when the switch is in the activated state.

In particular manifestations of the system, the switch comprises a float switch. For example, the float switch can have a contact structure with a collar that is extendable and retractable relative to a central column. The collar can then retain a magnet, and the central column can then retain electrical contacts that are brought into electrical contact by a proximity of the magnet when the switch is in the activated state.

According to practices of the system, the valve system can take the form of a solenoid valve that is in electrical communication with the inflation detection system. The solenoid valve can be induced by the inflation detection system to a closed condition to prevent the flow of oxygen from the source of oxygen to the donor reservoir when the donor reservoir is in the first condition, and the solenoid valve can be induced by the inflation detection system to an open condition to permit the flow of oxygen from the source of oxygen to the donor reservoir when the donor reservoir is in the second condition.

A recipient delivery device, such as a patient breathing mask or another recipient delivery device, can be coupled to the second end of the ambient pressure conduit. Further, in certain embodiments, the donor reservoir can be disposed within a housing, which could comprise a main housing of the system, a sub-housing within a main housing, or some other type of housing. In other practices, the donor reservoir can be disposed without a housing. Where a housing is provided, the inflation detection system can comprise an electro-mechanical system with a switch supported by the housing and disposed to be moved by the outer wall of the donor reservoir when the donor reservoir is inflated with oxygen to the predetermined state of inflation. Even more particularly, the housing can be transparent such that the state of inflation of the donor reservoir can be visually perceived.

Embodiments of the system can further incorporate a one-way inspiratory valve disposed along the fluid path from the donor reservoir to the recipient. The one-way inspiratory valve can be operative to enable oxygen to flow from the donor reservoir, through the ambient pressure conduit, and to the recipient but to prevent reverse flow of oxygen.

In alternatively practices of the invention, the inflation detection system comprises a contactless detection system. For instance, the inflation detection system can take the form of an optical detection system.

While the present invention is largely described as being employed to supply oxygen to patients in a manner that conserves oxygen supply, it will be understood that the invention is not limited to retaining and dispensing oxygen. Indeed, other gasses and mixtures of gasses and other fluids are possible within the scope of the invention. To that extent, embodiments of the invention can be more broadly characterized as a system for providing a supply of gas. Moreover, the gas need not necessarily be supplied to a patient. Other recipients are contemplated and within the scope of the invention except as may be expressly excluded by the claims.

With respect to the disclosed invention for a volumetric displacement preservation system, one potential embodiment seeks to preserve a volume of flowable substance, such as a wine, in an open inner volume of a vessel, such as a wine bottle. The volumetric displacement preservation system can include a fluid exchange structure with a stopper for creating a sealing engagement with the vessel. A fluid exhaust pathway is disposed in the fluid exchange structure with a first end in fluidic communication with the open inner volume of the vessel and a second end in fluidic communication exterior to the vessel. The fluid exhaust pathway has an open condition where fluid can pass through the fluid exhaust pathway and a closed condition where fluid substantially cannot pass through the fluid exhaust pathway. A fluid inlet pathway is disposed in the fluid exchange structure with a first end in fluidic communication with the open inner volume of the vessel and a second end in fluidic communication exterior to the vessel. The fluid inlet pathway has an open condition where fluid can pass through the fluid inlet pathway and a closed condition where fluid substantially cannot pass through the fluid inlet pathway. A chamber, such as a flexible and compressible bladder, has an inner volume for retaining a volume of preservative gas and an orifice for dispensing the preservative gas from the chamber. A fluidic connection is provided for fluidically connecting the orifice of the chamber to the second end of the fluid inlet pathway with the chamber retained external to the vessel.

Under this construction, when the fluid exhaust pathway and the fluid inlet pathway are in closed conditions, fluid cannot be exhausted through the fluid exhaust pathway and fluid cannot be received through the fluid inlet pathway. However, when the fluid exhaust pathway and the fluid inlet pathway are in open positions, liquid can be dispensed from the open inner volume of the vessel through the fluid exhaust pathway and preservative gas can be drawn from the chamber and into the open inner volume of the vessel through the fluid inlet pathway in volumetric displacement of the liquid exhausted through the fluid exhaust pathway. Consequently, the open inner volume of the vessel can be progressively filled by preservative gas to prevent or minimize the degradation of the remaining contents of the vessel.

In embodiments of the system, the fluidic connection for fluidically connecting the orifice of the chamber to the second end of the fluidic inlet pathway can take the form of a valve connector sealingly engaged with the orifice of the chamber and a valve connector sealingly engaged with the second end of the fluid inlet pathway. The valve connector sealingly engaged with the orifice of the chamber can have a closed condition when not engaged with another valve connector.

It is also contemplated that the fluid exchange structure can have a fluid exchange valve with a first condition where the fluid exhaust pathway and the fluid inlet pathway are substantially closed and a second condition where the fluid exhaust pathway and the fluid inlet pathway are open. To carry this forth in one example, the fluid exchange valve, which can be pivotable between the first and second conditions, can have a conduit joining portion that completes and opens the fluid exhaust pathway when the fluid exchange valve is in the second condition and a separate conduit joining portion that completes and opens the fluid inlet pathway when the fluid exchange valve is in the second condition. Moreover, the fluid exchange valve can include a portion that substantially seals the fluid exhaust pathway when the fluid exchange valve is in the first condition and a portion that substantially seals the fluid inlet pathway when the fluid exchange valve is in the first condition. Manifestations of the invention can have a fluid exchange structure with a head portion that retains the stopper, and the fluid exchange valve can have a base portion that is pivotable in relation to the head portion between the first and second conditions.

Embodiments of the system can have a fluid exchange valve with first and second conduit joining portions that cooperate to complete and open the fluid exhaust pathway when the fluid exchange valve is in the second condition. Those first and second conduit joining portions can meet within the fluid exchange valve distal to the first and second conduit joining portions such that wine or another substance exhausted through the fluid exhaust pathway can pass through the first and second conduit joining portions and mix prior to exhaustion from the fluid exchange valve, such as through a nozzle of the fluid exchange valve that is disposed distal to the first and second conduit joining portions.

Particular embodiments of the system can have the conduit joining portion that completes and opens the fluid inlet pathway when the fluid exchange valve is in the second condition take the form of a channel in the base portion of the fluid exchange valve, and that channel can complete the fluid inlet pathway when the fluid exchange valve is in the second condition. In such embodiments, first and second conduit joining portions in the base portion can again cooperate to complete and open the fluid exhaust pathway when the fluid exchange valve is in the second condition, and the conduit joining portion that completes and opens the fluidic inlet pathway can be disposed at least partially between the first and second conduit joining portions that cooperate to complete and open the fluid exhaust pathway.

Manifestations of the system can have a head portion of the fluid exchange structure with a pathway corresponding in shape and size to a shape and size of the base portion of the fluid exchange valve, and the base portion of the fluid exchange valve can be pivotably received by the pathway. Where the fluid exchange valve is pivotable between the first condition and the second condition and has first and second ends, a first lever arm can be fixed to pivot with the first end of the fluid exchange valve and a second lever arm can be fixed to pivot with the second end of the fluid exchange valve. The first and second lever arms can be generally aligned longitudinally with the stopper and the bottle or other vessel in which it is disposed when the fluid exchange valve is in the second condition, and the first and second lever arms can be generally orthogonal to the stopper and the bottle or other vessel in which it is disposed when the fluid exchange valve is in the first condition. Under such constructions and where the first and second lever arms are substantially equal in size and shape, the lever arms can support and stabilize a retained vessel.

A further possibility under the disclosed system is for the chamber to be disposed within a substantially rigid shell, which can protect the chamber against, for example, inadvertent damage or compression. The shell can be retained relative to the vessel and the remainder of the system by, for example, opposed first and second wings that project from the shell for engaging the vessel.

It is contemplated that the chamber can be replenished in a reverse volumetric displacement process by supplying a displacement liquid into the open inner volume of the vessel through the fluid exhaust pathway to volumetrically displace preservative gas back into the chamber. It is further possible to replenish the chamber through an inert gas production canister. The inert gas production canister can have an open inner volume for retaining a volume of air and an oxygen absorbing material for removing oxygen from the air. The inert gas production canister could have a resiliently compressible shell, a lid slidably engaged with a shell, or some other construction.

A method for volumetric displacement preservation for preserving a volume of flowable substance in an open inner volume of a vessel as taught herein can be founded on providing even a basic volumetric displacement preservation system as first described above. Then, the stopper can be applied to the vessel, and the orifice of the chamber can be connected to the second end of the fluid inlet pathway. The vessel can be disposed in a dispensing condition, and the fluid exhaust pathway and the fluid inlet pathway can be disposed in open conditions. With that, a volume of the flowable substance can be dispensed from the open inner volume of the vessel through the fluid exhaust pathway, such as under the force of gravity. Simultaneously, a volume of preservative gas will be drawn into the open inner volume of the vessel through the fluid inlet pathway in volumetric displacement of the liquid exhausted through the fluid exhaust pathway.

The step of disposing the vessel in a dispensing condition can, but need not, happen before the step of disposing the fluid exhaust pathway and the fluid inlet pathway in open conditions. When the dispensing step is complete, the fluid exhaust pathway and the fluid inlet pathway can be adjusted to closed conditions, potentially while the vessel is in a dispensing condition to avoid the introduction of air into the inner volume of the vessel.

When the preservative gas in the chamber is at least partially exhausted, the chamber could be disposed of or replenished. In one practice of the invention, the chamber can be replenished in a reverse volumetric displacement process for harvesting preservative gas from the inner volume of a vessel and into the inner volume of the chamber. To do so, a volume of displacement liquid can be supplied into the open inner volume of the vessel through the fluid exhaust pathway with the fluid exhaust pathway and the fluid inlet pathway in open conditions to cause preservative gas within the open inner volume of the vessel to be volumetrically displaced into the chamber through the fluid inlet pathway. In another practice of the invention, the chamber can be replenished with gas from an inert gas production canister. The inert gas production canister can have an open inner volume for retaining a volume of air and an oxygen absorbing material for removing oxygen from the air.

Where the inert gas production canister has a resiliently compressible shell, the step of replenishing the chamber can include the step of squeezing the compressible shell to transfer preservative gas from the compressible shell to the chamber. Where the inert gas production canister has a lid slidably engaged with a shell for enabling a change in the open inner volume of the shell, the step of replenishing the chamber can include the step of sliding the lid relative to the shell to reduce the open inner volume of the inert gas production canister to transfer preservative gas from the compressible shell to the chamber. In either case, the process can further include the steps of allowing air into the open inner volume of the inert gas production canister and waiting a period of time to permit the air to be reduced in oxygen content.

Further disclosed herein is an automatic replenishing system for automatically replenishing preservative gas within a compressible bladder for supply to the inner volume of a vessel. The replenishing system has a compressible bladder with an outer wall and an expandable and compressible inner volume for retaining a volume of preservative gas and at least one orifice allowing a passage of preservative gas. A supply conduit is adapted to receive preservative gas from a source of preservative gas. The supply conduit has a first end for supplying preservative gas to the compressible bladder and a second end for being fluidically connected to the source of preservative gas. A discharge conduit is adapted to supply preservative gas to a vessel. The discharge conduit has as first end for receiving preservative gas from the compressible bladder and a second end for being fluidically connected to a vessel. An inflation detection system is operable to detect a first condition in which the compressible bladder is inflated with preservative gas to a state of inflation and a second condition in which the compressible bladder is inflated with preservative gas below the state of inflation. A valve system is disposed between the source of preservative gas and the compressible bladder. The valve system is operative to permit preservative gas to flow from the source of preservative gas and into the compressible bladder when the compressible bladder is in the second condition, and the valve system is operative to prevent preservative gas from flowing from the source of preservative gas and into the compressible bladder when the compressible bladder is in the first condition.

In certain embodiments, the valve system and the inflation detection system are disposed within a housing, and the compressible bladder can be disposed within a sub-housing within the housing.

The automatic replenishing system, the valve system, and the inflation detection system can be operative to maintain the volume of preservative gas in the compressible bladder substantially at ambient pressure. Where the compressible bladder has a fully inflated condition, the inflation detection system can be operative to detect when the compressible bladder is inflated to within a predetermined range of the fully inflated condition.

In manifestations of the automatic replenishing system, the inflation detection system comprises an electro-mechanical system. By way of example, the inflation detection system can include a deflection switch, such as a pivoting switch, a compressible switch, or any other type of deflection switch, disposed to be moved by the outer wall of the compressible bladder when the compressible bladder is inflated with preservative gas to the state of inflation. The deflection switch can be biased toward the compressible bladder, such as under the force of gravity, but resilience, by a spring mechanism, or by some other method of combination thereof. Further, the deflection switch can be considered to have an activated state wherein the deflection switch is disposed at or beyond an inward position with respect to the inner volume of the compressible bladder and a deactivated state when the deflection switch is moved outwardly by the outer wall of the compressible bladder when the volume of preservative gas in the compressible bladder reaches the predetermined state of inflation.

The valve system can, in a non-limiting embodiment, comprise a solenoid valve that is in electrical communication with the inflation detection system. In such manifestations, the solenoid valve can be induced by the inflation detection system to a closed condition to prevent the flow of preservative gas from the source of preservative gas to the compressible bladder when the compressible bladder is in the first condition, and the solenoid valve can be induced by the inflation detection system to an open condition to permit the flow of preservative gas from the source of preservative gas to the compressible bladder when the compressible bladder is in the second condition.

To prevent the compressible bladder from being filled with preservative gas too rapidly, a flow-limiting connector can be interposed between the second end of the supply conduit and the compressible bladder. For instance, the flow-limiting connector can take the form of a narrow-diameter tube with an inner diameter less than an inner diameter of the supply conduit. Moreover, a fluidic connector can be disposed at the second end of the discharge conduit. For instance, a valve connector can be provided for coupling to a fluid exchange structure according to the present invention.

Further still, a flow meter can be incorporated within the system to detect a volume of preservative gas dispensed from the compressible bladder. Additionally, electronic memory can be in communication with the flow meter for tracking volumes of preservative gas dispensed from the compressible bladder. With that, the volume of material dispensed from and retained within a given vessel or a plurality of vessels can be determined, tracked, and analyzed.

One will appreciate that the foregoing discussion broadly outlines the more important goals and features of the invention to enable a better understanding of the detailed description that follows and to instill a better appreciation of the inventors∝ contribution to the art. Before any particular embodiment or aspect thereof is explained in detail, it must be made clear that the following details of construction and illustrations of inventive concepts are mere examples of the many possible manifestations of the invention.

BRIEF DESCRIPTION OF THE DRAWINGS

In the accompanying drawing figures:

FIGS. 20A through 20D depict a series of steps in a process of producing and harvesting inert gas using an inert gas production canister;

DETAILED DESCRIPTION OF PREFERRED EMBODIMENTS

The automatic system for the conservation of gas and other substances, the systems and methods for preserving and dispensing wine and other perishable substances, and the automatic preservative gas replenishing system disclosed herein are subject to a wide variety of embodiments. However, to ensure that one skilled in the art will be able to understand and, in appropriate cases, practice the inventions disclosed herein, certain preferred embodiments of the broader inventions are described below and shown in the accompanying drawing figures.

Figure 46:
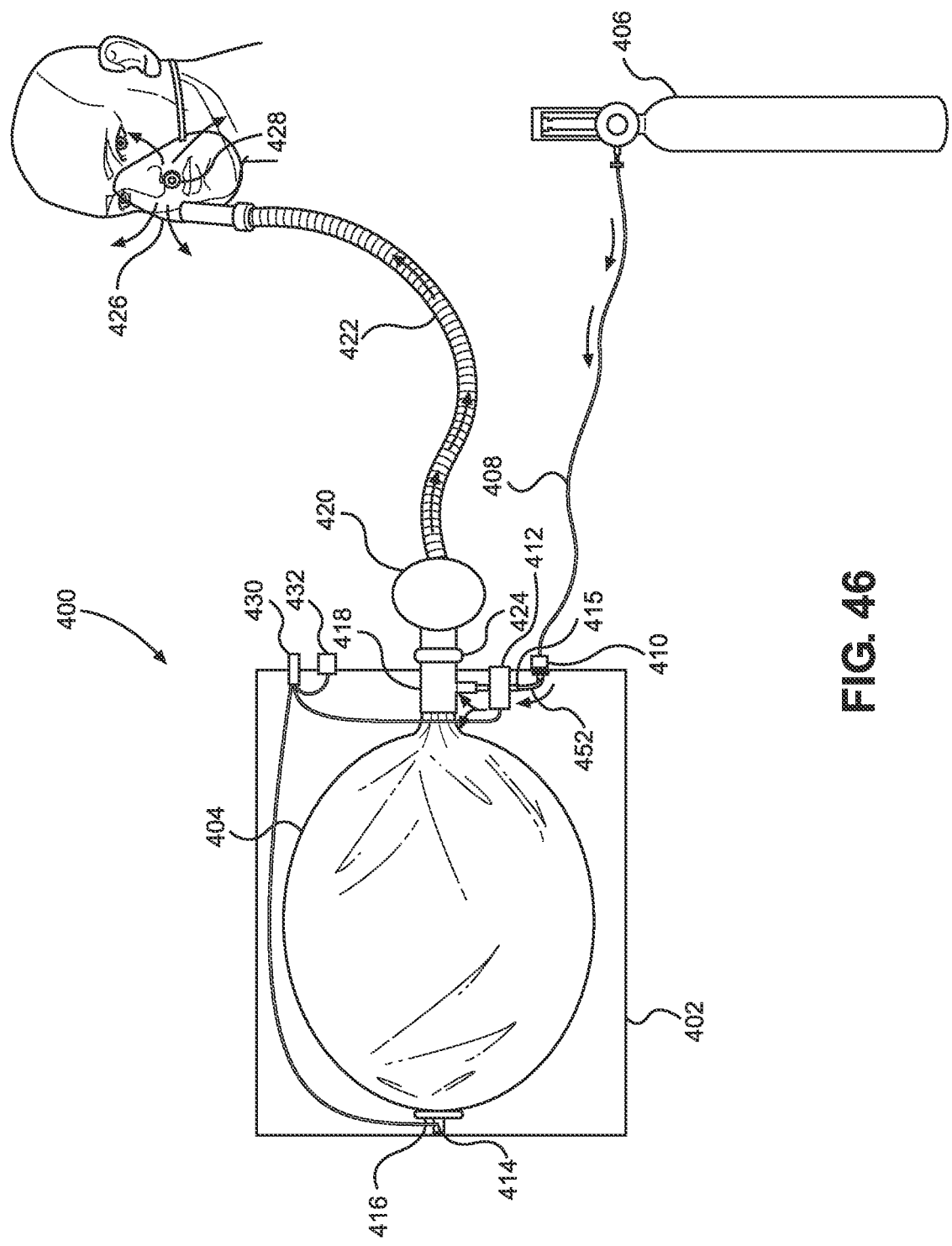
FIG. 46 is a schematic view of an automatic system for the conservation of gas according to the present invention.

Looking more particularly to the drawings, the structure and operation of an automatic gas conservation system 400 according to the present invention can be understood with reference to FIG. 46. As shown and described herein, the automatic gas preservation system 400 provides an on-demand supply of oxygen at ambient pressure to a recipient, such as a patient breathing mask 426, from a donor reservoir 404. The donor reservoir 404 retains oxygen at ambient pressure and is continually supplied with oxygen from an oxygen source 406, such as a tank of compressed oxygen gas or liquid oxygen. With the donor reservoir 404 retaining oxygen at ambient pressure, a full and ample supply of oxygen is constantly available for patient inspiration. Concomitantly, oxygen losses during patient expiration are substantially eliminated thereby conserving the supply of oxygen without compromising availability to the individual recipient since oxygen within the donor reservoir 404 is automatically replenished.

Figure 55:
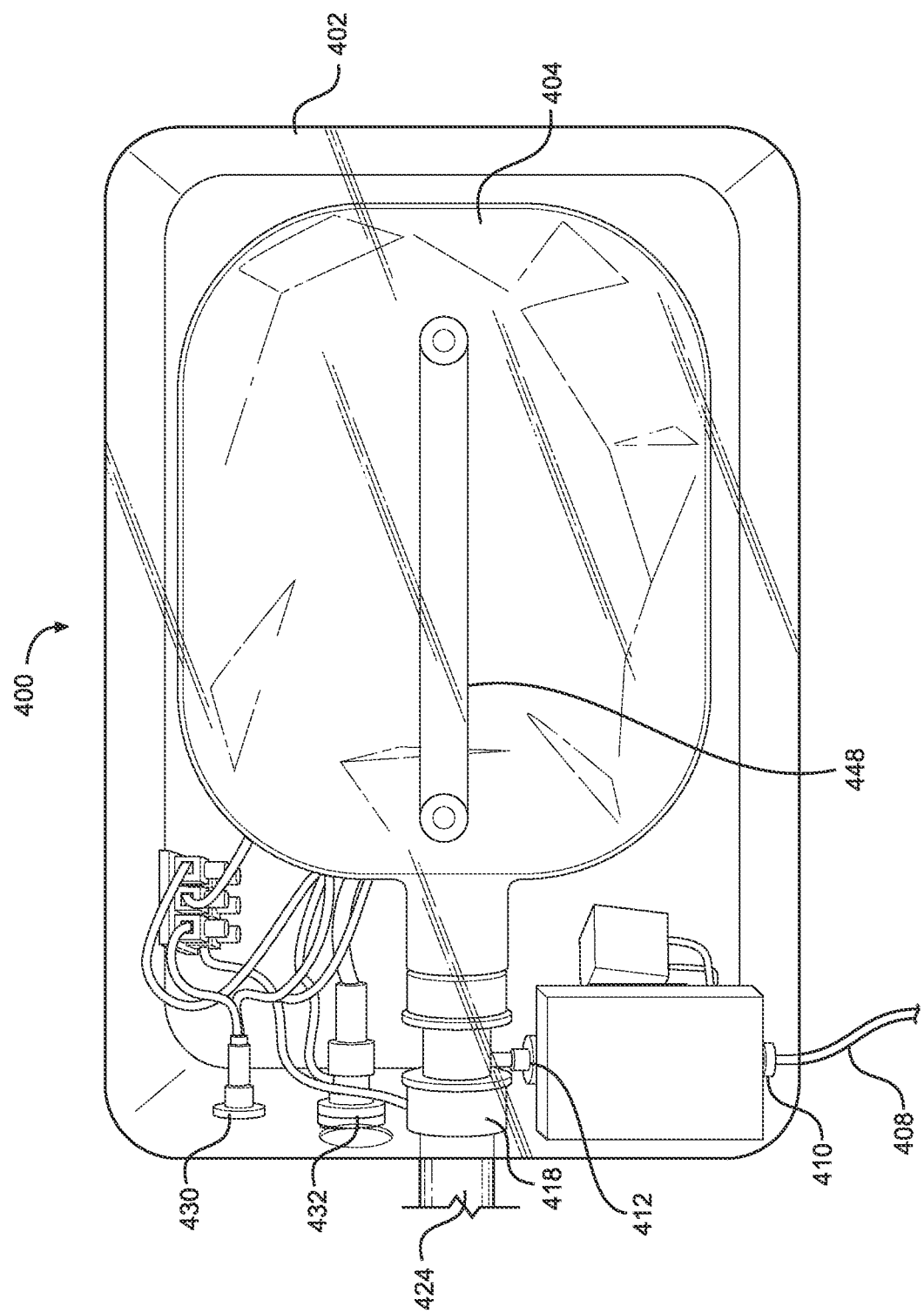
FIG. 55 is a bottom plan view of the automatic system for the conservation of gas of FIG. 54.
Figure 56:
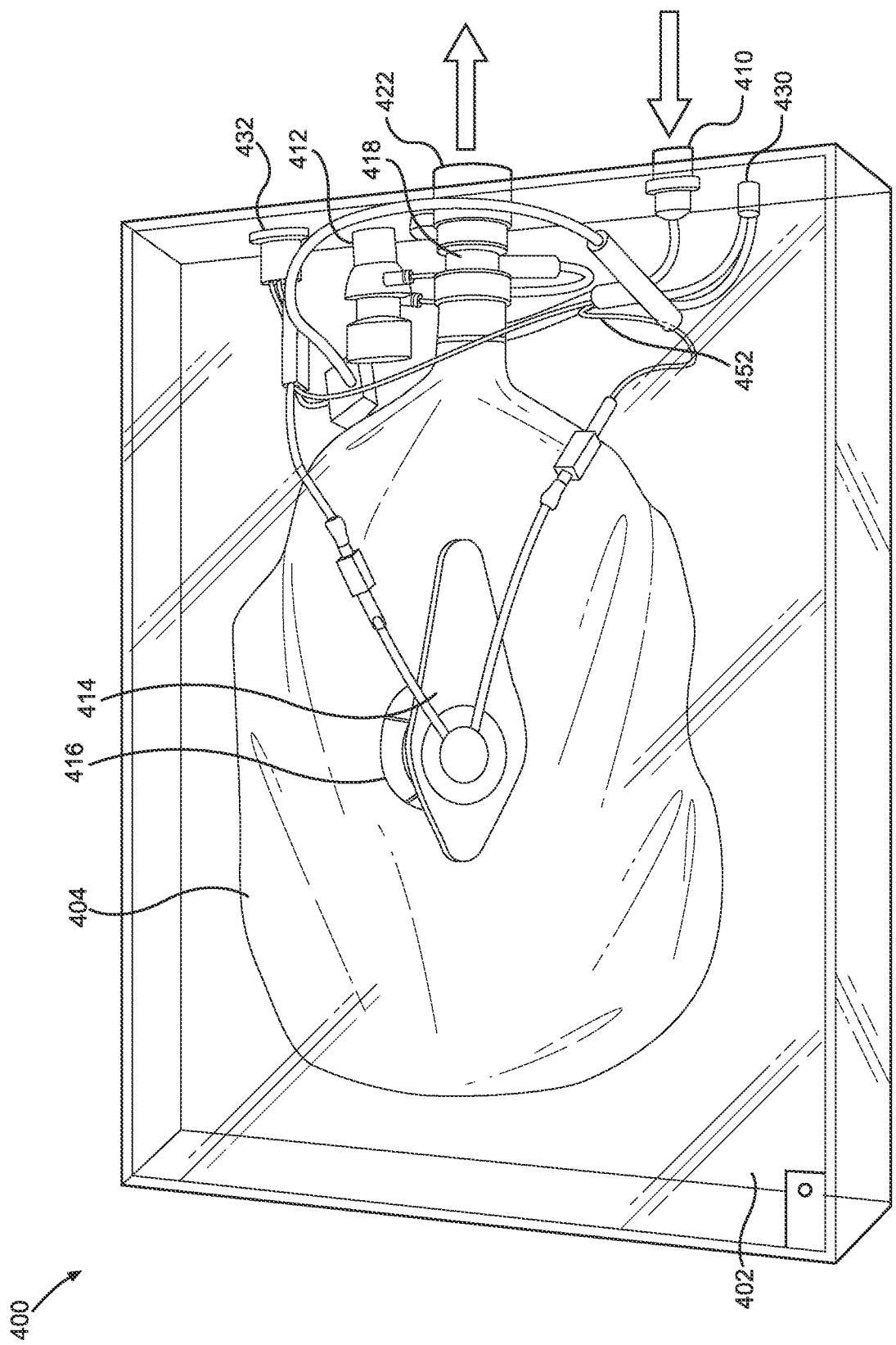
FIG. 56 is a top plan view of an alternative automatic system for the conservation of gas according to the invention.
Figure 57:
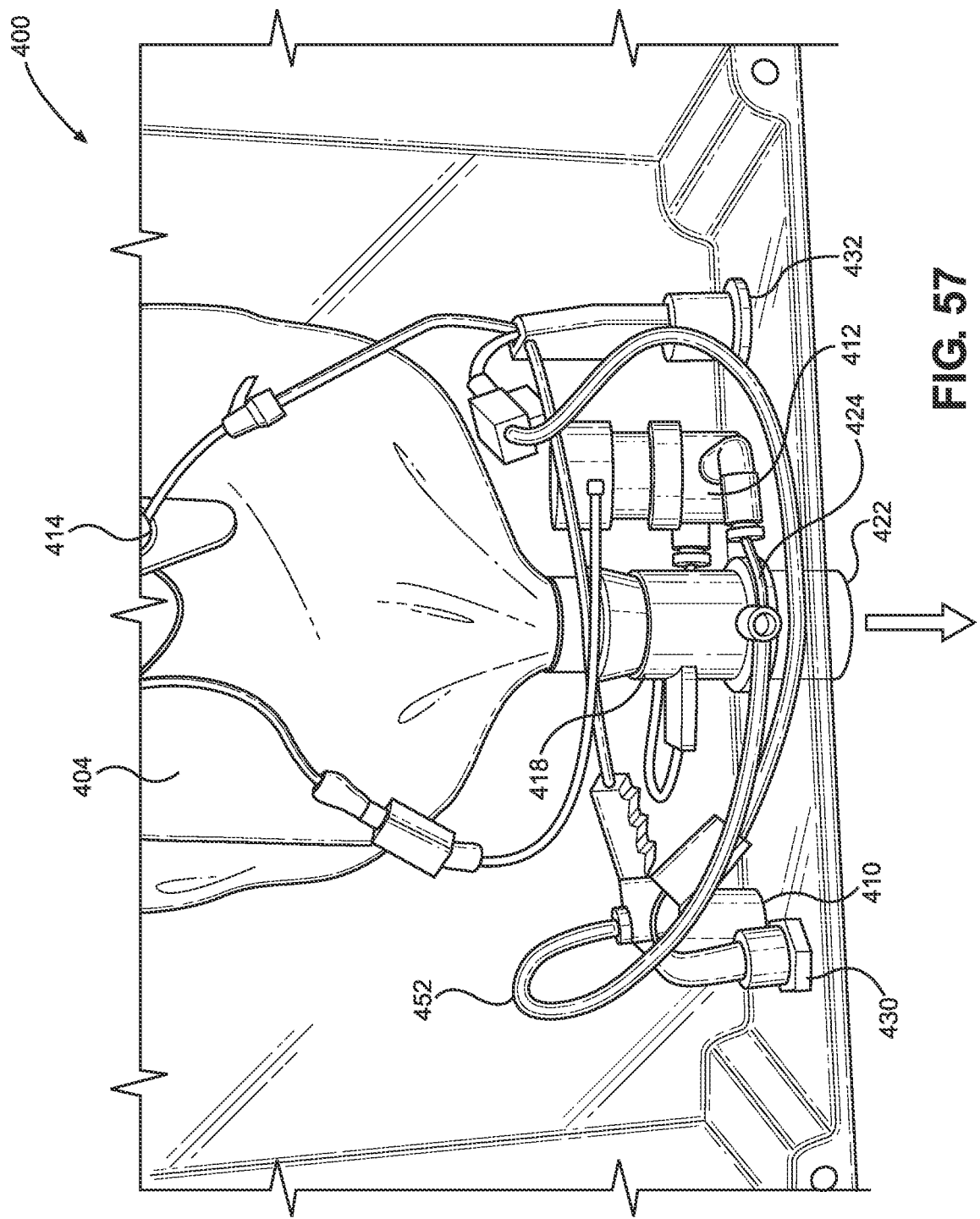
FIG. 57 is an amplified top plan view of the automatic system for the conservation of gas of FIG. 56.
Figure 58:
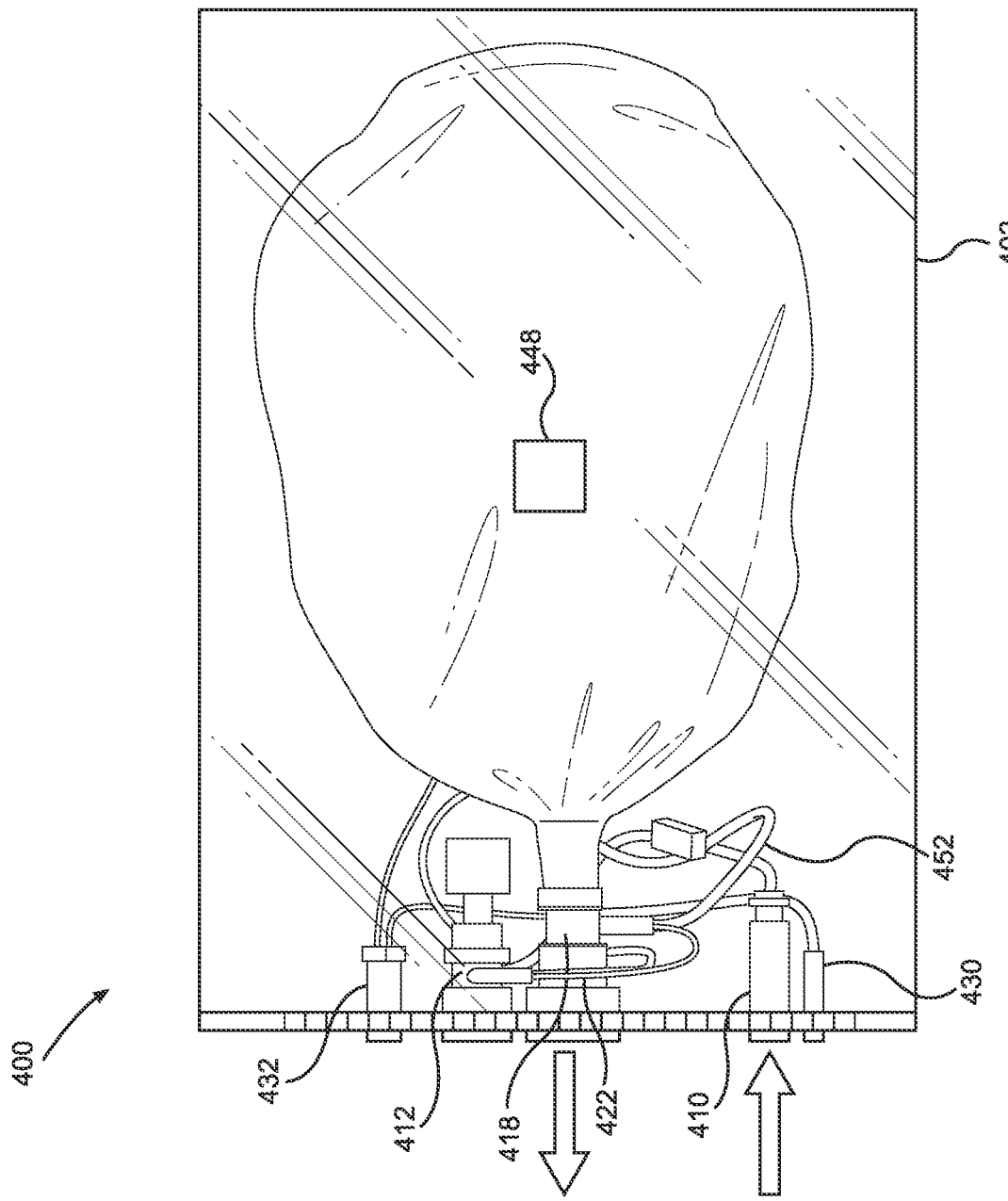
FIG. 58 is a bottom plan view of the automatic system for the conservation of gas of FIG. 56.
Figure 59:
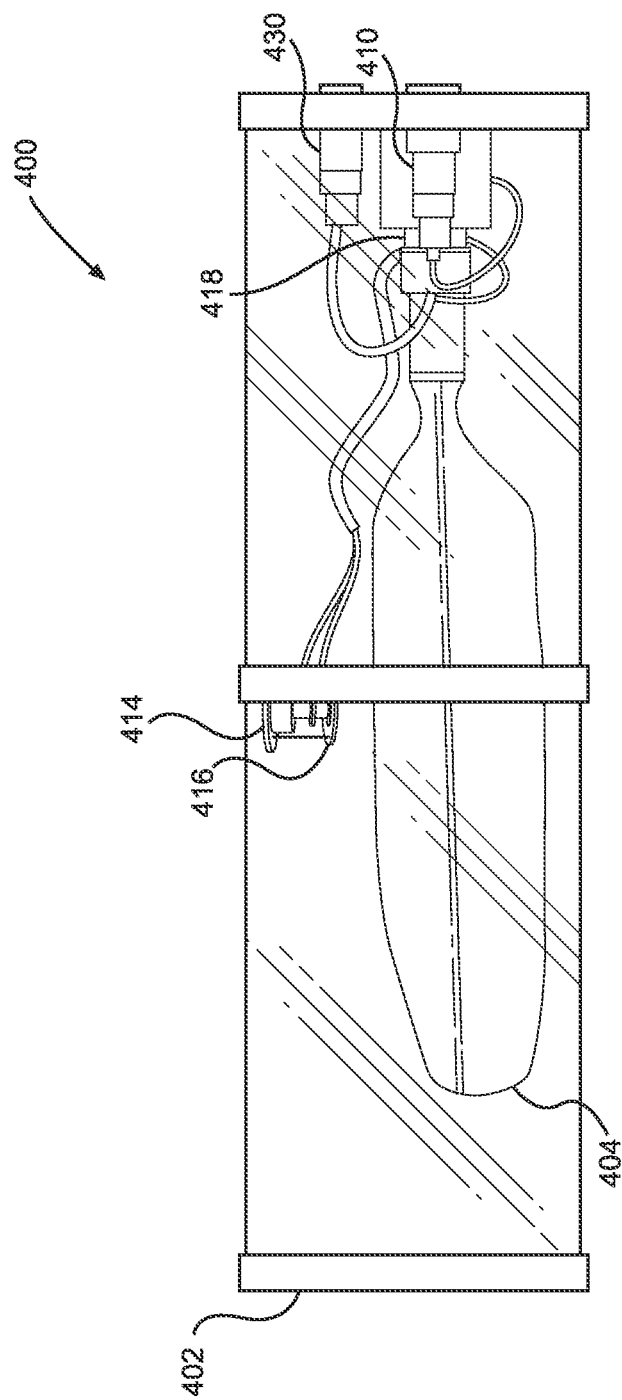
FIG. 59 is a view in side elevation of the automatic system for the conservation of gas of FIG. 56.
Figure 60:
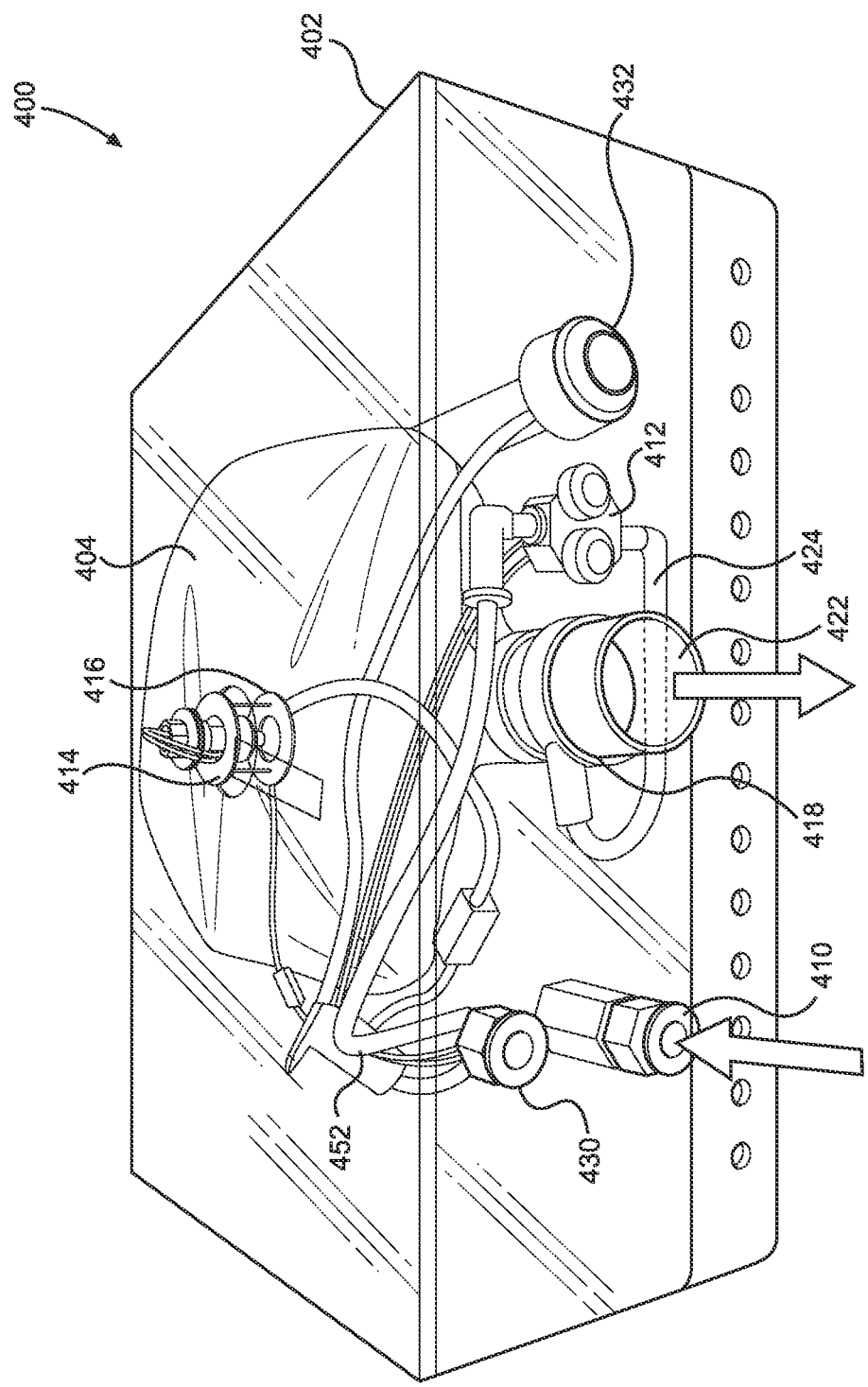
FIG. 60 is an anterior perspective view of the automatic system for the conservation of gas of FIG. 56.

The donor reservoir 404 in this embodiment comprises an expandable and compressible shell, bladder, or other expandable and compressible body that is disposed within a housing 402, which could be a primary housing or a sub-housing within a larger structure. However, the donor reservoir 404 need not necessarily be within a housing 402 to be within the scope of the invention. The housing 402 defines boundaries for the reservoir 404 so that the shell of the reservoir 404 presses toward one or more portions of the boundary defined by the housing 402 as the reservoir 404 is expanded. In this non-limiting example, the housing 402 has a bottom that defines a lower boundary for the reservoir 404, a top that defines an upper boundary for the reservoir 404, and distal ends that define longitudinal boundaries for the reservoir 404. Here, the reservoir 404 has an oblong, egg shape, and the housing 402 has a general cube shape, but other shapes and combinations of shapes are readily possible and within the scope of the invention except as it might be expressly limited by the claims. As in the embodiment of the automatic gas preservation system 400 shown in FIG. 55, for example, the lower wall portion of the shell of the reservoir 404 can be adhered or otherwise secured to the bottom of the housing 402, such as by an adhesive strip 448 or in any other manner.

In this example, the reservoir 404 is defined by first and second oblong panels joined along their edges in a sealed manner to define the shell or outside wall structure with a body portion and a neck. The reservoir 404 is sealed but for an entry orifice in the neck of the reservoir 404. The shell is formed from a flexible and substantially gas impermeable material with it being known to one of skill in the art that numerous such materials are possible, each within the scope of the invention. The shell of the reservoir 404 could, for example, be formed from a flexible polymeric material with or without a lining layer. The material defining the reservoir 404 could, for example, comprise a foil formed by one or more layers of polymeric material with an aluminum lining. Other formations of the reservoir 404 are possible and within the scope of the invention. The reservoir 404 can have combinations including one or more flexible walls, rigid walls, compressible walls, collapsible walls, expandable walls, thin walls, or other walls capable of keeping a volume gas inside.

Preferably, as is enabled by formation of the reservoir 404 of a lightweight, flexible foil, the reservoir 404 once expanded tends to substantially maintain an expanded shape and configuration, whether by its own structural integrity or otherwise, even when it is open to ambient pressure, such as by a fluidic connection to the recipient 426 through ambient pressure tubing 422. As taught herein, when expanded, the reservoir 404 in preferred embodiments does not significantly collapse on its own due to the weight of its walls. When filled with oxygen, the reservoir 404 thus temporarily stores a compartmented volume of oxygen at ambient pressure waiting to be drawn therefrom by the recipient 426.

A fluidic connector 418, which in this example comprises a T-shaped connector, has a first, longitudinal port in fluidic communication with the donor reservoir 404, such as through the aperture in the neck of the reservoir 404. The fluidic connector 418 has a second, longitudinal port in fluidic communication with the ambient pressure tubing 422 and, through that tubing 422, the recipient 426. Finally, the fluidic connector 418 has a third, lateral port between the first and second openings in fluidic communication with the oxygen source 406. The fluidic communication from the source 406 to the connector 418 could, for instance, be through high-pressure tubing 408 from the oxygen source 406 to an oxygen connector 410 fixed to the housing 402 and high-pressure tubing 452 from the oxygen connector 410 to a supply valve 412. The first, second, and third ports are in fluidic communication with one another within the fluidic connector 418.

The supply valve 412, which in this example comprises an electromechanical solenoid valve 412, has an open condition and a closed condition. The valve 412 is fluidically interposed between the pressurized oxygen source 406 and the reservoir 404. When the supply valve 412 is in the open condition, oxygen can be passed from the oxygen source 406, through the tubing 408, through the valve 412, through the connector 418, and into the reservoir 404. When the valve 412 is in the closed condition, the passage of oxygen between the oxygen source 406 and the reservoir 404 is prevented.

Figure 61:
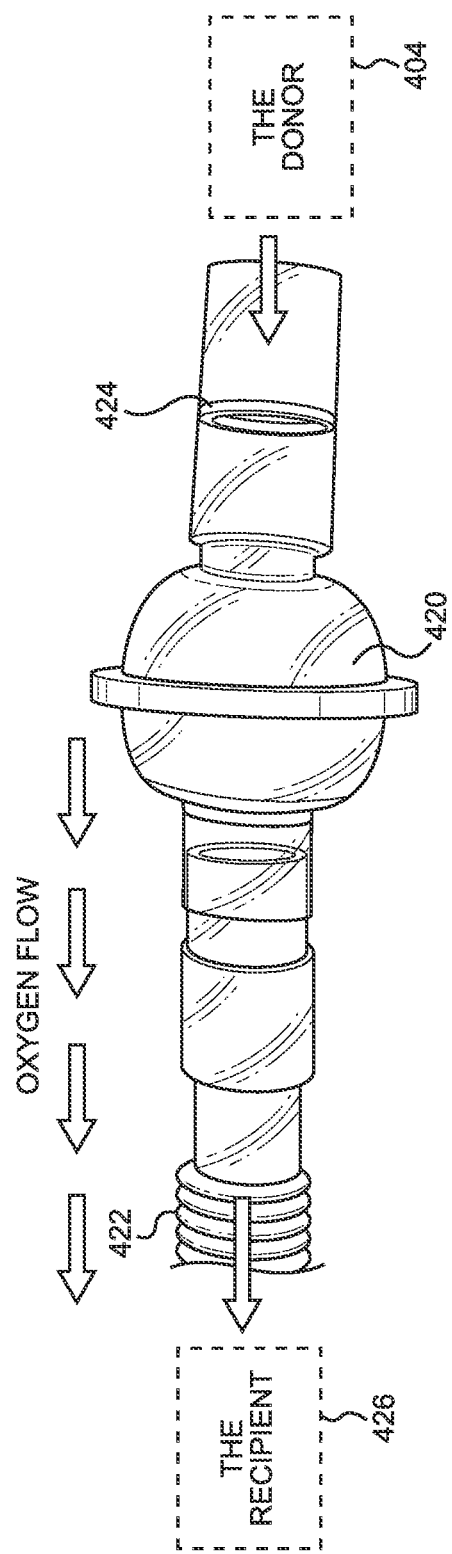
FIG. 61 is a perspective view of a filter and one-way inspiratory valve for the automatic system for the conservation of gas of FIG. 56.

A one-way inspiratory valve 424 is interposed between the reservoir 404 and the recipient 426, such as by being fluidically connected to the second port of the fluidic connector 418 and with the fluidic connector 418 fluidically connected through its first port to the neck of the reservoir 404. The one-way inspiratory valve 424 is operative to enable gas to flow from the donor reservoir 404, through the ambient pressure tubing 422, and to the recipient 426 but to prevent reverse gas flow, such as from the recipient 426 and into the donor reservoir 404. A gas filter 420 is fluidically interposed between the recipient 426 and the one-way inspiratory valve 424 and thus between the recipient 426 and the donor reservoir 404. The filter 420 and the one-way inspiratory valve 424 are shown apart from the remainder of the automatic gas conservation system 400 in FIG. 61.

As disclosed herein, the volume of oxygen in the donor reservoir 404 is retained substantially at ambient pressure. Ambient pressure can be defined as the pressure of the air surrounding the donor reservoir 404. As a recipient undergoes the inspiratory phase of breathing, oxygen will be drawn from the donor reservoir 404 through the ambient pressure tubing 422 thereby drawing from and tending to reduce the volume of oxygen in the donor reservoir 404. Due to the compressible nature of the donor reservoir 404, the reservoir 404 will tend to contract. When it does contract, the donor reservoir 404 is automatically replenished with oxygen by operation of an inflation detection system without pressurization of the reservoir 404 so that the oxygen within the reservoir 404 remains substantially at ambient pressure.

The inflation detection system has a first condition wherein replenishing oxygen is not supplied to the donor reservoir 404 and a second condition wherein replenishing oxygen is supplied to the donor reservoir 404. The first condition can be a condition wherein the donor reservoir 404 is inflated with oxygen to a certain, predetermined state of inflation, and the second condition can be a condition wherein the donor reservoir 404 is inflated with oxygen below the predetermined state of inflation. The inflation detection system is operative to detect when the donor reservoir 404 has reached the predetermined state of inflation. The predetermined state of inflation can be detected when the donor reservoir 404 reaches a predetermined size or other inflation condition in any dimension or combination of dimensions. In embodiments of the invention, the donor reservoir 404 can be considered to have a fully inflated condition, and the inflation detection system detects when the donor reservoir 404 is inflated to the fully inflated condition or to within a predetermined range of the fully inflated condition. By way of example and not limitation, the inflation detection system can detect when the donor reservoir 404 is inflated with oxygen at or above a threshold inflation level, which may be equal to or less than the fully inflated condition.

Made aware of the present invention, one skilled in the art may appreciate plural mechanisms that would operate as inflation detection systems to detect when the donor reservoir 404 is inflated to the predetermined state of inflation. Each such mechanism is within the scope of the invention except as it may be expressly limited by the claims. Inflation detection mechanisms could comprise mechanical systems, electrical systems, electromagnetic systems, optical systems, electro-mechanical systems, sound-activated systems, movement sensors, light sensors, and any other type of system effective to detect when the donor reservoir 404 is inflated to a predetermined state of inflation with it again being noted that the predetermined state of inflation may be reached while the oxygen within the donor reservoir 404 is substantially at ambient pressure.

In the non-limiting embodiment of FIG. 46, the inflation detection system comprises an electro-mechanical system for detecting when the donor reservoir 404 is filled to the predetermined state of inflation. The inflation detection system has a contact structure 416 disposed to contact, to be contacted by, to be moved by, or otherwise to be actuated by the donor reservoir 404 when the reservoir 404 reaches a stage of inflation. Within the scope of the invention, the location and construction of the contact structure 416 could vary. In the embodiment of FIG. 46, for instance, the contact structure 416 is disposed to project from or through the distal end wall of the housing 402 and into the inner volume of the housing 402 so that it projects toward and can engage the distal end of the reservoir 404. In the embodiments of FIGS. 48 through 60, however, the contact structure 416 is disposed to project from or through the upper wall of the housing 402 and into the inner volume of the housing 402 to engage a mid-portion of the reservoir 404. There, the contact structure 416 is retained by a support structure 434 that is fixed to the upper wall of the housing 402. According to the invention, the contact structure 416 could be otherwise retained.

The contact structure 416 is positioned to be moved by the donor reservoir 404 as the reservoir 404 expands toward an inflated condition. The contact structure 416 can, for instance, be depressed, pivoted, rotated, or otherwise actuated by the donor reservoir 404 and more particularly by an expansion of the donor reservoir 404. The contact structure 416 operates as or as a component of or to actuate a flow switch 414. When the contact structure 416 is actuated by the expansion of the donor reservoir 404, the flow switch 414 is caused to actuate the valve 412 between the ON condition where oxygen is permitted to flow from the oxygen source 406 to the reservoir 404 to replenish and fill the reservoir 404 and the OFF condition where oxygen is prevented from flowing from the oxygen source 406 to the reservoir 404. The contact structure 416 is biased, such as by spring force, under the force of gravity, by resiliency, or any other biasing method or combination thereof toward the donor reservoir 404.

Figure 62:
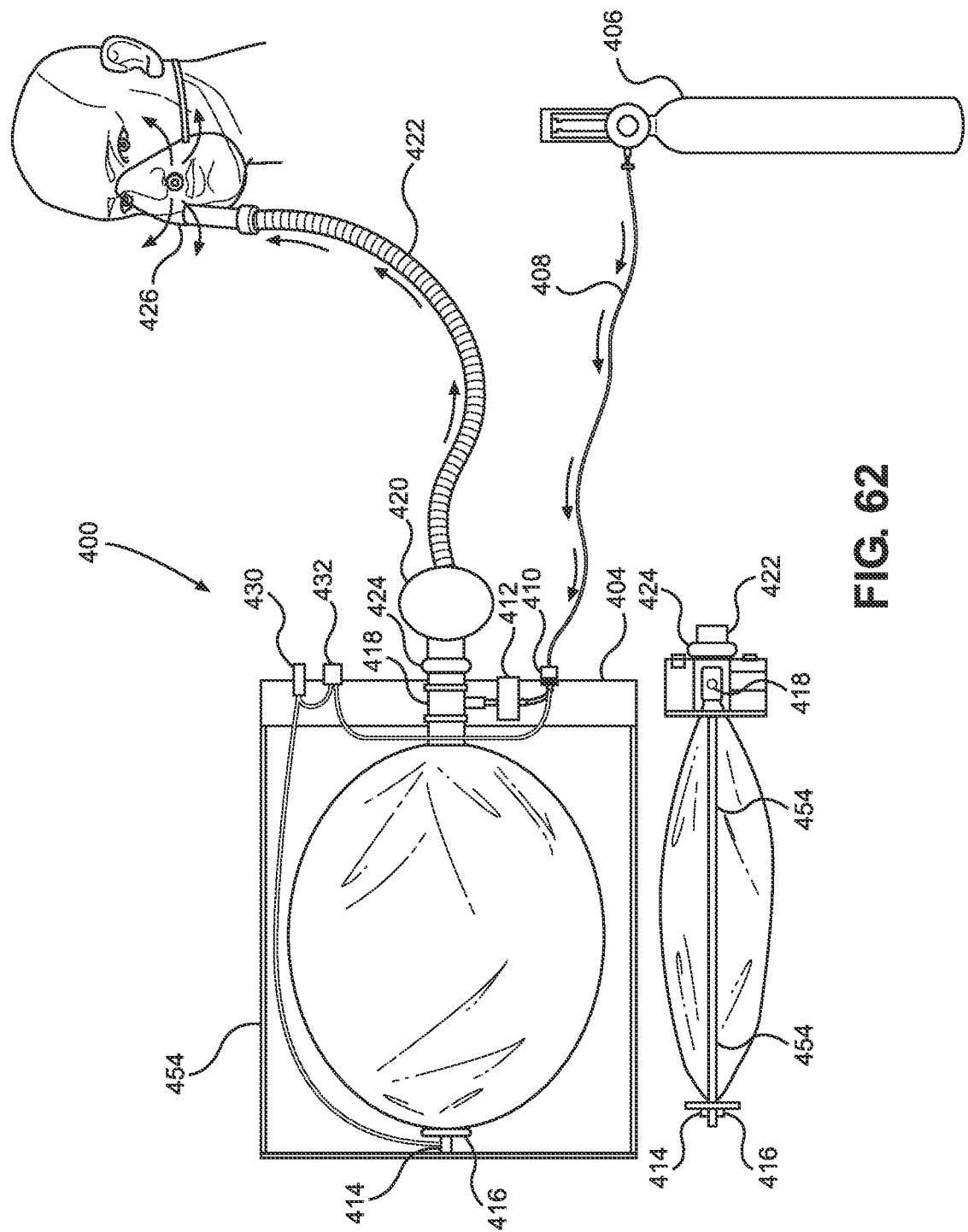
FIG. 62 comprises schematic top plan and side elevation views of another automatic system for the conservation of gas according to the invention.

In the non-limiting embodiment of FIG. 46, the donor reservoir 404 is disposed within a housing 402. Additionally or alternatively, the donor reservoir 404 could be disposed within a sub-housing that, in turn, could be disposed in the housing 402 or that could stand independently. Still further, as is shown in FIG. 62, for example, the donor reservoir 404 could be disposed without a housing or enclosure, in which case the contact structure 416 and potentially the flow switch 414 described further hereinbelow could be otherwise retained, such as by a surrounding band, a rigid arm, or another retaining structure 454, for contact or other sensing or engagement relative to the donor reservoir 404. The contact structure 416 and the flow switch 414 could be retained together, potentially as a unit, or in separate dispositions. In FIG. 62, the contact structure 416 is retained by the retaining structure 454, which could be a rigid support arm or any other retaining structure, to engage the donor reservoir 404, and the flow switch 414 is integrated with the contact struture 416.

The contact structure 416 is thus retained by the housing 402, by the retaining structure 454, or otherwise to contact the reservoir 404. Without limiting the invention, the contact structure 416 could be retained to contact the reservoir 404 by being secured partially or entirely within the housing 402 or through an aperture in the housing 402 or through an aperture in a sub-housing that retains the reservoir 404, or the contact structure 416 could be retained to contact a donor reservoir 404 that is not in a housing at all.

The flow switch 414 has an activated state, which may be considered to be the ON condition, when the contact structure 416 is sufficiently moved, such as by extension, pivoting, or other movement, in an inward direction toward the inner volume of the donor reservoir 404. The contact structure 416 is permitted to move inwardly in the direction toward the donor reservoir 404 to the activated state when the volume of oxygen in the donor reservoir 404 falls below the predetermined state of inflation such that the outside wall is or can be deflected or moved inwardly. The flow switch 414 has a deactivated state, which may be considered to be the OFF condition, when the contact structure 416 is moved, such as by retraction, pivoting, or other movement in an outward direction away from the donor reservoir 404. The contact structure 416 is moved outwardly to adjust the flow switch 414 to the deactivated state, which is the OFF condition, when the volume of oxygen in the donor reservoir 404 reaches the predetermined state of inflation to cause the outside wall of the donor reservoir 404 to be advanced outwardly by the expansion of the donor reservoir 404. For instance, where the contact structure 416 is a depression switch, expansion of the donor reservoir 404 will press the outer wall or shell of the donor reservoir 404 outwardly to press the contact structure 416 and the flow switch 414 to the deactivated state.

Figure 52:
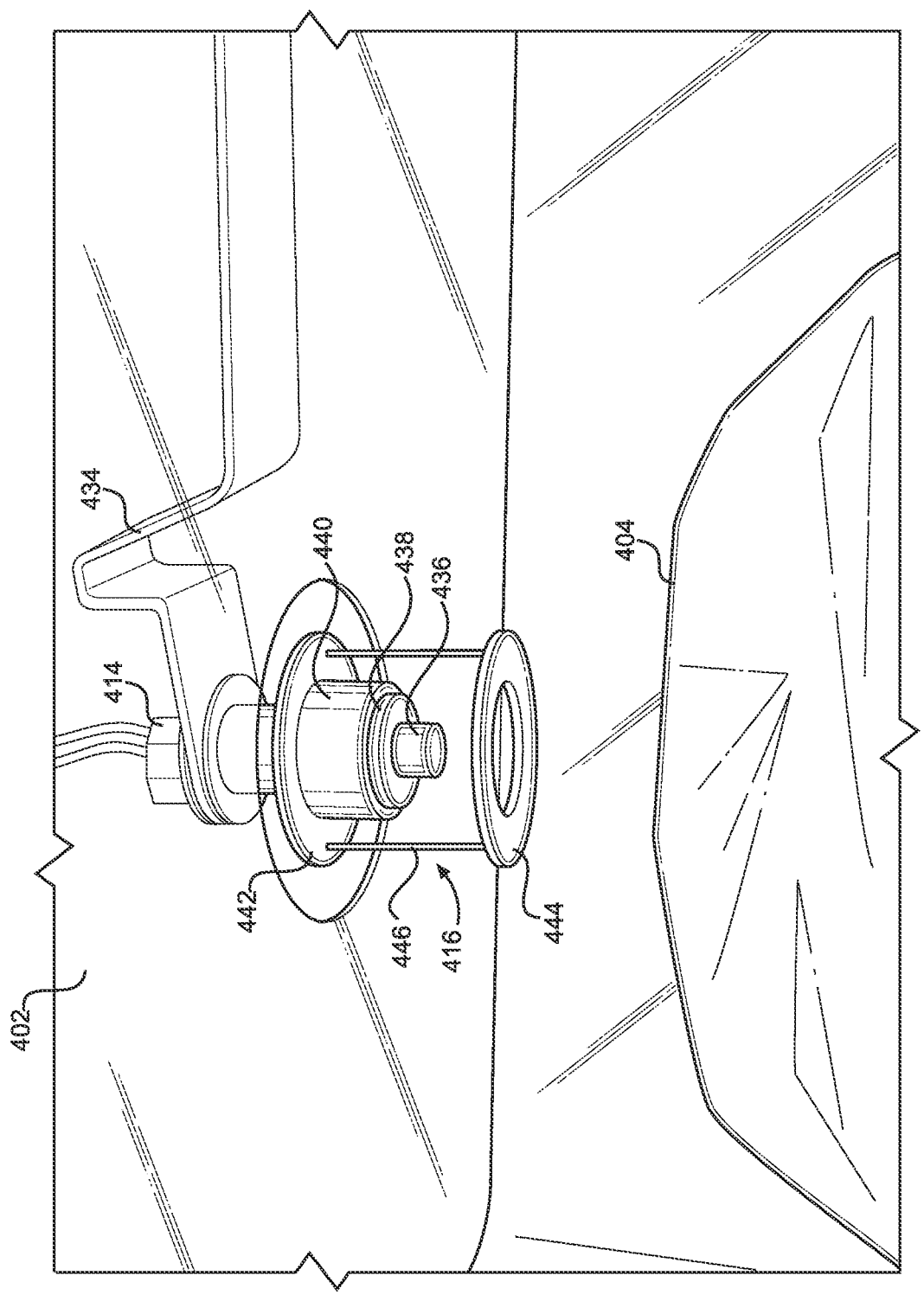
FIG. 52 is a lower perspective view of the inflation detection system again in an ON condition.
Figure 53:
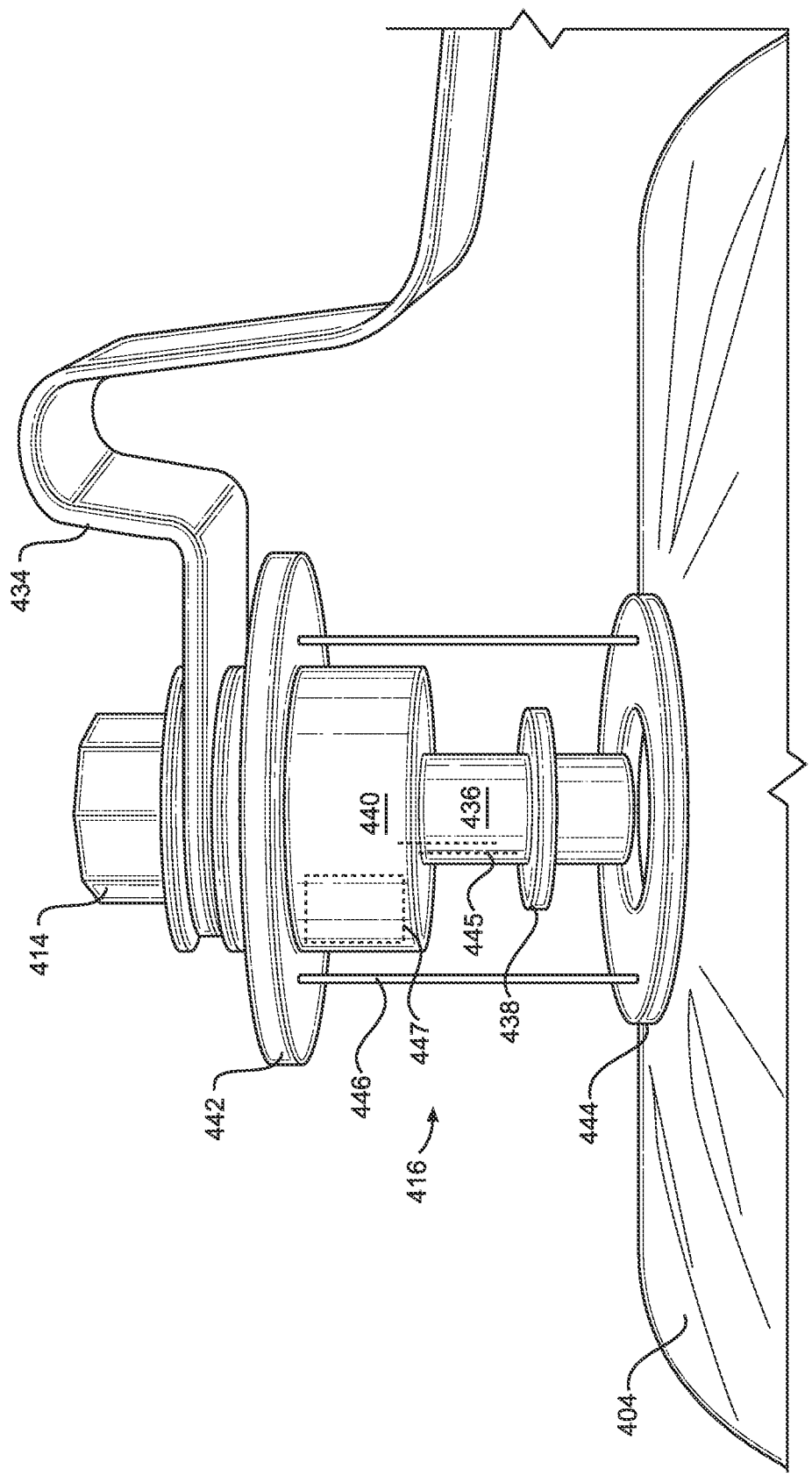
FIG. 53 is a view in side elevation of the inflation detection system in an OFF condition.
Figure 54:
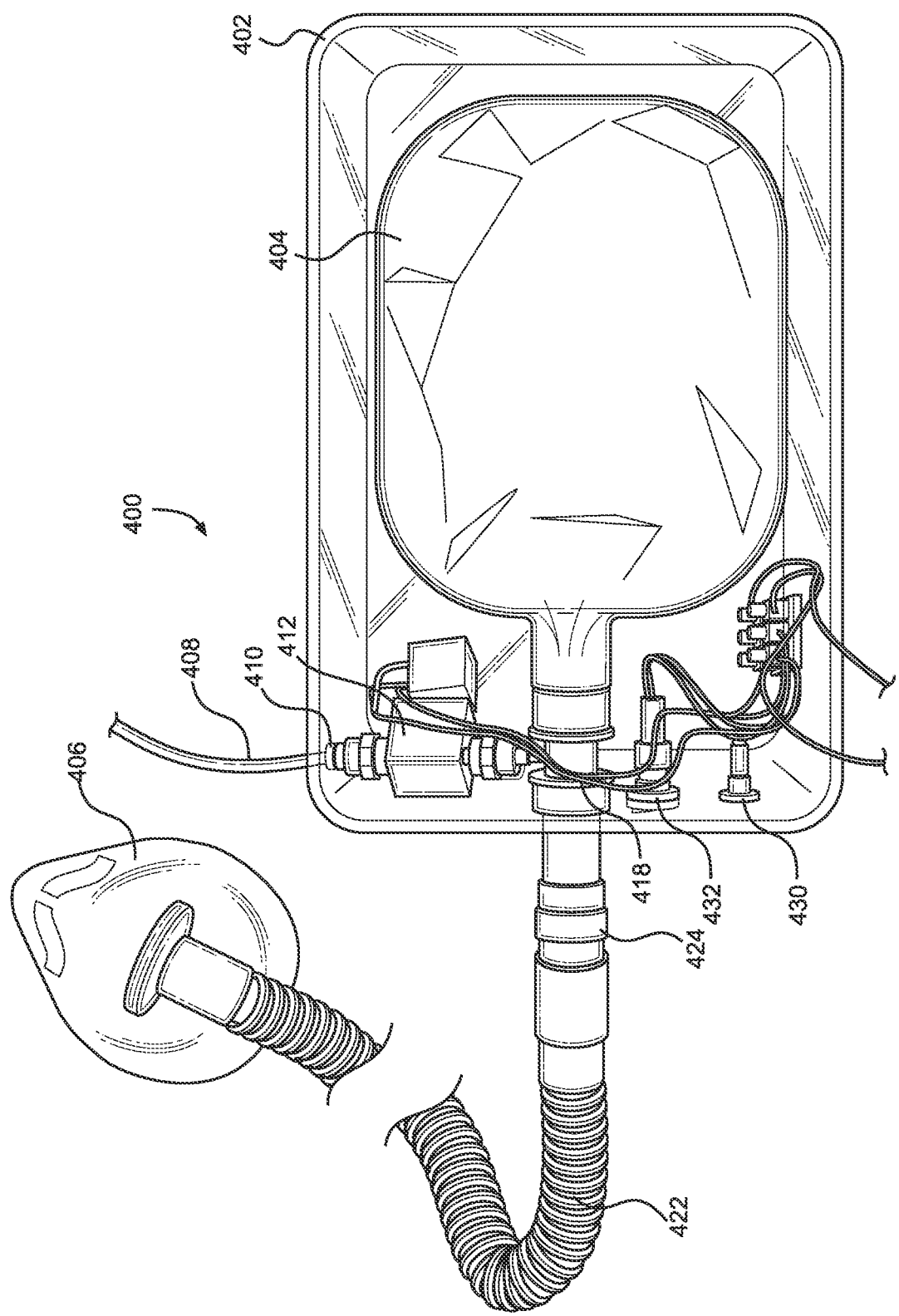
FIG. 54 is a top plan view of an automatic system for the conservation of gas as disclosed herein with the cover portion and the retained inflation detection system removed.

In the embodiment of FIGS. 48 through 55, the contact structure 416 and the switch 414 are embodied as a float switch with an actuation framework. With particular reference to FIGS. 52 and 53, the actuation framework of the contact structure 416 can be seen to be retained to be movable along a vertical axis generally perpendicular to a longitudinal of, and generally the surface of, the donor reservoir 404. The actuation framework of the contact structure 416 has a distal, flat toroidal ring 444 disposed to engage and be engaged by the wall of the reservoir 404. A proximal toroidal ring 442 is maintained in parallel spaced relation to the distal toroidal ring 444 by a plurality of rod members 446, and a collar 440 is fixed to move with the proximal toroidal ring 442.

The actuation framework so formed by the toroidal rings 442 and 44, the rod members 446, and the collar 440 is extendable and retractable relative to a central column 436. An annular plate 438 is fixed along the length of the central column 436 distal to the collar 440 of the actuation framework so that the annular plate 438 retains the contact structure 416 in a floating manner. As FIG. 52 shows, the collar 440 tends to drop into contact with the annular plate 438 under the natural force of gravity when the donor reservoir 404 is filled below a given level.

The central column 436 houses a magnetic switch 414, such as a reed switch 414, and the floating actuation framework of the contact structure 416 retains a magnet 447 within the collar 440. When the actuation framework is extended as in FIG. 52 where the donor reservoir is below the state of inflation, the contacts 445 of the reed switch 414 (shown in FIG. 53) are attracted into contact with one another to complete the electrical circuit and trigger the switch 414 to an activated condition, which actuates the valve 412 to the ON condition where oxygen is permitted to flow from the oxygen source 406 to the reservoir 404. When the reservoir 404 is filled to the predetermined state of inflation, the magnet 447 within the collar 440 is moved away from the contacts 445 of the reed switch 414 to break the circuit and trigger the switch 414 to a deactivated condition, which actuates the valve 412 to the OFF condition wherein oxygen is prevented from flowing from the oxygen source 406 to the reservoir 404.

By virtue of the biasing of the contact structure 416, which can be by any mechanism including gravity, a resiliently compressible or extendible member, or any combination of mechanisms, the contact structure 416 automatically moves to the activated state to actuate the flow switch 414 and the valve 412 to the ON condition to permit oxygen to flow from the oxygen source 406 to the reservoir 404 when the volume of oxygen in the donor reservoir 404 falls below the predetermined threshold value, such as below the predetermined state of inflation. When the volume of oxygen in the donor reservoir 404 reaches the predetermined threshold value, such as at or above the predetermined state of inflation, the contact structure 416 is moved by the wall of the donor reservoir 404 to the deactivated state, and the switch is disposed in the OFF condition. In the deactivated state, the valve 412 is closed to prevent the flow of preservative gas from the source 406 to the donor reservoir 404.

The donor reservoir 404 can thus be inflated, such as to or within a given range of the maximum volume of the donor reservoir 404 without over-inflation or pressurization of the donor reservoir 404. Oxygen within the donor reservoir 404 is thus prevented from exceeding approximately ambient pressure. Except as might otherwise be required by the claims, however, embodiments of the invention could calibrate the contact structure 416 or the flow switch 414 or both to be induced to the deactivated state at some other predetermined inflation condition or pressure, including potentially a pressure or inflation condition in excess of ambient pressure or to some inflation condition well below the maximum volume of the donor reservoir 404. The flow switch 414 and the valve 412 can be electrical, mechanical, electro-mechanical, or otherwise configured and constructed.

Figure 63:
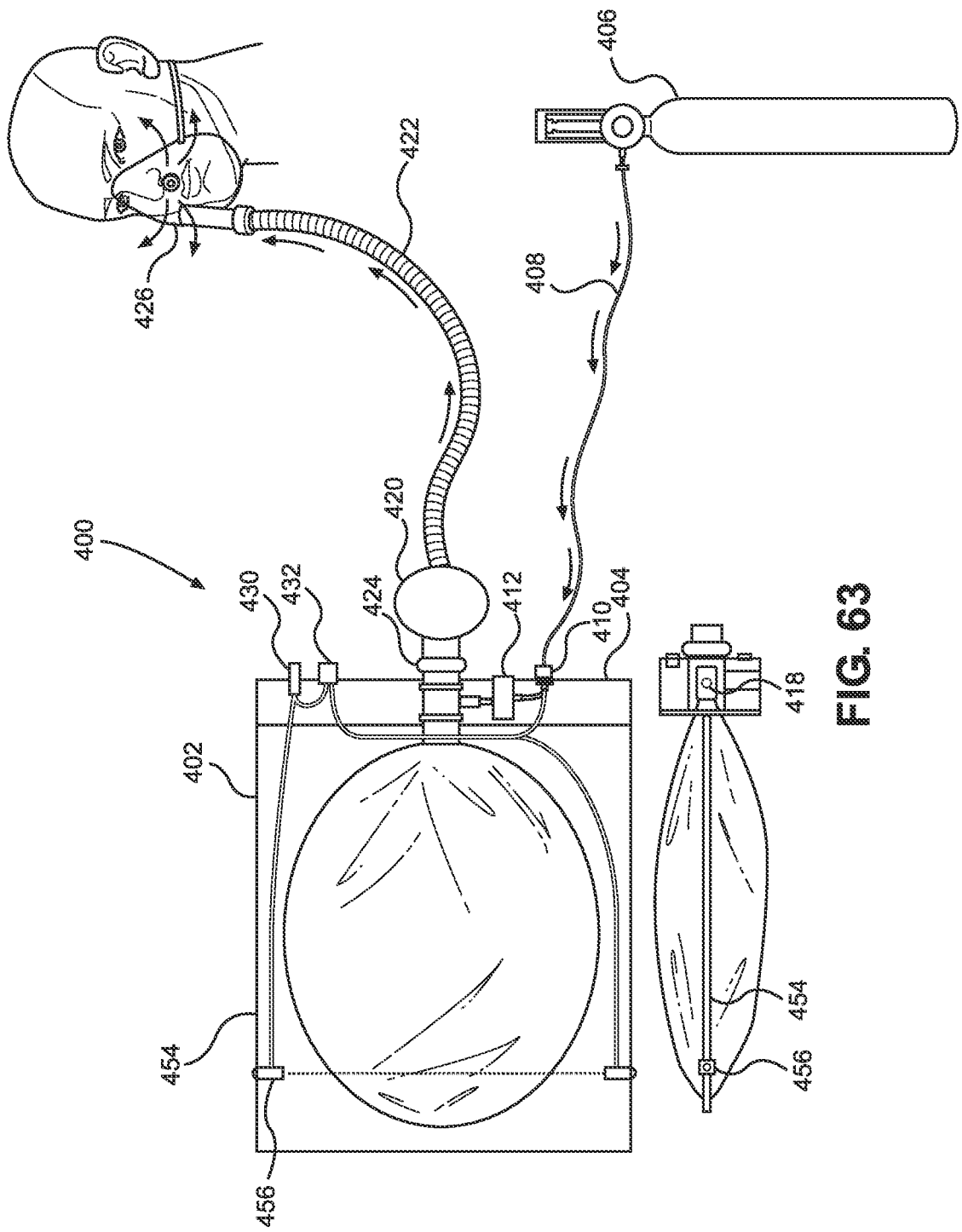
FIG. 63 comprises schematic top plan and side elevation views of still another automatic system for the conservation of gas according to the invention.

It will again be observed that one skilled in the art would appreciate other mechanisms that would operate as inflation detection systems to detect when the donor reservoir 404 is inflated to the predetermined state of inflation with each such mechanism being within the scope of the invention except as it may be expressly limited by the claims. For instance, as in the embodiment of FIG. 63, for instance, the inflation detection system could alternatively take the form of a contactless detection system 456, such as an optical detection system that could be carried forth by, for instance, a laser detection system, a camera system, an infrared inflation detection system, or any other effective optical or contactless detection system. In the non-limiting embodiment of FIG. 63, for example, a contactless detection system 456 is formed with a light emitter, such as a laser or other light emitter, retained to one side of the reservoir 404 and a light receptor disposed to the opposite side of the reservoir 404. Under such constructions, the inflation condition of the donor reservoir 404 can be sensed in a contactless manner, such as where the donor reservoir 404 is inflated to a condition where the reservoir 404 prevents the communication of light from the light emitter to the light receptor, where the reservoir 404 demonstrates a predetermined reflectance value, or in some other contactless manner.

In the embodiments of the automatic gas conservation system 400 of FIGS. 46 through 61, the supply valve 412 comprises a solenoid valve that is in electrical communication, such as through electrical wiring in an electrical circuit, with the flow switch 414. As illustrated, an electrical control system, which can include electrical circuitry, electronic memory, wiring, and other electrical control and connection components, cooperates with the inflation detection system to induce the solenoid supply valve 412 to an open condition to permit the flow of oxygen from the source 406 when the flow switch 414 is in the activated state. The electrical control system can receive power from a power source, which could be a source of alternating current through a power supply connection 430, a source of direct current such as a battery power source, or some other source of electric power. The flow of electrical power from the power source can be controlled by a power switch 432. The solenoid valve 412 is induced by the inflation detection system and the electrical control system to a closed condition to prevent the flow of oxygen from the source 406 to the reservoir 404 when the flow switch 414 is in the deactivated state. Each of the components referenced herein can be further combined or separated within the scope of the invention.

The solenoid valve 412 can be electrically opened when the electrical circuit is closed by the movement or other actuation of the flow switch 414 of the inflation detection system to the activated condition. The solenoid valve 412 is automatically closed to prevent further filling of the donor reservoir 404 when the electrical circuit is opened by the contact structure 416 and the flow switch 414 is moved to the deactivated condition, which can be indicative that the donor reservoir 404 is filled to the predetermined state of inflation. In the example of the invention where the contact structure 416 and the flow switch 414 are actuated by a pressing or pushing of the contact structure 416 outwardly by the reservoir 404, an open electrical circuit is established where no electricity flows when the contact structure 416 is sufficiently pressed outwardly by the reservoir 404 and the solenoid valve 412 is in a closed position. When the contact structure 416 is sufficiently advanced, such as by extension inwardly toward the reservoir 404, indicating that the reservoir 404 has fallen below the predetermined state of inflation, the electrical circuit is closed to permit the flow of electricity to actuate the solenoid valve 412 to an open condition so that oxygen can flow to fill the donor reservoir 404.

Even when the valve 412 is in an open condition, the rate of flow, the pressure of flow, or both the pressure and rate of flow of oxygen from the source 406 to the donor reservoir 404 can be limited, such as by a flow-limiting connector 415 as shown, for instance, in FIG. 46. The flow-limiting connector 415 could limit the flow rate of oxygen from the source 406 to the donor reservoir 404 to a predetermined flow rate, such as less than 1 liter per minute or any other flow rate. The flow-limiting connector 415 could, for example, comprise a narrow-diameter tube connector, such as a connector having an inner diameter of 0.02 mm or some other dimension reduced as compared to other conduit connections within the fluidic system. Rapid changes in pressure within the donor reservoir 404 can thus be prevented on opening of the valve 412.

Figure 47:
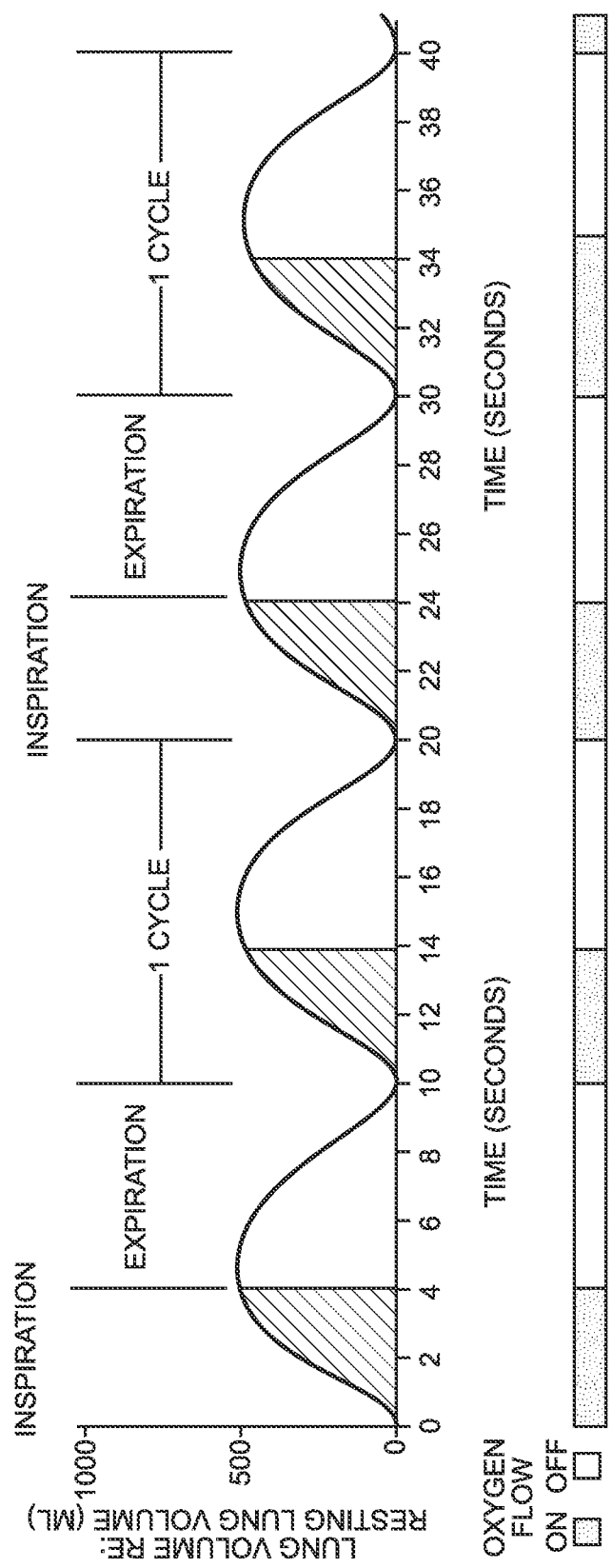
FIG. 47 is a schematic view depicting a series of respiratory cycles employing the automatic system for the conservation of gas as disclosed herein.
Figure 47:
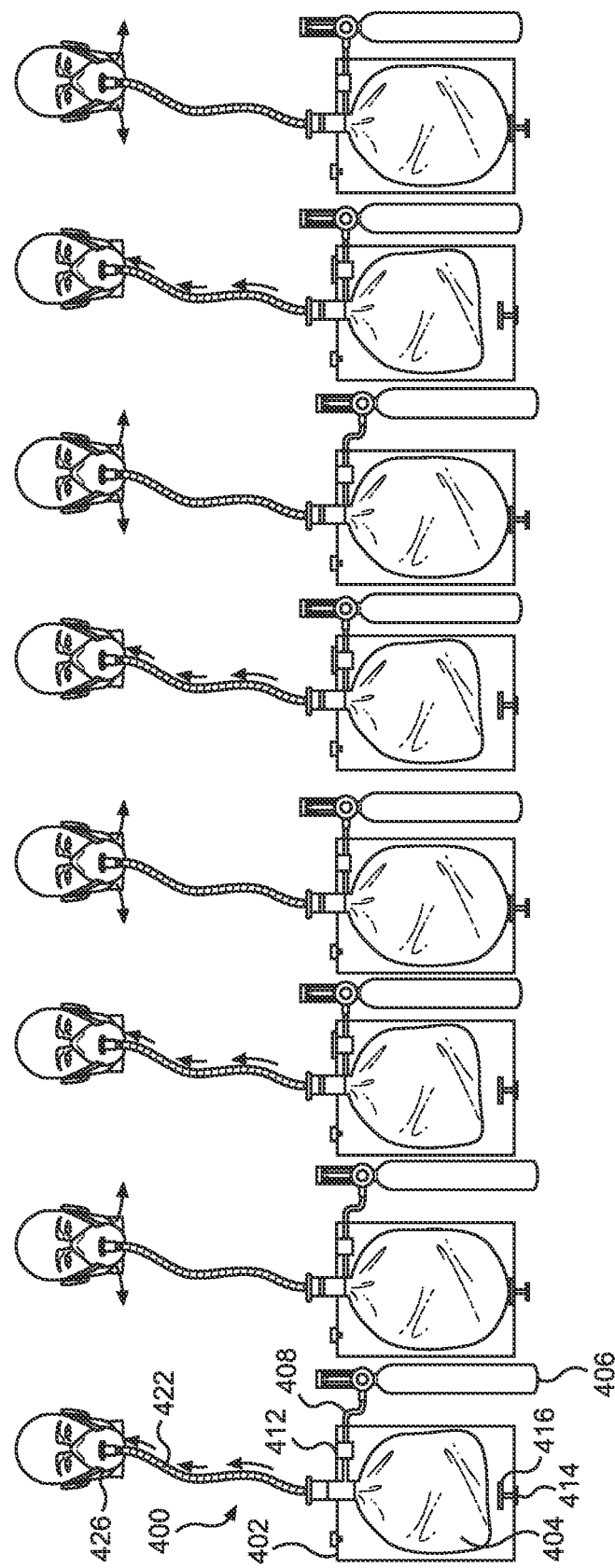
Figure 48:
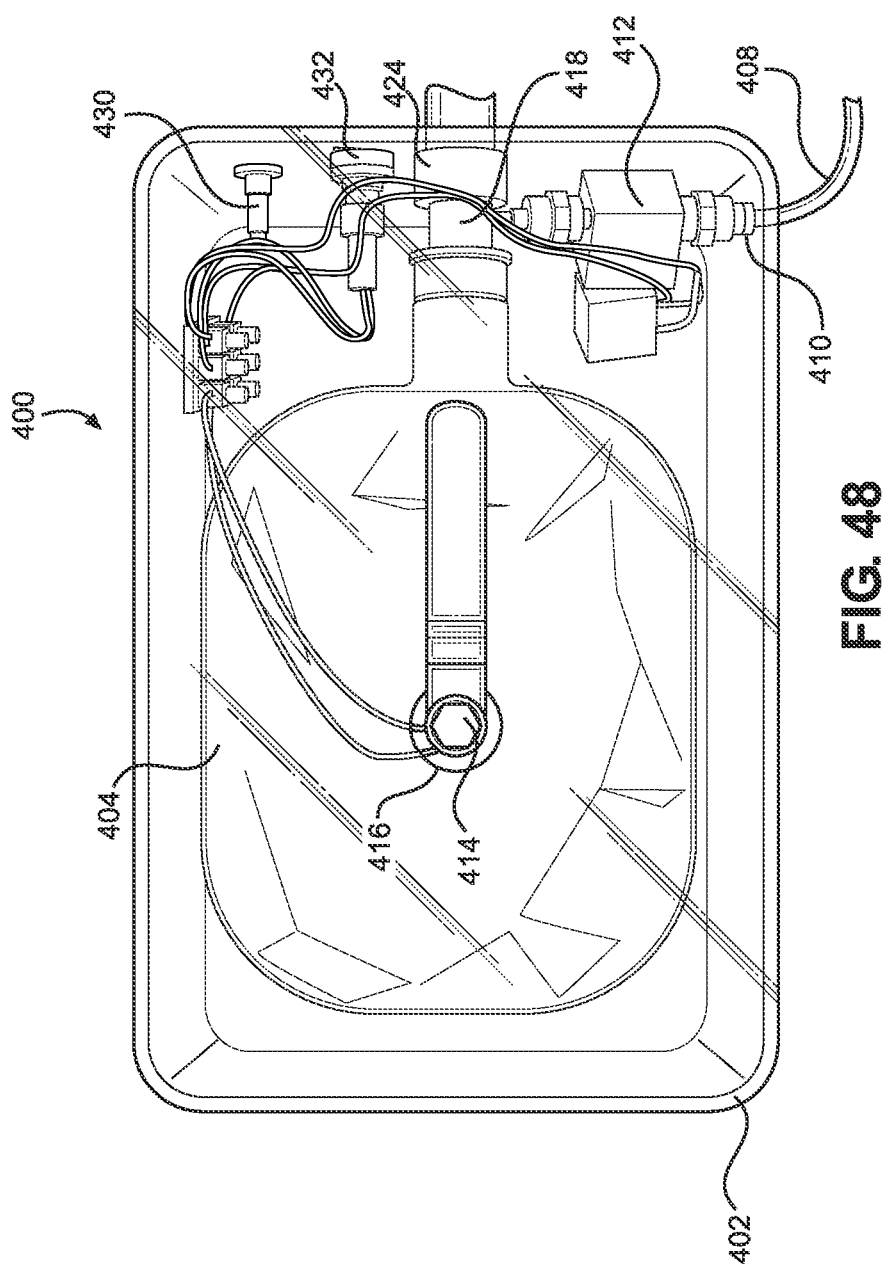
FIG. 48 is a top plan view of an alternative embodiment of the automatic system for the conservation of gas.
Figure 49:
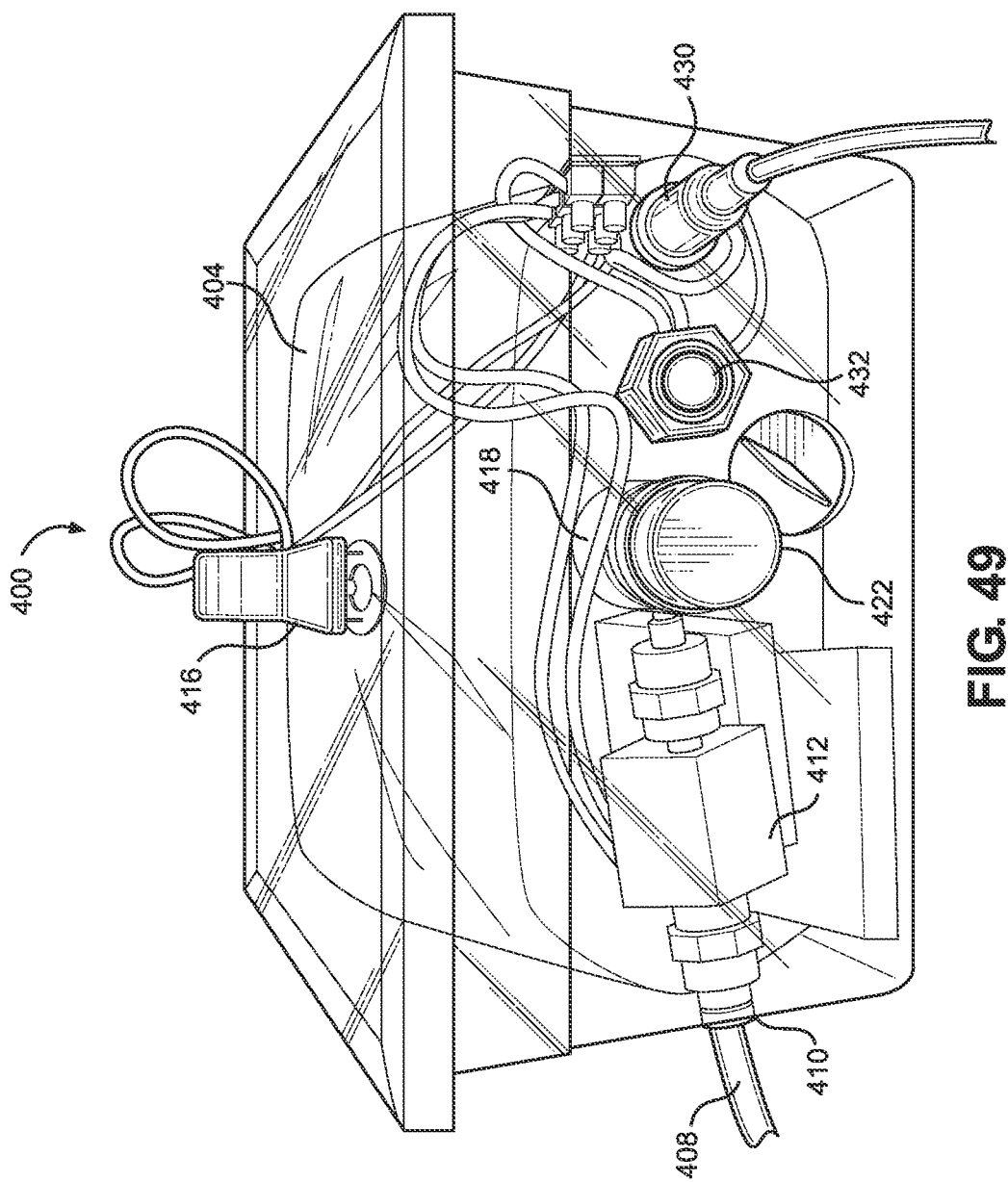
FIG. 49 is a view in front elevation of the automatic system for the conservation of gas of FIG. 48.
Figure 50:
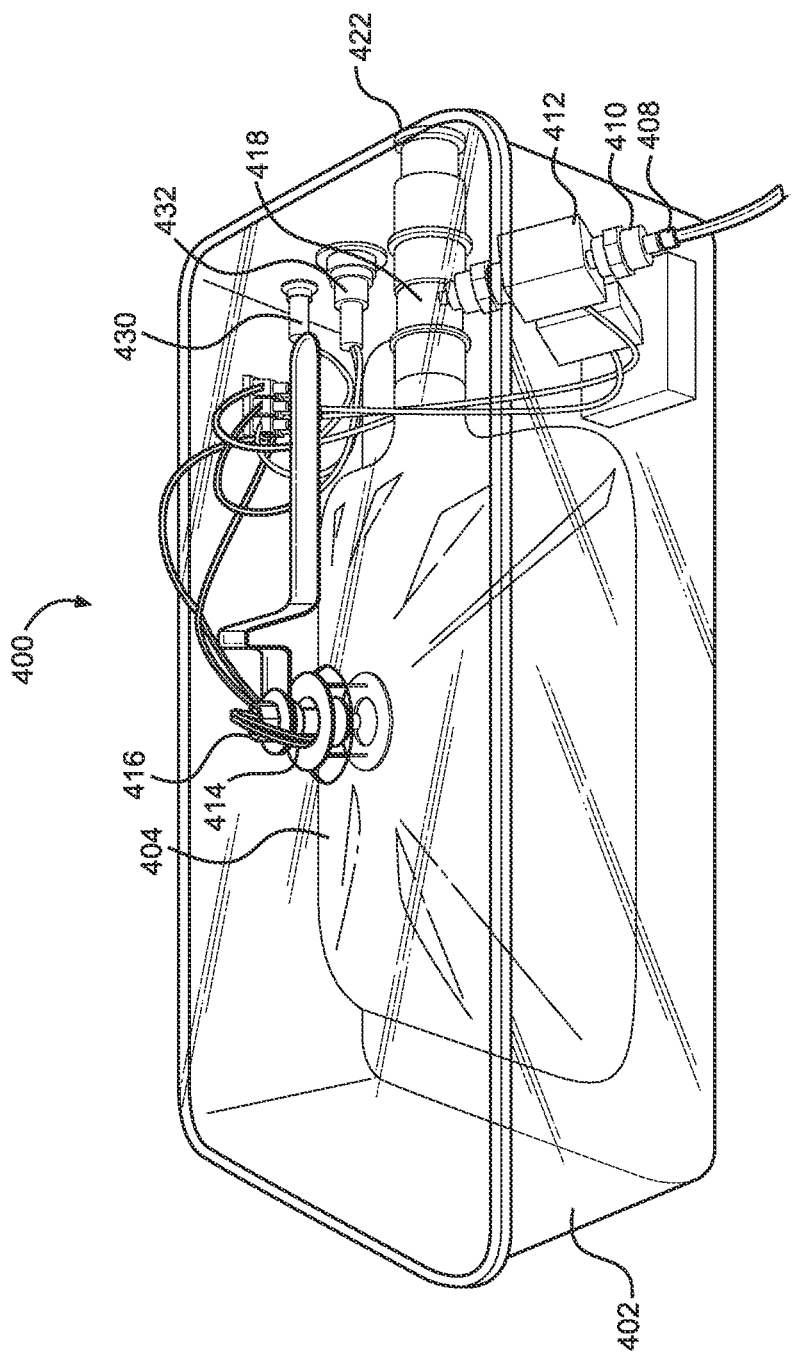
FIG. 50 is a lateral perspective view of the automatic system for the conservation of gas of FIG. 48.
Figure 51:
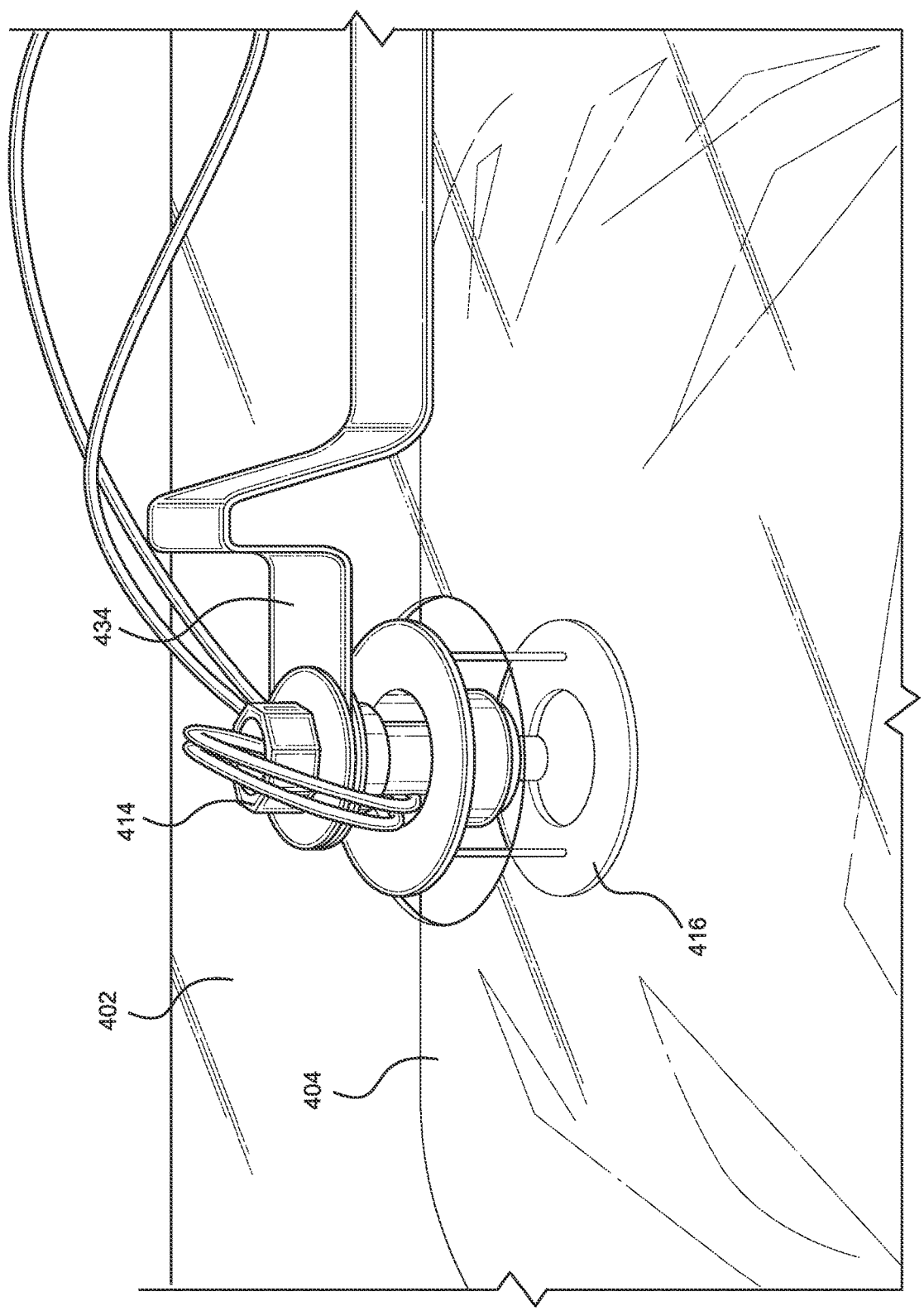
FIG. 51 is an upper perspective view of an inflation detection system for the automatic system for the conservation of gas in an ON condition.

Referring to FIG. 47, the automatic gas conservation system 400 is depicted in operation during a series of respiratory cycles to provide an on-demand supply to a recipient 426, such as a mask worn by a patient in need. In operation of the automatic gas conservation system 400, inspiration by the patient will operate to draw oxygen at ambient pressure from the donor reservoir 404 thereby tending to contract the reservoir 404. When the reservoir 404 falls between the predetermined state of inflation, the reservoir 404 is automatically filled to the predetermined state of inflation by a supply of oxygen from the source 406. A volume of continually-replenished oxygen at ambient pressure is thus available within the reservoir 404 to be drawn through the one-way inspiratory valve 424 and the ambient pressure tubing 422 during a natural inspiration phase of a breathing cycle. When the recipient 426 is not engaged in inspiration, no oxygen is drawn from the reservoir 404. When the volume of oxygen within the reservoir 404 falls below the predetermined state of inflation, the inflation detection system formed by the contact structure 416 and the flow switch 414 will detect the same and trigger the valve 412 to an open condition. Flow of oxygen is then permitted from the oxygen source 406 so that the donor reservoir 404 will be filled with oxygen until the predetermined state of inflation is reached. When the predetermined state of inflation is reached, the inflation detection system will detect the same and trigger the valve 412 to a closed condition to prevent the further supply of oxygen to the donor reservoir 404 from the source 406 until a further inspiration phase of a breathing cycle draws a volume of oxygen from the reservoir 404. The donor reservoir 404 is thus automatically supplied with oxygen while pressurization of the oxygen in the reservoir 404 is automatically prevented. Supplemental oxygen is safely and effectively supplied to the patient at ambient pressure in an on-demand volumetric displacement system enabling the transfer of oxygen during the entire inspiratory phase of the breathing cycle while the wasteful release of oxygen during the expiratory phase of breathing, indeed at any phase other than the inspiratory phase, is prevented.

The donor reservoir 404 automatically receives replenishing oxygen from the pressurized source 406 through the high-pressure tubing 408 and through the supply valve 412 as soon as the reservoir 404 begins to collapse. The automatic refilling of the reservoir 404 ensures that the donor reservoir 404 always retains a supply of oxygen available for the next inspiratory phase of the breathing cycle while the oxygen in the reservoir 404 never exceeds ambient pressure. Where the donor reservoir 404 is visually exposed, such as through a partially or completely transparent housing 402 or an observation aperture in the housing 402, an observer is provided with visual confirmation of the state of inflation of the donor reservoir 404. The automatic gas conservation system 400 can thus provide a synchronized delivery of supplemental oxygen to a recipient 426 as the donor reservoir 404 and the system 400 in general synchronize with the physiological ventilations of a patient based on the storage and replenishment of oxygen in the donor reservoir 404 at ambient pressure and the termination of the supply of oxygen automatically on the donor reservoir 404 reaching the predetermined state of inflation.

Within the scope of the invention, the system 400 can measure, record, and analyze the flow of oxygen and the breathing characteristics of a patient. By way of non-limiting example, a volumetric measuring flow meter could be connected to the source 406 of oxygen. Additionally or alternatively, one or more flow meters could be retained within the housing 402 along the path of gaseous flow through the system 400. For instance, a flow meter could be disposed to measure oxygen passing through the valve 412. The valve 412 can incorporate a flow meter, or a flow meter could be otherwise disposed. For instance, a flow meter could further or alternatively be disposed between the reservoir 404 and the ambient pressure tubing 422. By measuring the volume of oxygen supplied to a recipient 426 by the system 400, such as over a given time period, per cycle of inspiration and expiration, or otherwise, plural determinations, measurements, and analyses can be made. For instance, one can determine the volume of oxygen inspired by the patient and, additionally or alternatively, the volume of oxygen remaining in the oxygen source 406. Through electronic memory and software operating on the electrical system or in communication therewith, the system 400 can harvest, process, and analyze data based on usage of the system 400.

As often shown and described herein, the recipient 426 can be the breathing mask of a patient receiving supplemental oxygen, but other recipients and delivery equipment are possible and within the scope of the invention. When worn by a patient, the patient and the breathing mask or other oxygen delivery equipment may collectively be referred to as the recipient 426. Other recipient delivery equipment could, for example, comprise other respiratory accessories, such as but not limited to nasal cannulas, laryngeal mask airways (LMA), endotracheal tubes, tracheostomys, ventilator attachments, CPAP machine connectors, Ambu bags, or even delivery devices for recreational oxygen. The automatic gas conservation system 400 is not limited with respect to the recipient 426 unless the claims expressly so require.

As shown in FIG. 46, a recipient mask 426 can have one or more one-way expiratory valves 428 and can include adjustment mechanisms as is known to the art for adjusting oxygen supply to the patient. As necessary, the concentration of oxygen that the patient needs as determined by the physician can be reliably and predictably diluted and controlled with devices currently in use and that are within the scope of the system 400. By way of example and not limitation, the number, diameter, or other characteristic of orifices in the inspiration tube 422 or the recipient mask 426 can be adjusted to allow more or less oxygen to achieve the desired concentration to the recipient mask 426 for the patient as clinically needed.

With further reference to FIG. 47, the necessary supply of oxygen to a patient recipient 426 and the synchronized operation of the automatic gas conservation system 400 in relation thereto can be further understood. There, the dynamics of the breathing cycle are depicted in parallel with the filling and refilling operations of the donor reservoir 404 of the automatic gas conservation system 400. To expand the lungs, the inspiratory muscles overcome two key factors, namely, compliance of the lungs and airway resistance mainly in the form of frictional resistance to the flow of air through the airways. At the start of inspiration, the diaphragm contracts and descends, expanding the thoracic volume. The descent of the diaphragm compresses the abdominal contents and decompresses the contents of the thoracic cavity. With expansion of the thoracic cavity and its decompression, both intrapleural pressure and alveolar pressure decrease. Alveolar pressure decreases to a sub-atmospheric level, and the pressure gradient for the flow of air into the lungs is established. Air flows into the lungs and lung volume increases until the alveolar pressure rises to the atmospheric level (0 cm $H_2O$) when the pressure gradient for flow of air into the lungs ceases to exist. At the end of quiet inspiration, intrapleural pressure reaches about −8 cm $H_2O$, and the transpulmonary pressure distending the lungs increases to 8 cm $H_2O$ (Pl=Pa−Ppl=0−(−8)=8 cm $H_2O$)

During quiet expiration, the cycle is reversed. The inspiratory muscles relax, and the inward elastic recoil of the lungs results in deflation of the lungs. During deflation, the lungs and chest wall move as one unit. Airflow out of the lungs ceases when alveolar pressure equals atmospheric or ambient pressure (0 cm $H_2O$).

Based on Boyle's law, in a closed system where the number of gas molecules is constant, at any constant temperature, the pressure exerted by a gas varies inversely with the volume of the gas. Therefore, as the volume of a gas increases, the pressure exerted by the gas decreases. Conversely, the pressure increases as the volume decreases.

Accordingly, in operation of the present system 400, when a patient takes a breath during the inspiratory phase of the breathing cycle, a continuous flow of supplemental oxygen enters the patient's lungs from the system 400 throughout the entire inspiratory phase of the breathing cycle. The flow rates, pressures, and volumes are different at different points of the inspiratory phase. The flow starts by a drop in alveolar pressure below ambient pressure inside the donor reservoir 404 with it being again recognized that the system 400 could work with higher and lower pressures than ambient unless the claims require otherwise. Then, the donor reservoir 404 supplies non-pressurized oxygen at ambient pressure directly to the patient through the recipient 426 as a continuous flow but at different speeds during the inspiratory cycle. The flow rates, pressures, volumes, and respiratory rate are closely synchronized to those of the patient due to the donor reservoir 404 being maintained at ambient pressure. Having a system 400 that matches the supplement of oxygen to a patient's physiological ventilation values at each point in time throughout the inspiratory phase of the breathing cycle ensures reliable delivery of the prescribed oxygen concentration through a recipient facemask 426 or any other oxygen delivery equipment available without supplementing less or more oxygen flow than planned. Flow rate, alveolar pressure, and tidal volume can be synchronized at each point throughout the inspiratory phase of the breathing cycle with it being recognized that the physiological ventilation values of patients are different at different points in the inspiratory phase.

The continuous flow of oxygen towards the patient's lungs is sustained until the patient's intrathoracic pressure is at equilibrium with the ambient pressure of the donor reservoir 404 at the end of the inspiratory phase of the breathing cycle. At that time, the flow of oxygen to the patient stops until the beginning of the next inspiratory phase. No oxygen flows from the system 400 to the patient during the expiratory phase of the breathing cycle, but a flow of oxygen from the source 406 of compressed, high-pressure oxygen is supplied to the cause the donor reservoir 404 to expand until the predetermined state of inflation is reached. Once the reservoir 404 is refilled to the predetermined state of inflation and at ambient pressure, the donor oxygen reservoir 404 is ready to supply supplemental oxygen when the patient's next inspiratory phase begins. The inflation detection system automatically shuts off the supply valve 412 to prevent further oxygen flow once the reservoir 404 is full and at ambient pressure. The passive and sustained transfer of a reliable volume and concentration of supplemental oxygen from the donor reservoir 404 to the patient's lungs throughout the entire inspiratory cycle is possible with the donor reservoir 404 placed between a compressed oxygen source 406 and the patient's oxygen delivery equipment, such as a recipient mask 426.

The automatic gas conservation system 400 can thus be employed to provide supplemental oxygen to patients in a wide variety of circumstances. Furthermore, except as the claims may be expressly limited, the automatic gas conservation system 400 is not limited to handling oxygen, and it is not necessarily limited to providing gas to patients at all. Other applications where the dispensing of gas or other substances with automatic replenishment of the reservoir 404 are possible.

Many conditions may require supplemental oxygen. For instance, at the writing of the present document, many thousands of patients require supplemental oxygen due to acute hypoxemic respiratory failure deriving from the COVID-19 coronavirus disease. Other illnesses requiring supplemental oxygen include acute exacerbations of chronic obstructive pulmonary disease (COPD) and acute severe bronchial asthma. Patients with chronic obstructive pulmonary disease often have chronic hypoxaemia with or without $CO_2$ retention. Oxygen in this situation is required until the exacerbation is settled. While a high $FiO_2$ of up to 100% can be initially administered in case hypoxemia is severe, it is soon tapered to around 50-60% $FiO_2$. The goal of supplemental oxygen is to maintain a $PaO_2$ (Partial Pressure of arterial Oxygen) of 55-60 mm Hg, which corresponds to $SpO_2$ of about 90%. Higher concentrations of oxygen blunt the hypoxic ventilatory drive, which may precipitate hypoventilation and $CO_2$ retention. It is considered preferable to use a regulated flow device such as a venti mask, which guarantees oxygen delivery to a reasonable extent. Once the patient is stabilized, one can shift to nasal prongs, which are more comfortable and acceptable to most patients. Patients with acute severe asthma or status asthmaticus have severe airway obstruction and inflammation. They are generally hypoxemic. With such conditions, an arterial blood sample is immediately obtained, and oxygen is started via nasal cannula or preferably via a facemask at a flow rate of 4-6 L/min to achieve $FiO_2$ of 35 to 40%. Higher flow is unlikely to improve oxygenation. The flow rate is adjusted to maintain a PaO$_2$ of about 80 mm Hg or near normal value. Assisted ventilation is required in case there is persistence of hypoxemia and/or precipitation of hypercapnia.

These clinical samples show the importance of supplying reliable FiO$_2$ (fraction of Inspired Oxygen) to a patient. However, with conventional systems, they also require continuous flow at high flow rates to overcome air entrapment, making these systems wasteful when supplementing directly compressed oxygen from a cylinder to patients. Also, even if the systems intermittently deliver compressed oxygen only during the inspiratory phase of the breathing cycle, such as with pulse flow (PF), to avoid the continuous delivery of oxygen, these systems must provide pulses of compressed oxygen to the patient containing significant more oxygen than the patient requires to overcome air entrapment.

By providing oxygen only on demand during the inspiratory phase of the breathing cycle, the present system 400 is elegant and efficient in conserving oxygen and lowering oxygen costs without compromising necessary supply. Since there is no gas delivery to the patient during the expiratory phase of the breathing cycle, the flow of oxygen from the source 406 of compressed oxygen is intermittent during inspiration only and not a continuous flow as demanded by, for instance, high-concentration oxygen masks of the prior art to keep a reliable concentration of oxygen and to overcome air entrapment that otherwise dilutes oxygen concentration and delivers an unreliable concentration to the patient. Oxygen delivery systems using compressed oxygen at a constant flow, particularly at high flow rates, are wasteful and costly. Moreover, the delivery of pressurized oxygen can be complex and difficult, often requiring complicated software, detailed algorithms, and multiple components susceptible to malfunction and breakage thereby requiring repairs and demanding safety mechanisms that further contribute to the cost and complexity of such systems.

Thus, under typical systems of the prior art, a relatively inexpensive oxygen delivery system can be provided, but it demands the constant flow of pressurized oxygen with half or more of the precious gas being simply exhausted to the environment. Systems with oxygen delivered with pulse flow (PF) through a facemask or another oxygen delivery device do seek to supply oxygen only during the inspiratory phase and not during exhalation seeking to reduce total oxygen needs. However, that delivery demands expensive equipment and is not imparted at ambient pressure. Furthermore, providing a pulse of supplemental oxygen properly-timed to synchronize perfectly with the breathing of a patient can be difficult or impossible, particularly where patient oxygen requirements change over time.

The on-demand supply of oxygen to be naturally inspired that is provided by the donor reservoir 404 with the present automatic gas conservation system 400 overcomes numerous deficiencies and limitations exhibited by systems of the prior art. For instance, to achieve the prescribed inspired oxygen concentration, many prior art systems are dependent on the patient's peak inspiratory flow rate (PIFR). For example, when a patient requires low-inspired oxygen concentration, using a nasal cannula at a low flow rate will help, but this practice limits the patient's oxygen only to a low inspired oxygen concentration. Should the patient increase his or her oxygen requirements significantly, the inspiratory effort to drive more air into the lungs, which is dependent on tidal volume, 'speed' of inspiration, and respiratory rate, will make the PIFR exceed the flow rate at which oxygen or an oxygen/air mixture is supplied by the nasal cannula or other delivery device. This will mean that at the time of PIFR more or less entrainment of room air occurs, altering the resulting FiO2 in an unpredictable fashion. On the other hand, if high concentrations of oxygen are needed by a patient, using a non-rebreathing face mask at very high flows of oxygen (10-15 L/Min) reassures a reliable delivery of oxygen volume at the prescribe concentration and is less dependent on PIFR. However, half or more of the oxygen is wasted to the environment with supply costs being commensurately increased.

While a compressed gas tank is often depicted and referred to as the oxygen source 406 herein, other oxygen sources 406 are possible within the scope of the invention. By way of further, non-limiting examples, the automatic gas conservation system 400 can provide on-demand oxygen to patients with oxygen supplied by an oxygen concentrator. An oxygen concentrator does not require a tank. Instead, it takes in air and removes the nitrogen from it thereby leaving the oxygen-enriched gas for those patients requiring medical oxygen. The typical flow of this compressed oxygen is 1-5 liters/minute. High-end oxygen concentrators can deliver upwards of 50 L/minute, but they require more electricity and more maintenance.

By placing an automatic gas conservation system 400 as disclosed herein between the oxygen concentrator and the recipient 426, such as a patient face mask or a nasal cannula, an excess of oxygen can be stored at ambient pressure for use if, due to flow limitations, volume demands, or otherwise, sufficient supply is not provided by the concentrator. For example, if the oxygen concentrator is providing 10 L/minute and the patient suddenly needs more as his saturation level is dropping, there will be a volume of oxygen at ambient pressure available in the donor reservoir 404. Without the reservoir 404, the patient would be limited to the flow of the concentrator, which itself is limited. Therefore, without the reservoir 404, if a patient needs more oxygen to survive, the choices are to increase oxygen flow to the mask, which may be impossible, or intubate the patient and use mechanical ventilation, something which both doctor and patient want to avoid.

Where the oxygen source 406 is an oxygen concentrator, the automatic gas conservation system 400 can be placed between the oxygen concentrator and the patient mask 426 or other recipient so that, as oxygen leaves the concentrator, it enters the large reservoir 404 where it remains at ambient pressure until the patient inhales. As the patient breathes in and draws oxygen from the reservoir 404, the reservoir 404 begins to deplete, the supply valve 412 from the oxygen concentrator as the oxygen source 406 opens to replenish the reservoir 404 with compressed oxygen from the oxygen concentrator. As the patient exhales, no flow occurs between the reservoir 404 and the patient through the recipient mask 426 or otherwise. Rather than wasting the oxygen flowing from the concentrator during the exhalation phase of the patient, the flow is employed to replenish the reservoir 404. Once the reservoir 404 is full, the supply valve 412 stops the flow of oxygen from the oxygen concentrator source 406. When the patient breathes in again and the donor reservoir 404 contracts to below the predetermined state of inflation, the shut off valve 412 opens to replenish the reservoir 404 with oxygen from the oxygen concentrator, and the cycle repeats with every breath. In this manner, oxygen not taken in by the patient during inspiration is stored rather than lost. In one example, a concentrator 406 with an output of 20 L/minute used with a patient needing only about 5 liters of highly concentrated oxygen during inhalation leaves 10 liters or more that could extend supply availability. Oxygen concentrators can thus be used for their intended purpose while having fewer demands with respect to work hours, electricity, wear and tear, and repairs thereby representing a more useful and reliable investment for the end user. Also, the system 400 and the concentrator as the oxygen source 406 cooperate to provide more reliable concentrations of oxygen to patients that require higher concentrations.

As disclosed herein, the automatic gas conservation system 400 provides a gas, or a mixture of gases, from the donor reservoir 404 to the recipient 426 at ambient pressure. The gas or a mixture of gases at ambient pressure within the reservoir 404 can be drawn from the donor reservoir 404 when the recipient 426 drops its pressure below that of the donor reservoir 404, and the drawing of ambient pressure gas from the reservoir 404 stops immediately once the pressure of the recipient 426 equilibrates with that of the reservoir 404. The system 400 can provide a gas or a mixture of gases from the donor reservoir 404 to the recipient 426 at ambient pressure, and the percentage of gases in the mix reaching the recipient 426 can be regulated, such as by the resistance placed in the conduit of each gas involved in the mixture at ambient pressure.

The system 400 conserves gas from one or more sources 406 by limiting the flow of a continuous pressurized gas or gasses to only when a recipient 426 creates the need for the gas or gases by dropping its pressure below the ambient pressure of the donor reservoir 404. The donor reservoir 404 is thus capable of passively permitting the transfer of a gas or gasses from an ambient pressure reservoir 404 by making the gas or gasses available to the recipient 426 in a manner that matches the exact volume and speed of the demand based on the control of the pressure difference by the recipient 426. In embodiments of the system 400, the donor reservoir 404 is not only at ambient pressure but it is also large enough to accommodate the transfer in a completely passive way and without resistance of the volume of gas or gasses in a 1:1 ratio at every point in time during the transfer from the beginning to the end of the flow created by the pressure difference between the recipient 426 and the donor reservoir 404, such as an inhalation phase during the respiratory cycle. In practices of the system 400, diagrams of the speed, pressure, time, and volume of patient inspiration and gaseous transfer from the donor reservoir 404 are equivalent and will likely be substantial mirror images. The drop in pressure of the recipient 426, such as during inhalation, is entirely used for the transfer of volume from the reservoir 404. No extra pressure is required to open a pressure check valve to start the flow as would be the case with a chamber or reservoir containing oxygen at a higher pressure than ambient pressure. The system 400 can work as a closed system, or it can be open to ambient pressure of the environment while being maintained at ambient pressure. The system 400 conserves gas or gases by limiting the flow of the gas or gases to the recipient 426 only when needed. Since a patient intakes supplemental oxygen flowing to their recipient mask 426 only during inspiration, a far reduced volume of oxygen is required, such as one-half to one-third, as compared to continuous flow systems.

In practices of the invention, the system 400 can be used as a source to provide variable oxygen concentrations for CPAP machines used in the treatment of sleep apnea and COPD. The system 400 can help conserve oxygen from the pressurized source 406 by, for example, connecting the system 400 to the air input of the CPAP machine. The system 400 can also be employed to provide a reservoir 404 at ambient pressure for oxygen concentrators so patients can inhale or inspire a more reliable concentration of oxygen at ambient pressure, especially when high flows are demanded to treat a patient with respiratory insufficiency. Moreover, the system 400 can help oxygen concentrators as sources 406 of oxygen to provide the same oxygen concentration of oxygen to a patient with less required flow of oxygen, decreased hours of operation, reduced electricity consumption, increased longevity to the machine, and fewer repairs and parts. Still further, with the gas conserved, oxygen concentrators that previously supplied just one patient could potentially be used for plural patients concomitantly depending on the required supply rates.

Returning to the volumetric displacement preservation system of what is now disclosed and protected by U.S. Pat. Nos. 9,272,834 and 10,233,068, a volumetric displacement preservation system 10 is depicted in use in FIG. 1 dispensing a volume of liquid 202 from a storage vessel 200 with an open inner volume containing the liquid 202 into a recipient vessel 204 for consumption or use. In the present example, the storage vessel 200 is a wine bottle 200, the retained liquid 202 is wine 202, and the recipient vessel 204 is a wine glass 204. However, it will be understood that the invention is not so limited. While wine and similar comestible liquids may be well served by use of the disclosed preservation system 10, numerous other applications will be obvious in view of the present disclosure, each being within the scope of the invention except as it might expressly be limited by the claims.

The storage vessel 200 has an open inner volume that is initially sealed, in the instance of a wine bottle 200 by a cork, to protect against spoilage. Once the storage vessel 200 is opened to cause exposure to oxygen-rich air, spoilage begins. As more of the liquid 202 is poured from the vessel 200, more air enters the inner volume of the vessel 200, and spoilage is accelerated. The preservation system 10 operates to minimize or, ideally, to eliminate that spoilage by preventing the entry of air into the inner volume as the liquid 202 is exhausted and instead insulating the liquid 202 against degradation by the replacement of the exhausted liquid 202 with a preservative gas, such as an inert gas, by volumetric displacement. Any type of preservative gas could be used within the scope of the invention except as it might be limited by the claims. For instance, the preservative gas could be nitrogen, argon, another preservative gas, or some combination thereof, subject perhaps to potential impurities. A volume of preservative gas is retained external to the vessel 200, potentially at approximately atmospheric pressure. For instance, the preservative gas can be retained in a collapsible or compressible vessel or a vessel otherwise reducible in open inner volume.

During dispensing of the liquid 202, an open fluidic inlet pathway is selectively provided between the volume of preservative gas external to the vessel 200 and the inner volume of the vessel 200 while a separate open fluidic exhaust pathway is provided for dispensing the liquid 202. With the fluidic pathways open, liquid 202 exhausted through the exhaust pathway will naturally draw in and be replaced by preservative gas passed through the inlet pathway. The inner volume of the vessel 200 will thus be occupied by the remainder of the volume of liquid 202 in the vessel 200 and the preservative gas received in exchange for the dispensed liquid 202. When a given volume of liquid 202 has been dispensed, the inlet and exhaust pathways can be closed to exclude the introduction of environmental air and to maintain the gaseous content of the inner volume of the vessel 200 ideally substantially or entirely consisting of the preservative gas, subject potentially to the volume of air, if any, present in the inner volume on initial installation of the volumetric displacement preservation system 10. The foregoing could be carried forth under a plurality of constructions within the scope of the invention.

Figure 1:
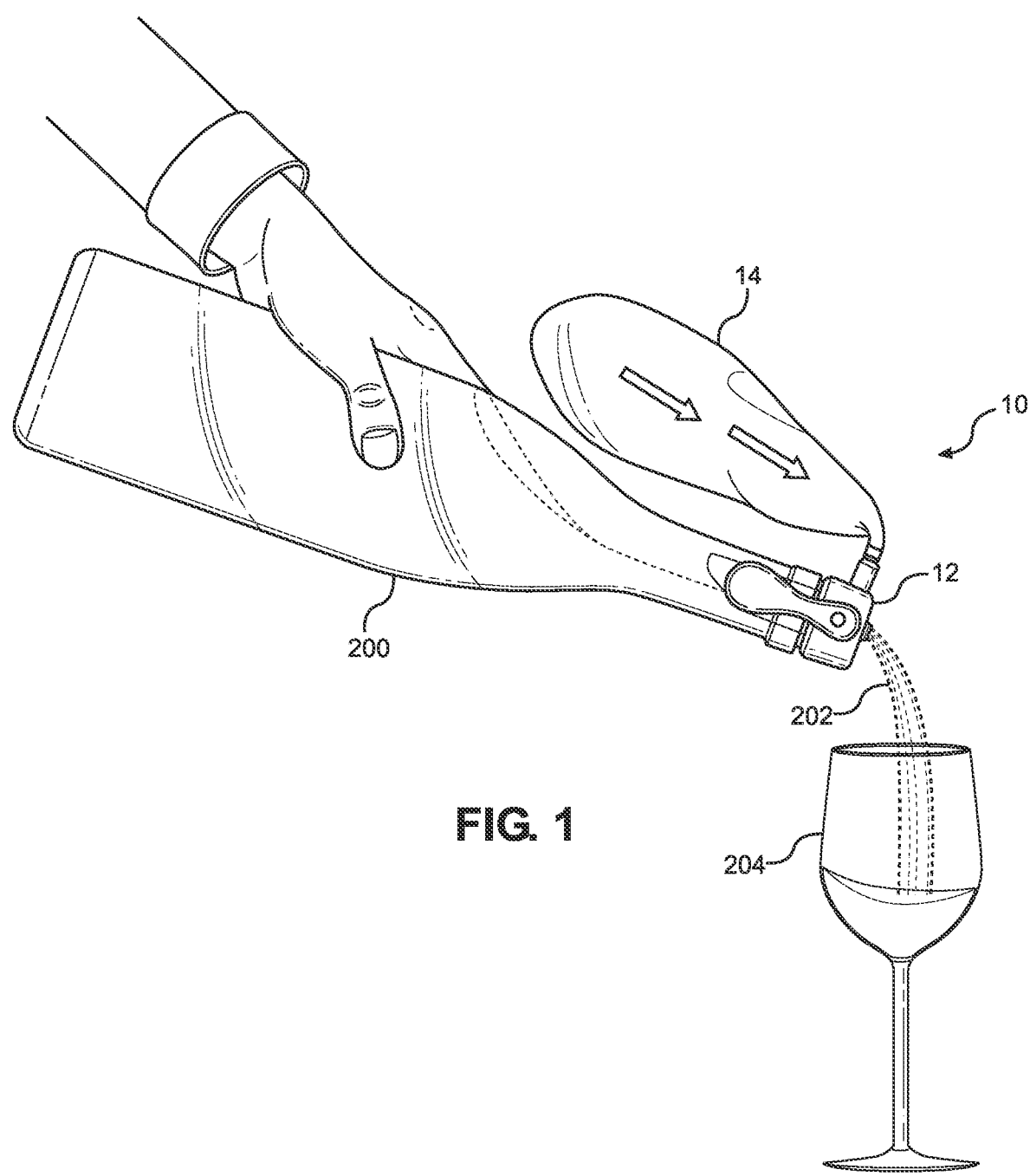
FIG. 1 is a view in front elevation of an embodiment of the volumetric displacement preservation system in use dispensing a volume of liquid from a vessel.

In the embodiment first illustrated in FIG. 1 and then in greater detail in FIGS. 2A through 3B, the volumetric displacement preservation system 10 has a fluid exchange structure 12 that selectively and, potentially in a substantially simultaneous event, establishes and closes the above-described inlet and exhaust pathways. The fluid exchange structure 12 has a stopper 16 with a plurality of annular sealing ridges 22 therealong that cooperate to create a sealing engagement with the vessel 200, in this case with the neck 206 of the wine bottle 200, and a head portion 18 accessible from external to the vessel 200. While separate valves could be provided within the scope of the invention for opening and closing the inlet and exhaust pathways, the depicted preservation system 10 provides a fluid exchange valve 32 that has a first condition, depicted in FIGS. 2A and 2B, wherein the inlet and exhaust pathways are substantially sealed and a second condition, depicted in FIGS. 3A and 3B, wherein the inlet and exhaust pathways are opened.

The stopper 16 and the head portion 18 are shown as a unitary member, but it is possible for them to be separately formed. The stopper 16, the head portion 18, and the fluid exchange valve 32 could be formed from any suitable material or materials. In one contemplated embodiment, the fluid exchange valve 32 could be made from a rigid material, such as a metal. The stopper 16 and the head portion 18 could be formed from a more flexible and resilient material, such as a polymer. By way of example and not limitation, the fluid exchange valve 32 could be crafted from stainless steel while the stopper 16 and the head 18 could be formed from silicone.

Figure 15:
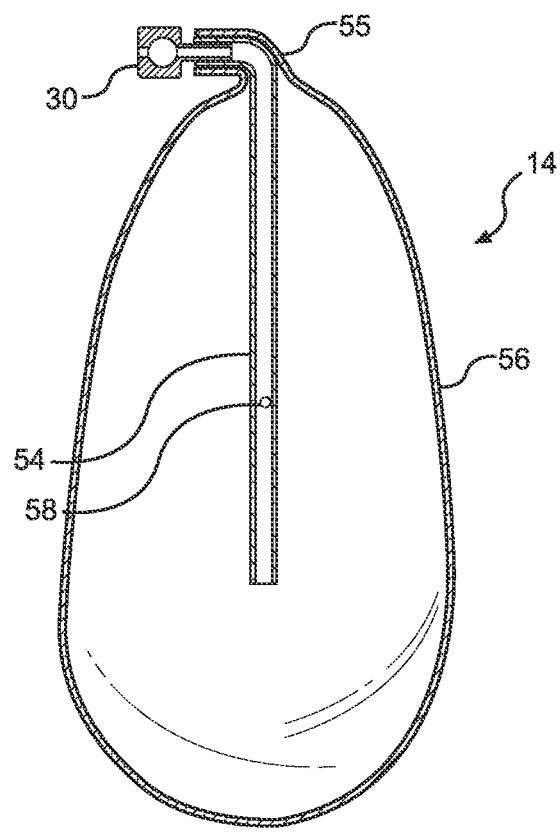
FIG. 15 is a cross-sectional view of an external preservative supply bladder according to the invention.
Figure 16:
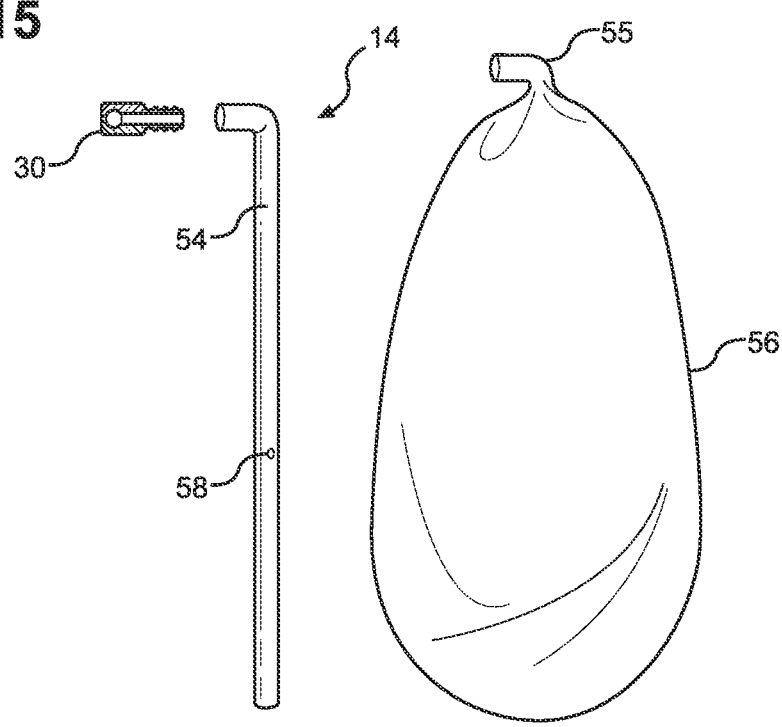
FIG. 16 is an exploded view in front elevation of the external preservative supply bladder according to the invention.

Preservative gas is supplied to the inner volume of the vessel 200 through the inlet pathway during a dispensing of liquid 202 from an expandable and compressible bladder 14, which is shown in cross-sectional and exploded views in FIGS. 15 and 16. There, the bladder 14 can be seen to have a shell 56, which can be of a flexible and substantially gas impermeable material. Numerous such materials are possible, each within the scope of the invention. In one embodiment, for example, the shell 56 of the bladder 14 can be a polymeric material with or without a lining layer. The material defining the shell 56 could, for example, comprise a foil formed by one or more layers of polymeric material with an aluminum lining. The shell 56 can be sealed but for an orifice 55. A tube structure 54 with an elongate portion within the shell 56 and a lateral portion that is received by the orifice 55 is sealingly engaged with the valve coupling 30. One or more apertures 58 can be disposed along the tube structure 54 to facilitate gas flow. The valve coupling 30 can have an automatically sealed condition when not engaged with the valve coupling 28 of the fluid exchange structure 12 and an automatically bidirectionally open condition when engaged with the valve coupling 28. The inner volume of the bladder 14 can vary depending on, among other things, the intended application. In certain practices of the invention, the bladder 14 can have an inner volume corresponding to the inner volume of the vessel 200 or the volume of the liquid 202 retained therein.

As shown, for instance, in FIGS. 7 through 10, the fluid exchange valve 32 has a base portion 34 and a dispensing nozzle 36 that projects from the base portion 34. In this embodiment, the base portion 34 is barrel, round, or rod shaped, and the dispensing nozzle 36 projects orthogonally from a central portion of the barrel-shaped base portion 34. The base portion 34 has first and second conduit joining passageways 48A and 48B, each with an opening to the dispensing nozzle 36 and an opening along the outer surface of the base portion 34 opposite to the nozzle 36. As shown most clearly in FIGS. 7 through 10, the openings of the conduit joining passageways 48A and 48B along the outer surface of the base portion 34 are disposed in opposed outboard positions from a centerline established by the nozzle 36.

A conduit joining channel 46 is disposed in the outer surface of the base portion 34 of the fluid exchange valve 32. In this embodiment, the conduit joining channel 46 is disposed along a tangent to a mid-portion of the base portion 34 in substantial alignment with the nozzle 36 and along a path generally parallel to the paths of the conduit joining passageways 48A and 48B. The conduit joining passageways 48A and 48B thus have portions thereof disposed outboard of the conduit joining channel 46. The conduit joining channel 46 thus represents a central groove across and tangent to the barrel-shaped base portion 34 while the first and second conduit joining passageways 48A and 48B join together to meet and establish a fluidic pathway with the dispensing nozzle 36, including within the inner volume of the base portion 34 underlying the wall portion in which the conduit joining channel 46 is formed.

The fluid exchange valve 32 is pivotably retained by the head portion 18 of the fluid exchange structure 12 with the barrel-shaped base portion 34 received in a correspondingly shaped and sized valve barrel pathway 52 that communicates laterally within the head portion 18 and with the nozzle 36 pivotable within an elbow-shaped valve positioning pathway 50. With the base portion 34 rotatable within the valve barrel pathway 52, the fluid exchange valve 32 can be pivoted from a first, closed position with the dispensing nozzle 36 orthogonal to a longitudinal axis of the stopper 16 and a second, open position with the dispensing nozzle 36 in line with the longitudinal axis of the stopper 16.

Figure 14:
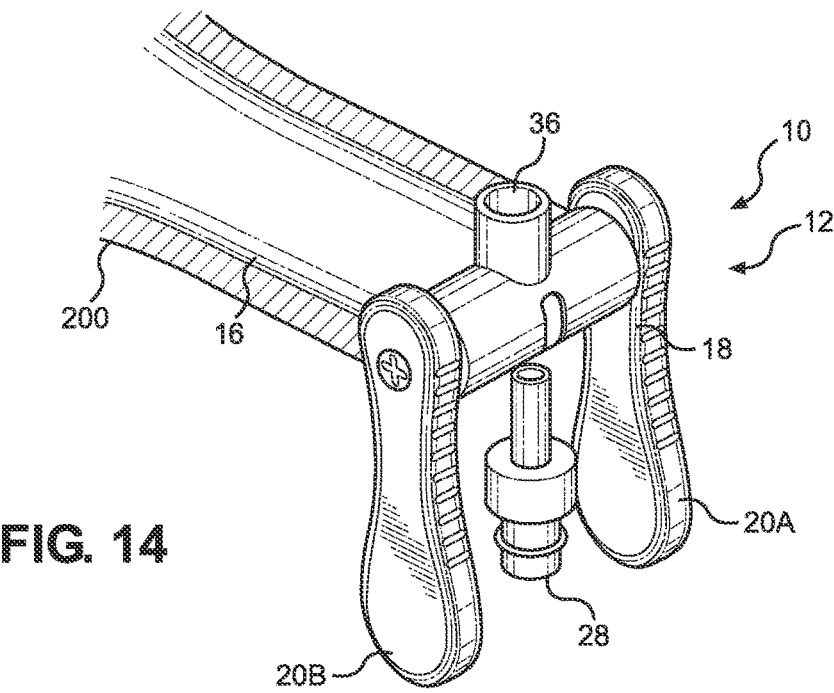
FIG. 14 is a perspective view of the fluid exchange structure applied to a vessel with the unified fluid exchange valve in a closed position.

The fluid exchange valve 32 could be manipulated between the first and second positions in any effective manner, including by a handle, directed manual engagement with the valve 32, by some automated or remote mechanism, or by any effective mechanism. In the depicted embodiment, as can be appreciated best with additional reference to FIG. 14, the valve 32 is pivotable by operation of either or both of first and second lever arms 20A and 20B that are secured to and fixed to pivot with opposed ends of the base portion 34. In one practice of the invention, the first and second lever arms 20A and 20B can be disposed to align longitudinally with the stopper 16 and the bottle 200 in general when the fluid exchange valve 32 is in the open position as, for instance, in FIGS. 1, 3A, and 3B, and the first and second lever arms 20A and 20B can be disposed to be generally perpendicular to a longitudinal of the stopper 16 and the bottle 200 in general when the fluid exchange valve 32 is in the closed position as, for instance, in FIGS. 2A, 2B, and 14. The lever arms 20A and 20B in this embodiment are substantially equal in size and shape. With this, the arms 20A and 20B are operative as stabilizing legs when in the first, closed position as in FIG. 14. With that, a bottle 200 or other vessel can be stably rested on a support surface with the arms 20A and 20B cooperating to support the upper end of the bottle 200. Each arm 20A and 20B can have a length from its pivot axis to its distal end greater than the dispensing valve 28 where the arms 20A and 20B and the dispensing valve project co-directionally, and that length could, for instance, be calibrated to correspond to the radius of the base of a typical wine bottle 200 such that the bottle 200 could be retained horizontally or at some desired angle of incline or decline.

With combined reference to FIGS. 2B, 3B, 4, and 5, the stopper 16 can be perceived to have a liquid exhaust conduit 24 and a gas inlet conduit 26. The liquid exhaust conduit 24 is larger in cross-sectional area than the gas inlet conduit 26. Each conduit communicates longitudinally along the stopper with a first end that is open to the inner volume of the vessel 200 when the stopper 16 is applied thereto, and each conduit 24 and 26 has a second end that is open to the valve positioning pathway 50 and is thus open to the fluid exchange valve 32. At their second ends, the conduits 24 and 26 terminate in relatively narrowed conduit portions 45 and 38 respectively. The conduit portion 38 approximates the shape and cross-sectional area of the conduit joining channel 46, and the conduit portion 45 has a cross-sectional area spanning to overlap the conduit joining passageways 48A and 48B when they are aligned with the conduit 45. A distal conduit portion 40 is disposed in the head portion with a first end open to the valve positioning pathway and the fluid exchange valve 32 and a second end open to the valve coupling 28. As best seen, for instance, in FIG. 4, the barrel-shaped base portion 34 of the fluid exchange valve 32 has a first solid wall portion 42 that operates to overlie and seal the conduit portion 45 of the liquid exhaust conduit 24 and a solid wall portion 44 that operates to overlie and seal the conduit portion 38 of the gas inlet conduit 26 when the fluid exchange valve 32 is in the closed position.

Figure 2A:
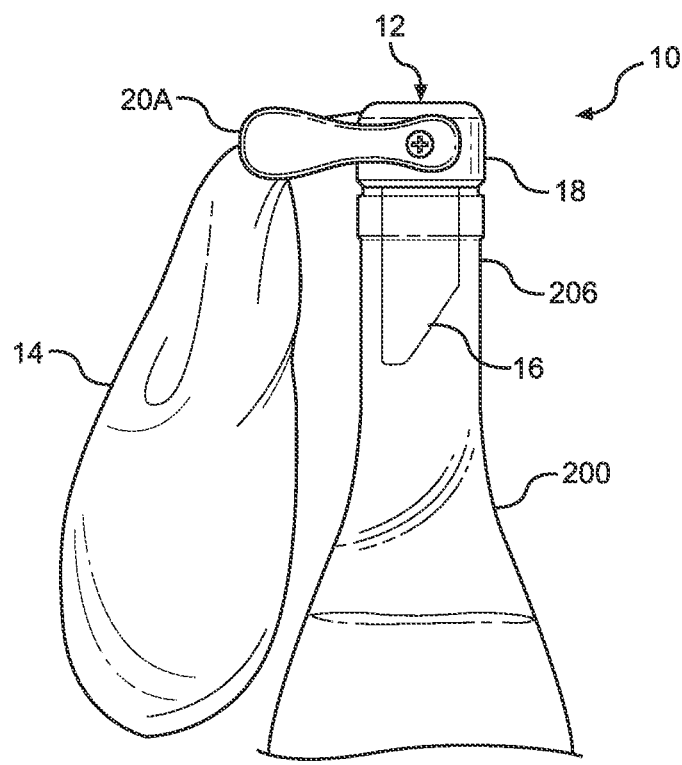
FIG. 2A is a view in front elevation of the preservation system of FIG. 1, again applied to a vessel, with the unified fluid exchange valve in a closed position.
Figure 2B:
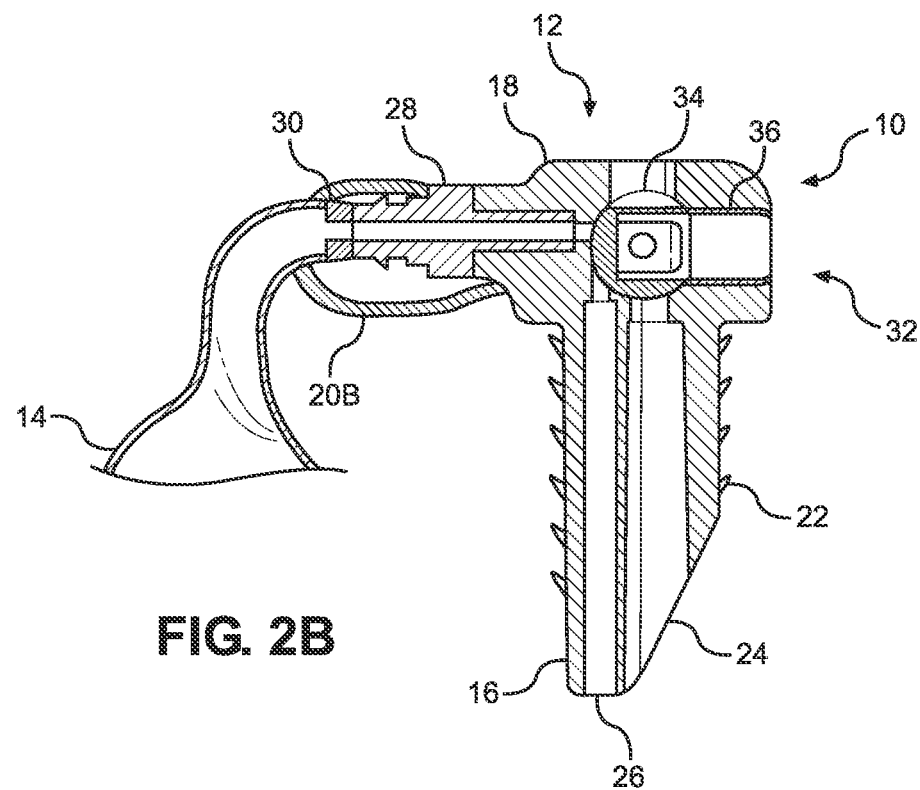
FIG. 2B is a cross-sectional view of the preservation system of FIG. 2A with the unified fluid exchange valve in a closed position.
Figure 3A:
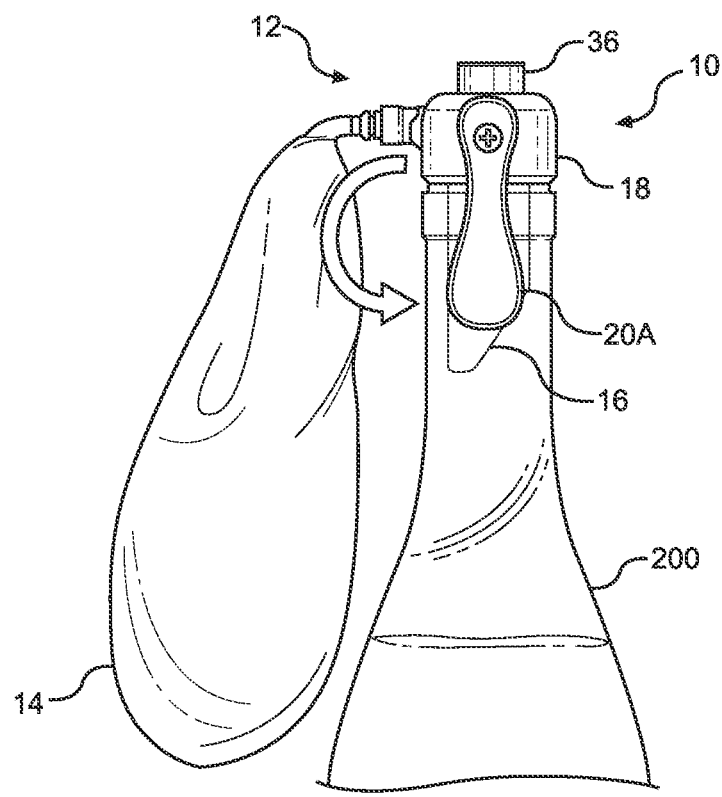
FIG. 3A is a view in front elevation of the preservation system of FIG. 1 applied to a vessel, with the unified fluid exchange valve in an open position.
Figure 3B:
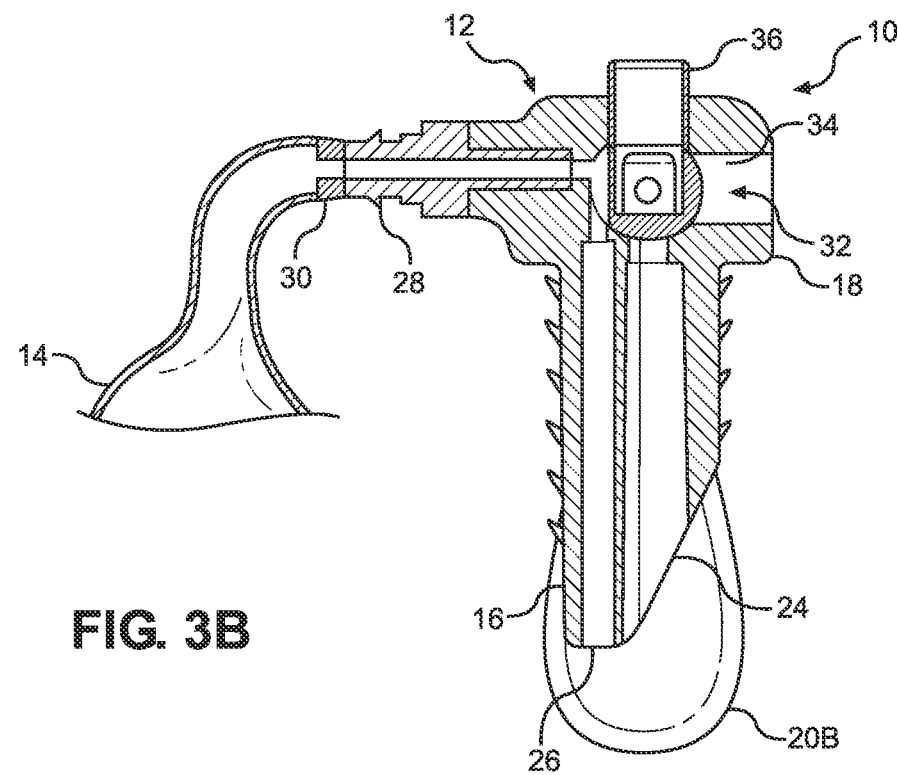
FIG. 3B is a cross-sectional view of the preservation system of FIG. 2A with the unified fluid exchange valve in an open position.
Figure 4:
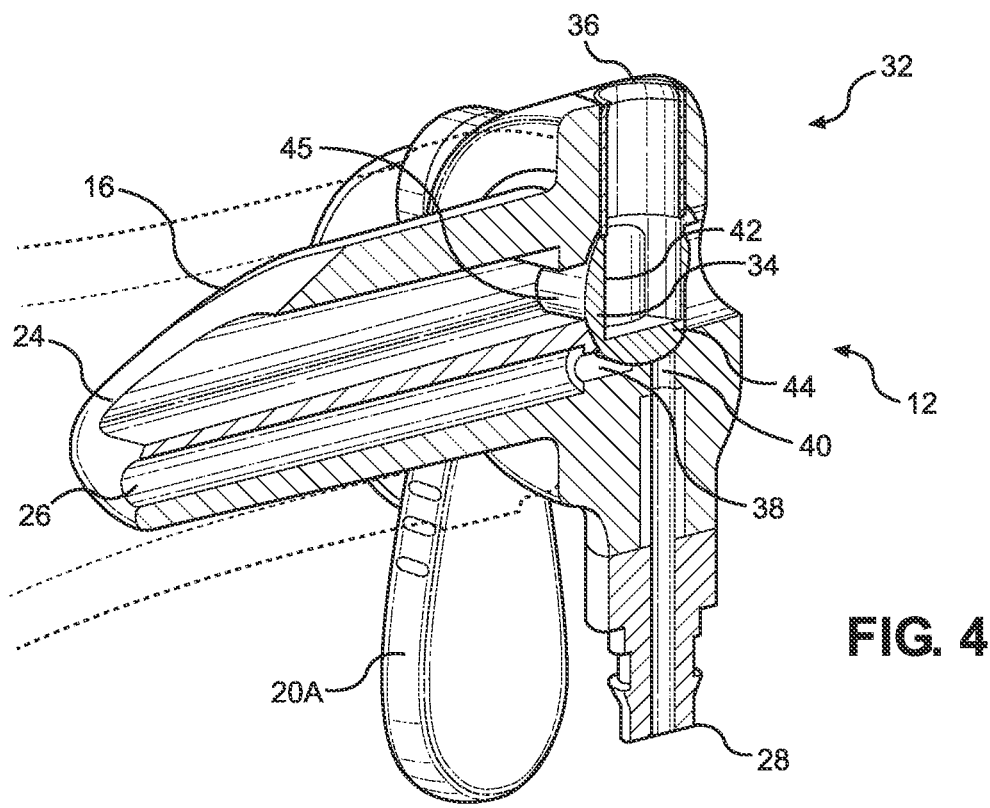
FIG. 4 is a sectioned perspective view of the preservation system of FIG. 1 applied to a vessel with the unified fluid exchange valve in a closed position.
Figure 5:
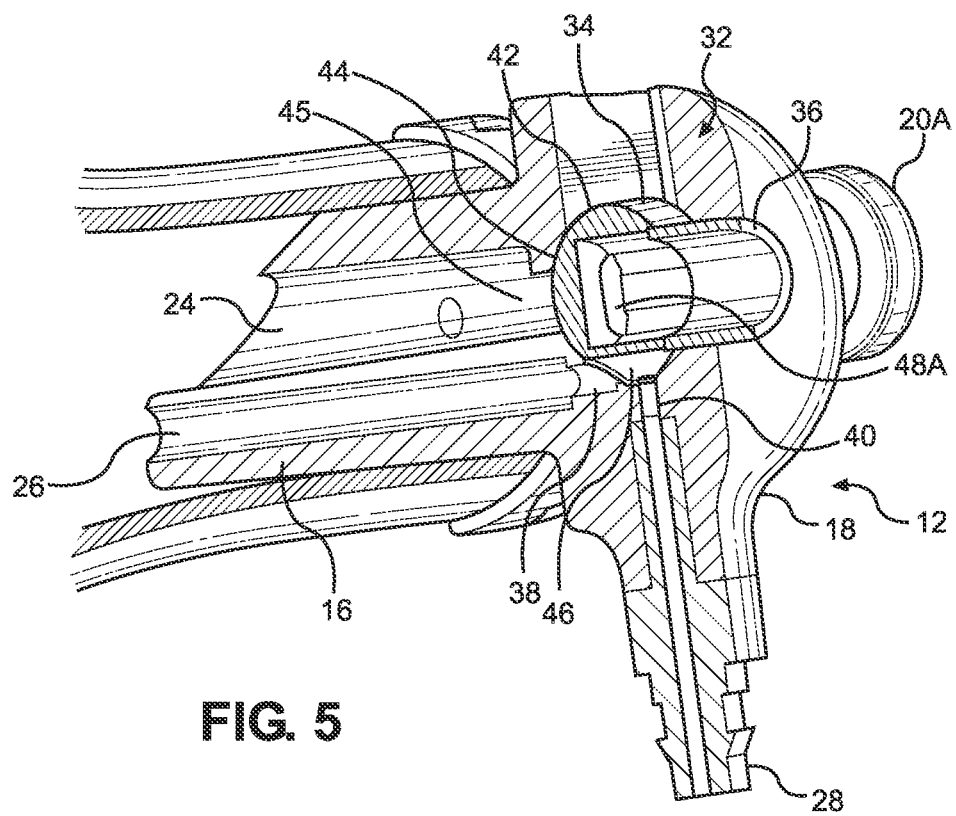
FIG. 5 is a sectioned perspective view of the preservation system of FIG. 1 applied to a vessel with the unified fluid exchange valve in an open position.
Figure 6:
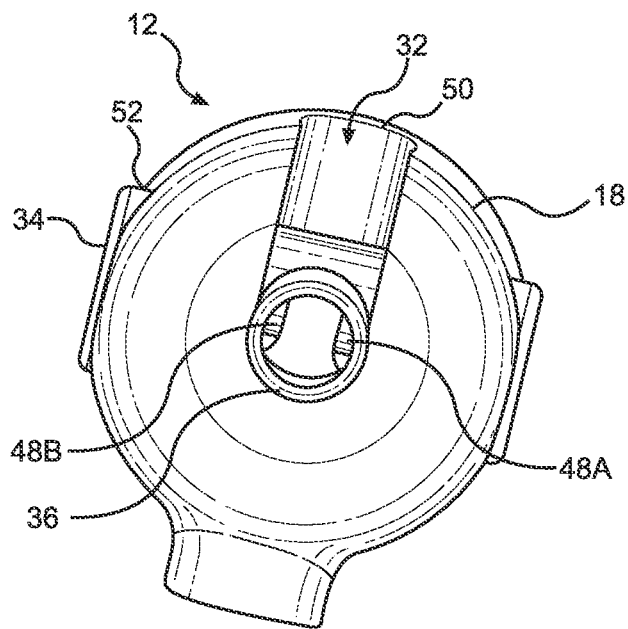
FIG. 6 is a top plan view of the fluid exchange structure formed by the unified fluid exchange valve and the fluid exchange stopper with the fluid exchange stopper in an open position.
Figure 7:
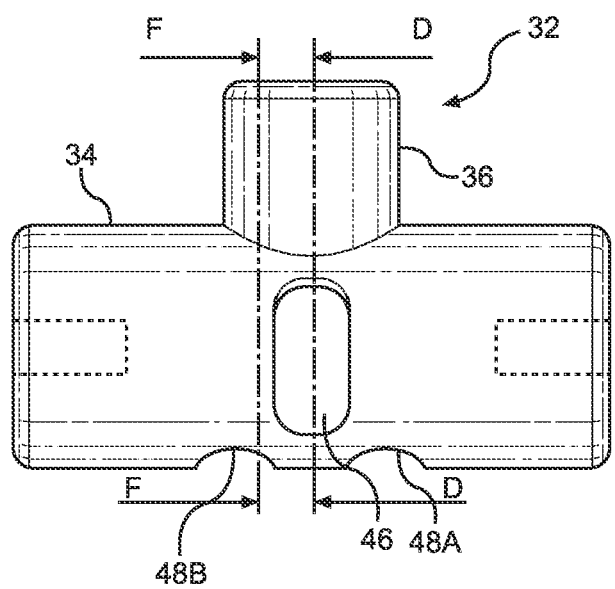
FIG. 7 is a top plan view of the unified fluid exchange valve.
Figure 8:
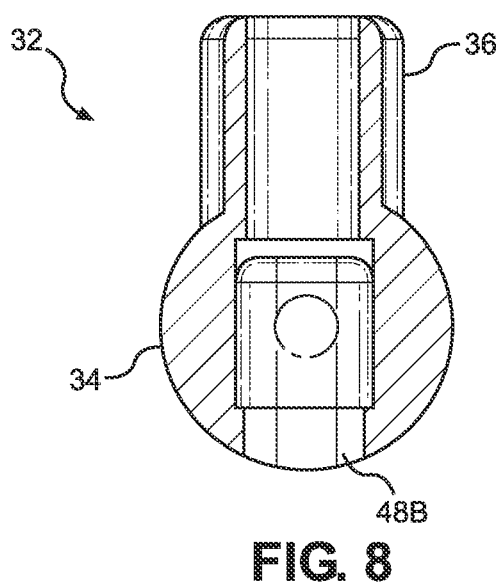
FIG. 8 is a cross-sectional view of the unified fluid exchange valve taken along the line F-F in FIG. 7.
Figure 9:
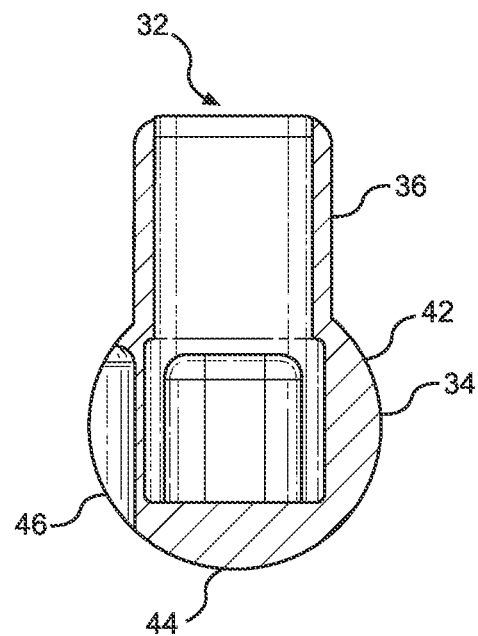
FIG. 9 is a cross-sectional view of the unified fluid exchange valve taken along the line D-D in FIG. 7.
Figure 10:
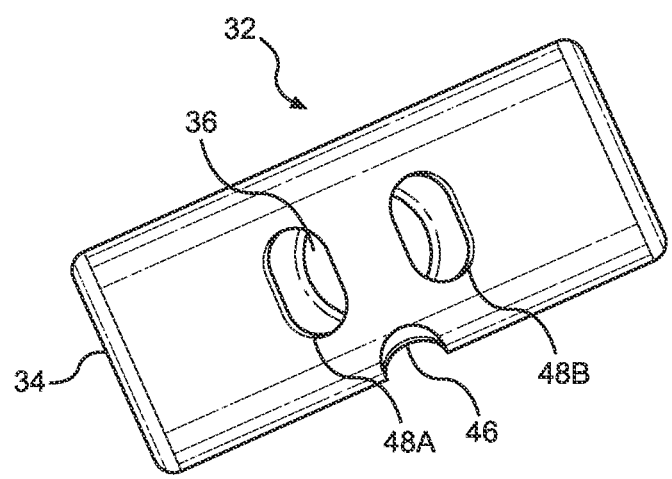
FIG. 10 is a view in rear elevation of the unified fluid exchange valve.
Figure 11:
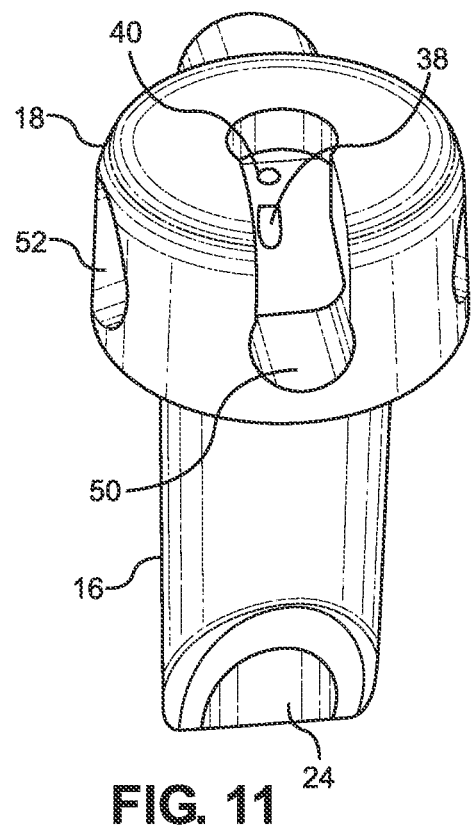
FIG. 11 is a perspective view of the fluid exchange stopper.
Figure 12:
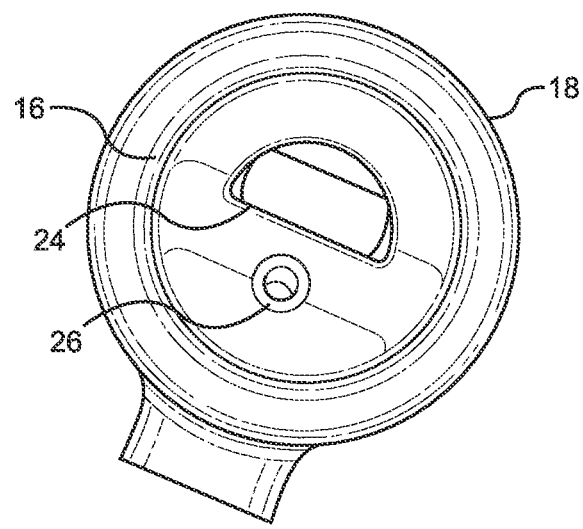
FIG. 12 is a bottom plan view of the fluid exchange stopper.
Figure 13:
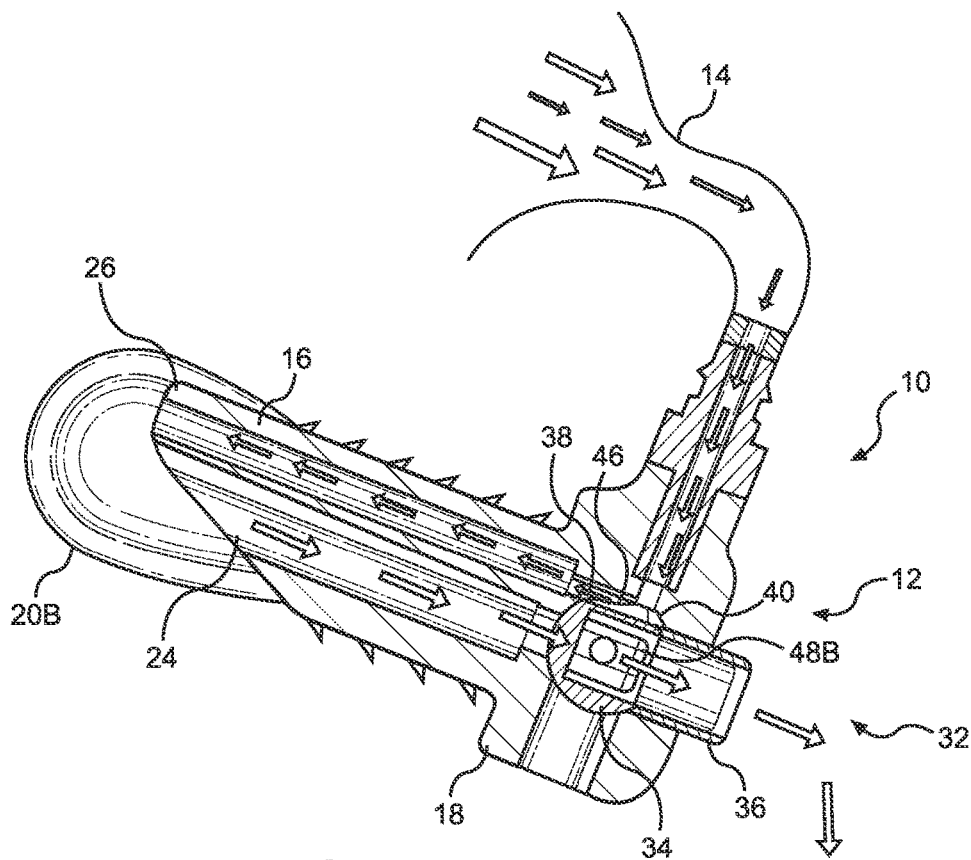
FIG. 13 is a cross-sectional view of the preservation system of FIG. 1 with the unified fluid exchange valve in an open position schematically depicting a fluid exchange process.

Under this construction, orientation of the fluid exchange valve 32 in the closed position, as is illustrated, for instance, in FIGS. 2A, 2B, and 4 will cause the solid wall portions 42 and 44 of the fluid exchange valve 32 to seal the ends of the liquid exhaust conduit 24 and the gas inlet conduit 26 of the stopper 16, and the dispensing nozzle 36 will be disposed in a storage position against the radially communicating lower surface of the valve positioning pathway 50. With that, the inner volume of the vessel 200 is sealed; liquid cannot be exhausted, and gas cannot enter. Adjustment of the fluid exchange valve 32 to the open position illustrated, for example, in FIGS. 3A, 3B, and 5, will rotate the solid wall portions 42 and 44 out of alignment with the conduits 24 and 26. The conduit joining channel 46 and the conduit joining passageways 48A and 48B are rotated into the positions illustrated. An open fluidic inlet pathway is provided from the inner volume of the vessel 200, through the conduit 26, the conduit joining channel 46, the distal conduit portion 40, and the valve coupling 28. Simultaneously, an open fluidic exhaust pathway is created from the inner volume of the vessel 200, through the conduit 24, the conduit joining passageways 48A and 48B, and the dispensing nozzle 36. With the fluidic pathways open, liquid exhausted through the open exhaust pathway will naturally draw in and be replaced by preservative gas drawn into the inner volume of the vessel through the open inlet pathway from the compressible bladder 14 as shown schematically, for example, in FIG. 13.

Figure 17A:
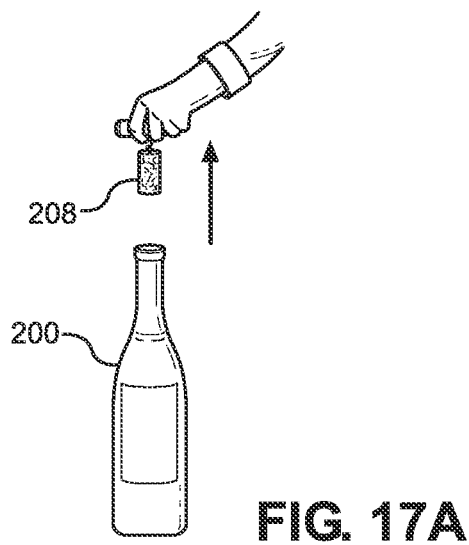
FIGS. 17A through 17E depict a series of steps in a process of dispensing and preserving a volume of liquid in relation to an inner volume of a vessel as taught herein.
Figure 17B:
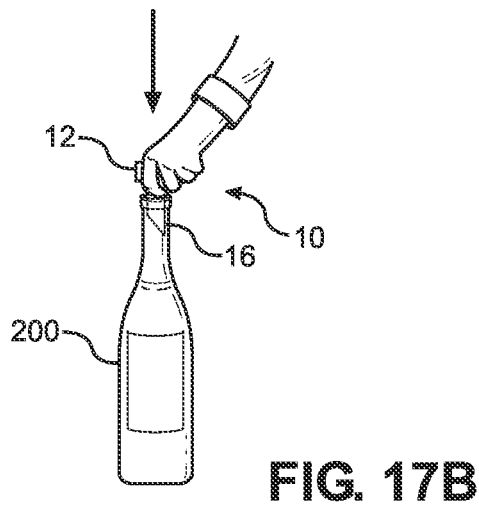
Figure 17C:
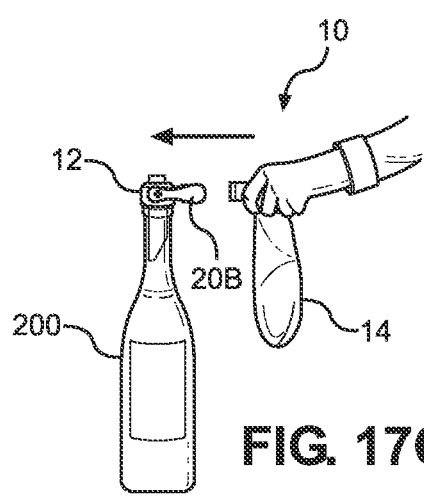
Figure 17D:
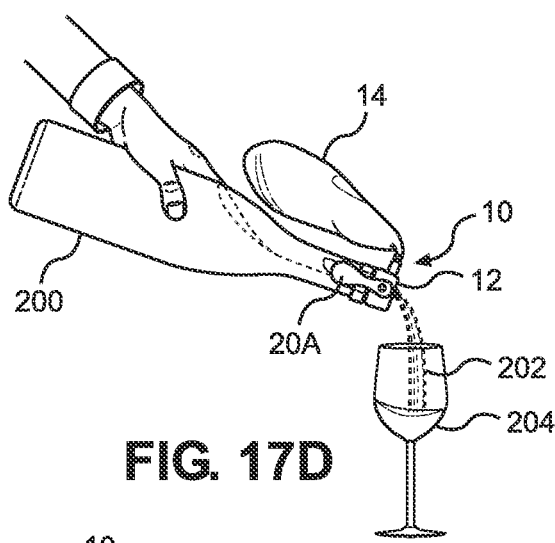
Figure 17E:
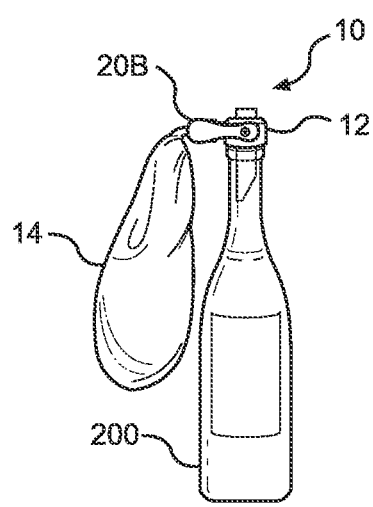
Figure 18:
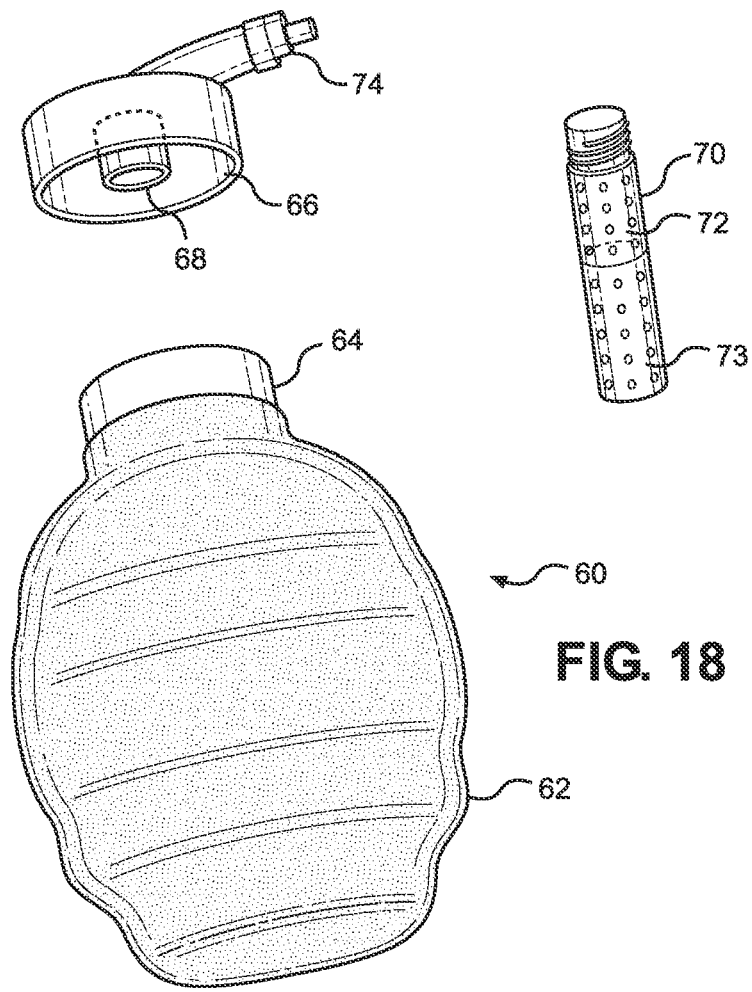
FIG. 18 is an exploded perspective view of an inert gas production canister as taught herein.
Figure 19:
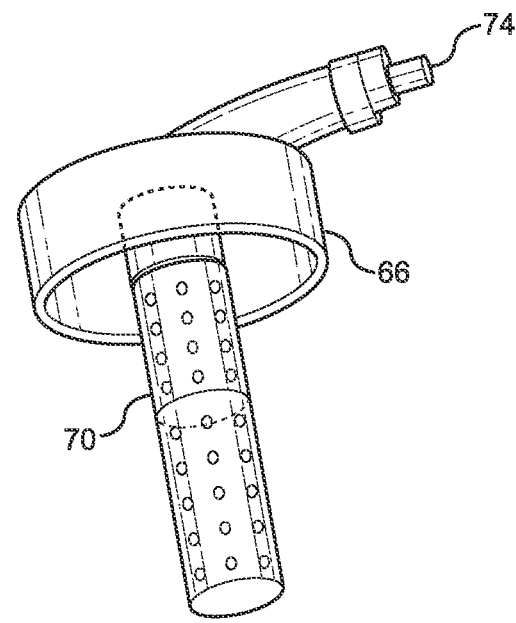
FIG. 19 is a perspective view of a lid portion of the inert gas production canister.

A process for preserving the contents of a vessel 200 can be practiced as suggested by combined reference to FIGS. 17A through 17E where the volumetric displacement preservation system 10 is again employed in the preservation of wine 202 in a wine bottle 200. In this example, the original cork 208 can be first removed from the wine bottle 200 as in FIG. 17A, and the stopper 16 of the volumetric displacement preservation system 10 can be inserted in its stead, potentially with the fluidic exchange valve 32 in a closed condition whereby the inner volume of the bottle 200 will be sealed to the outside atmosphere. The bladder 14 can then be engaged with the fluid exchange structure 12 as shown in FIG. 17C. Then, in any order, the vessel 200 can be disposed in a dispensing condition, such as by being tilted over a receiving vessel 204, and the fluidic exchange valve 32 can be adjusted to an open condition, such as by operation of one or both of the lever arms 20A or 20B. With that, the fluidic inlet and exhaust pathways will be opened. The liquid 202 can then be exhausted, such as by the force of gravity, as shown in FIG. 17D. However, it will be appreciated that the application of a compressive pressure on the bladder 14 could additionally or alternatively be used to force preservative gas into the open inner volume of the vessel 200. In any event, as liquid 202 is passed from the inner volume of the vessel 200 through the fluidic exhaust pathway, preservative gas will pass into the inner volume of the vessel 200 from the bladder 14 in volumetric displacement. The bladder 14 will deflate corresponding to the volume of liquid 202 dispensed, and the inner volume of the vessel 200 will then retain the received volume of preservative gas in protection of the remaining contents of the vessel against degradation. The fluidic exchange valve 32 can be adjusted to the closed position illustrated in FIG. 17E, potentially during the dispensing of liquid 202 from the vessel 200 to prevent the introduction of ambient air into the inner volume of the vessel 200.

Figure 22A:
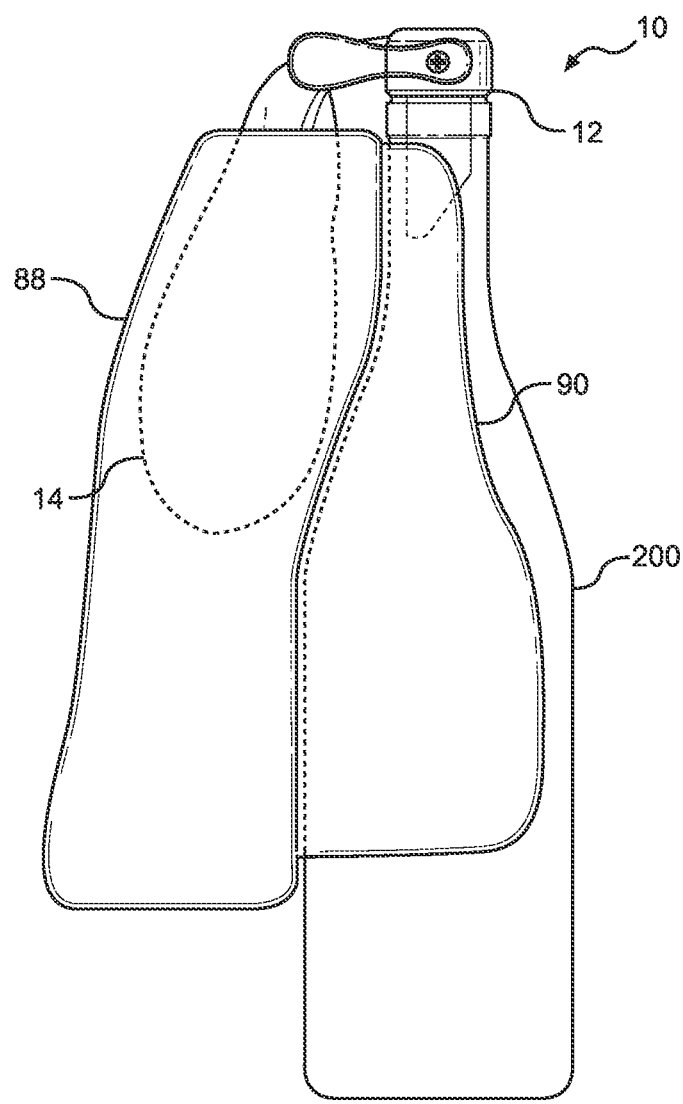
FIG. 22A is a view in side elevation of an embodiment of the preservation system with a shell applied to a vessel.
Figure 22B:
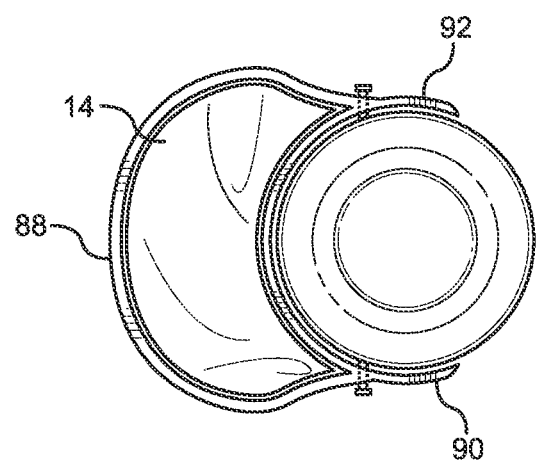
FIG. 22B is a bottom plan view of the preservation system with a shell applied to a vessel of FIG. 22A.

As illustrated, for example, in FIG. 1, the bladder 14 and the remainder of the volumetric displacement preservation system 10 could be used in an unprotected fashion. It is contemplated, however, that the bladder 14 could be partially, substantially, or entirely enveloped in a protective shell 88, which can be substantially rigid, as seen in FIGS. 22A and 22B. There, the protective shell 88 is contoured, including with an inner wall that can correspond to the contour of the vessel 200. The protective shell 88 can be retained in place relative to the volumetric displacement preservation system 10 in any effective manner. In this example, first and second arcuate wings 90 and 92, which can be fixed or resilient, are fixed to the protective shell 88 to receive and engage the vessel 200. For instance, a wine bottle 200 could be slid longitudinally into engagement with the protective shell 88 and the wings 90 and 92, or the wings 90 and 92 could be outwardly biased and the wine bottle 200 inserted therebetween. In any case, where the bladder 14 is disposed in a protective shell 88, inadvertent compression, displacement, or damage to the bladder 14 can be prevented.

Figure 23:
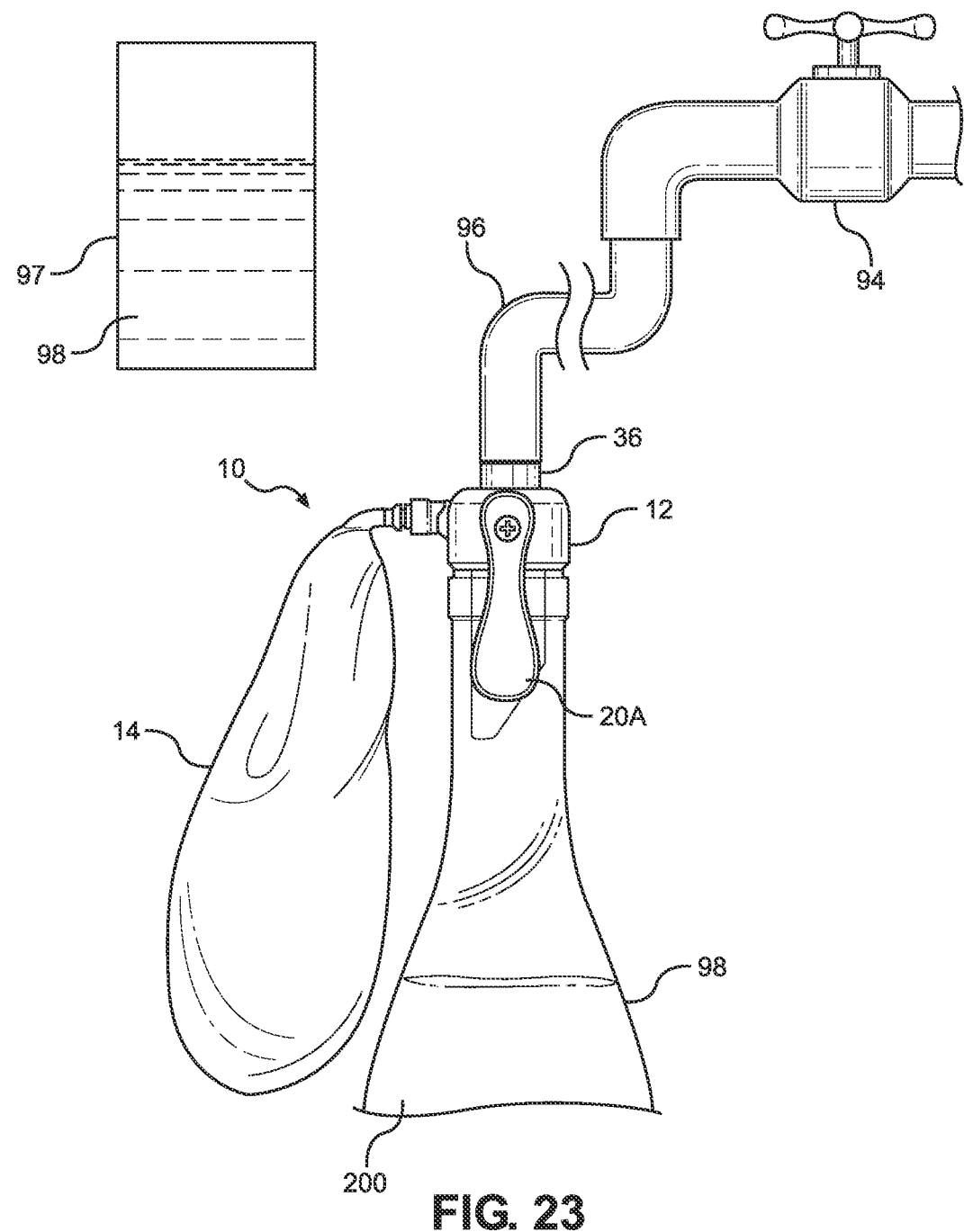
FIG. 23 is a perspective view of an embodiment of the preservation system during a process of gas retrieval by volumetric displacement.
Figure 24A:
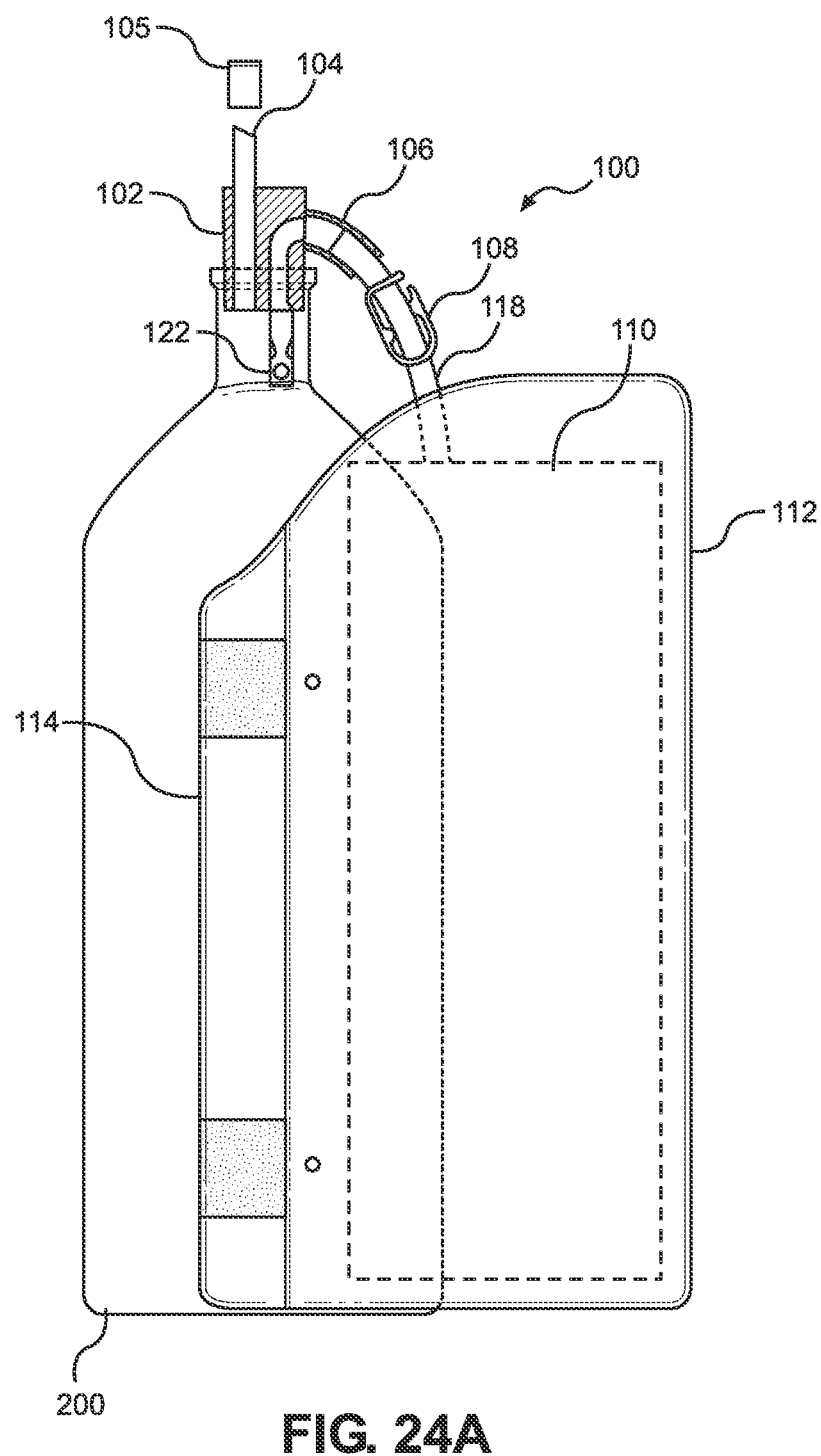
FIG. 24A is a view in side elevation of an alternative embodiment of the preservation system with a shell applied to a vessel.
Figure 24B:
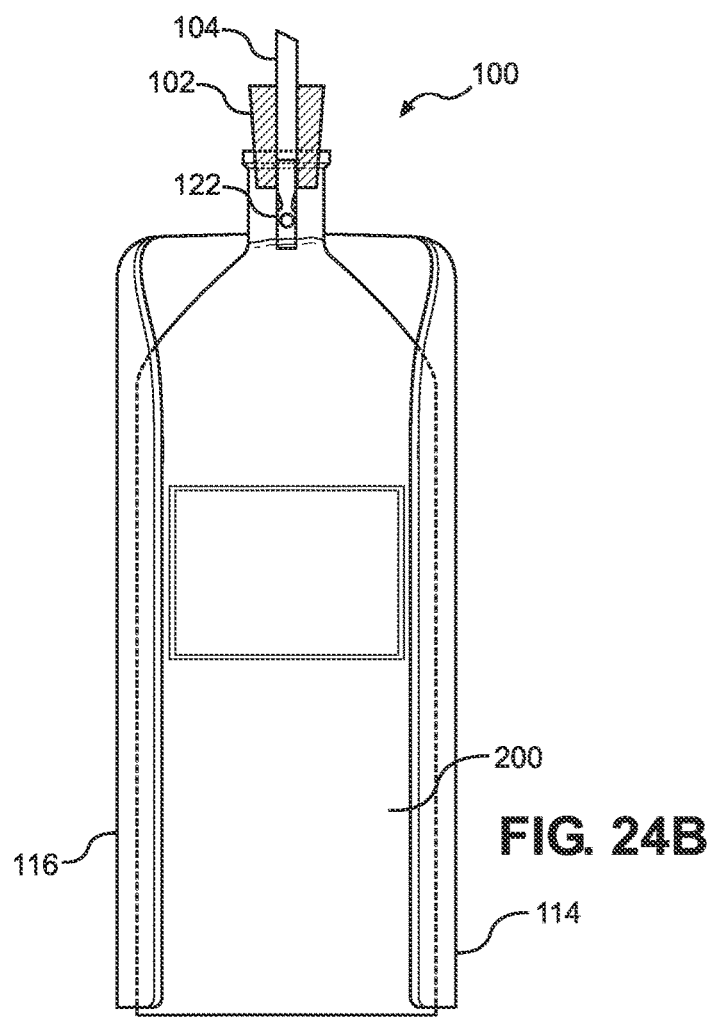
FIG. 24B is a view in front elevation of an alternative embodiment of the preservation system with a shell applied to a vessel of FIG. 24A.
Figure 24C:
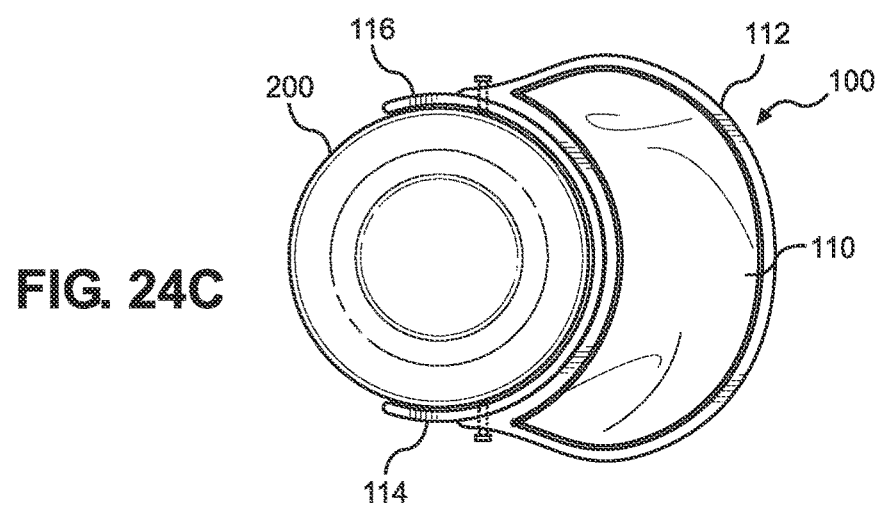
FIG. 24C is a bottom plan view of the preservation system with a shell applied to a vessel of FIG. 24A.
Figure 25A:
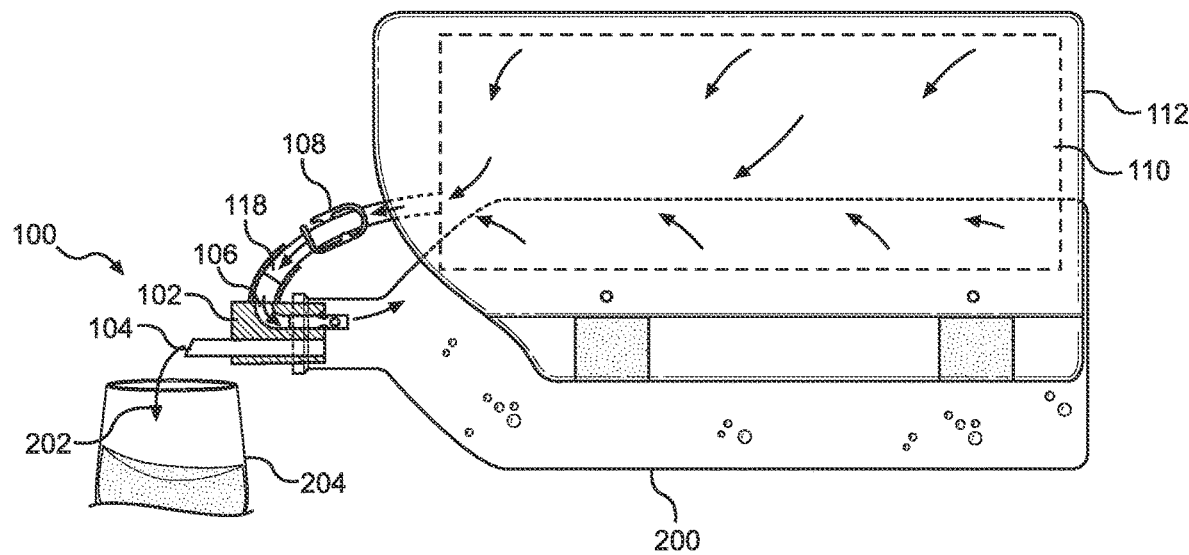
FIGS. 25A through 25C depict a series of steps in a process of dispensing and preserving a volume of liquid in relation to an inner volume of a vessel as taught herein.
Figure 25B:
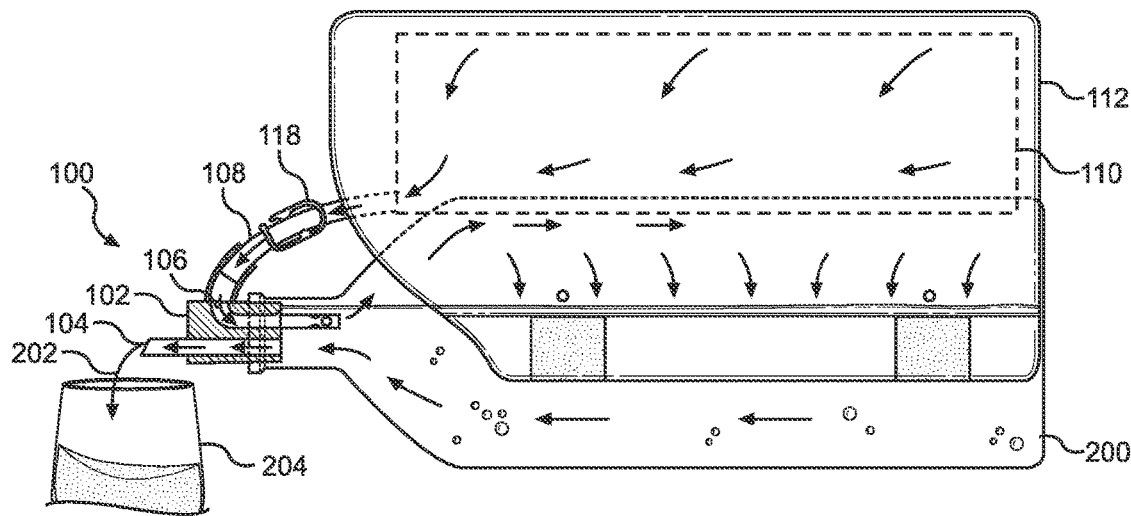
Figure 25C:
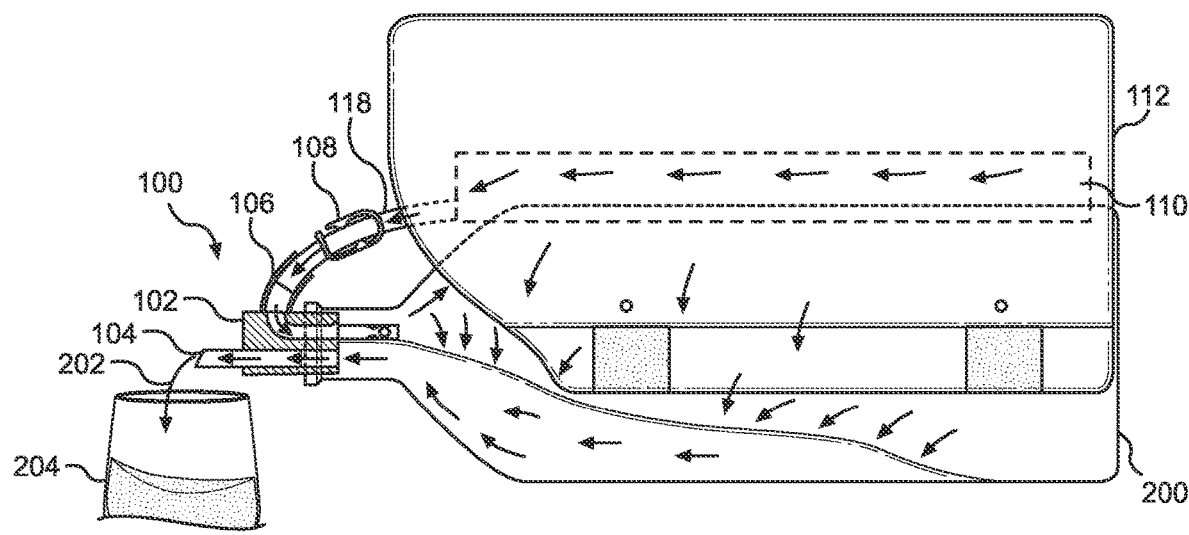

At some point, the usable volume of preservative gas in the bladder 14 will be exhausted, and the bladder 14 must be replenished or replaced. One advantageous method for replenishing the preservative gas in the bladder 14 can be understood with further reference to FIG. 23. There, a reverse volumetric displacement process is shown for harvesting preservative gas from the inner volume of a vessel 200 whose liquid contents have been dispensed and volumetrically replaced by preservative gas. The dispensing nozzle 36 is connected to a source of displacement liquid, such as water or any other liquid, by a conduit 96. The displacement liquid could even in theory be the same type of liquid that was dispensed. While any source of displacement liquid could be employed, one illustrated source is a faucet 94 and another illustrated source is a displacement vessel 97 holding a volume of displacement liquid 98. The displacement vessel 97 could, for example, hold a volume of liquid 98 at least equal to the volume of preservative gas to be harvested from the inner volume of the vessel 200.

In any event, with the source of displacement liquid fluidically connected to the exhaust nozzle 36 by the conduit 96 and the fluidic exchange valve 32 adjusted to an open condition, displacement liquid 98 can be caused to flow into the inner volume of the vessel 200 through the exhaust nozzle 36 and the fluidic exhaust pathway in communication therewith. The displacement liquid 98 could simply flow under the force of gravity, or it could be supplied under a given pressure. By volumetric displacement, the incoming displacement liquid 98 will force the preservative gas from within the inner volume of the vessel 200 back into the bladder 14. With that, the same preservative gas, or at least some portion thereof, can be reused.

While the displacement vessel 97 could comprise any type of vessel including a beaker, a glass, or any other vessel, it is possible that the displacement vessel 97 could match the vessel 200 in size and shape. Where the vessel 200 comprises a wine bottle 200, the displacement vessel 97 could even comprise another wine bottle, such as a used bottle filled with water or another displacement liquid 98, or even a new wine bottle filled with wine. To this extent, it is possible and within the scope of the invention for a single vessel 200, which might be shaped as a wine bottle or a vessel of another shape, and, additionally or alternatively, a single volume of preservative gas, to be used repeatedly or indefinitely. In such a practice, liquid 202 within the vessel 200 can be progressively exhausted and volumetrically replaced by preservative gas. Then, displacement liquid 98, such as wine from a new bottle acting as a displacement vessel 97, water, or some other liquid, can be passed into the inner volume of the vessel 200 to refill the vessel 200 with liquid 202 and the bladder 14 with preservative gas.

Figure 21A:
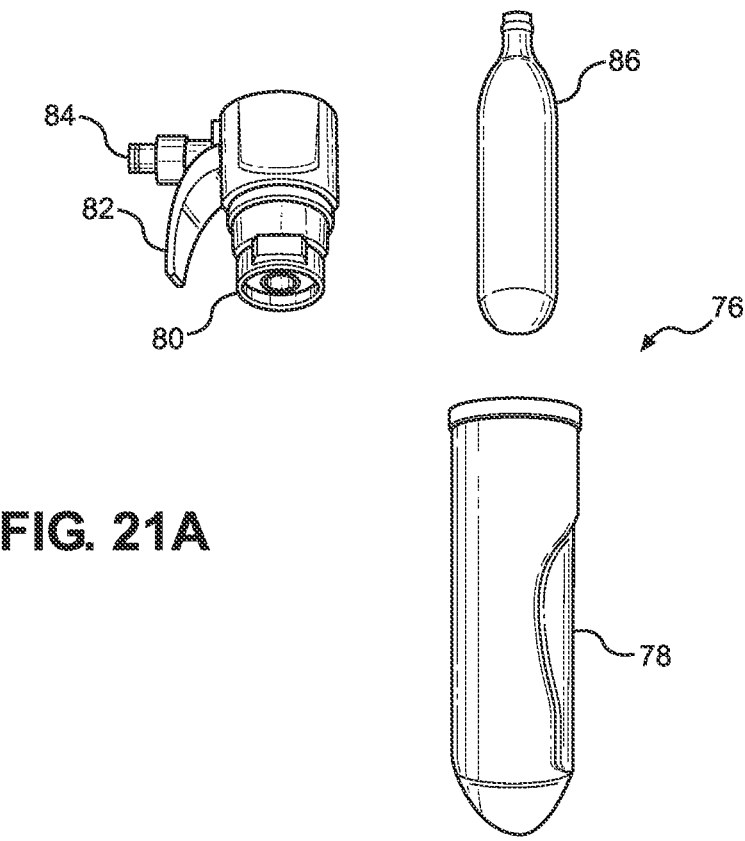
FIG. 21A is an exploded perspective view of a compressed inert gas supply system usable under the present invention.
Figure 21B:
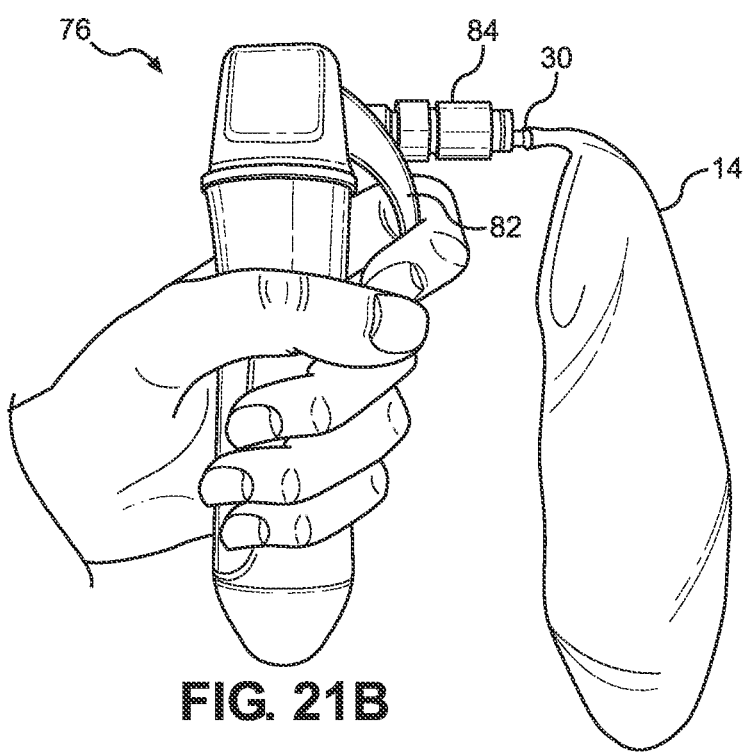
FIG. 21B is a perspective view of the compressed inert gas supply system during a replenishing of a preservative supply bladder.

Of course, the bladder 14 could be replenished by additional or alternative methods. For instance, as shown in FIGS. 21A and 21B, it would be possible to use a compressed gas supply 76 with a compressed gas cylinder 86 containing a volume of preservative gas. Any preservative gas could be used herein, including inert gases, such as but not limited to nitrogen or argon. The compressed gas cylinder 86 could, for example, be inserted into a cylindrical dispenser base 78 and then sealingly engaged with a dispenser head 80 that is operative by a trigger 82 to selectively dispense gas through a dispensing nozzle 84. With this, the valve connector 30 of the bladder 14 can be engaged with the dispensing nozzle 84, and the trigger 82 can be actuated to refill the bladder 14. As taught herein, the dispensing nozzle 84 can have a narrow dispensing aperture so that the compressed gas can be dispensed only at a low flow rate thereby to prevent inadvertent overfilling of the bladder 14.

Figure 29A:
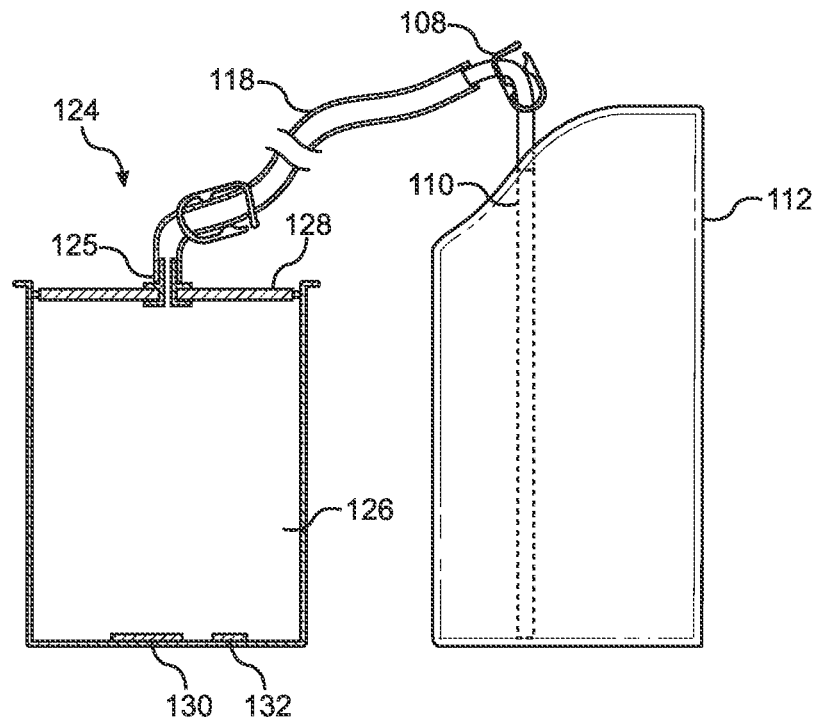
FIGS. 29A through 29C depict a series of steps in a process of producing and harvesting inert gas using an alternative inert gas production canister.
Figure 29B:
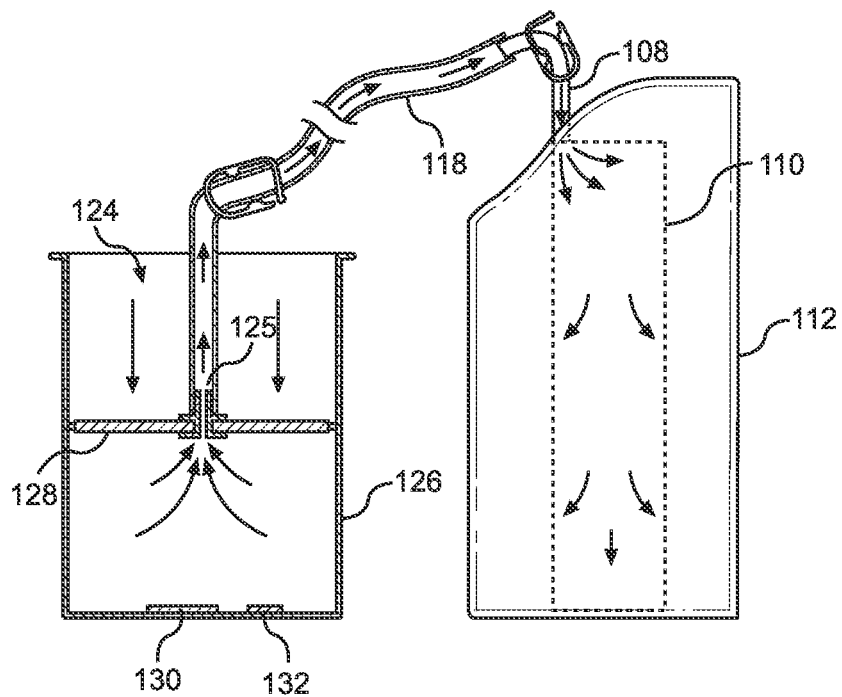
Figure 29C:
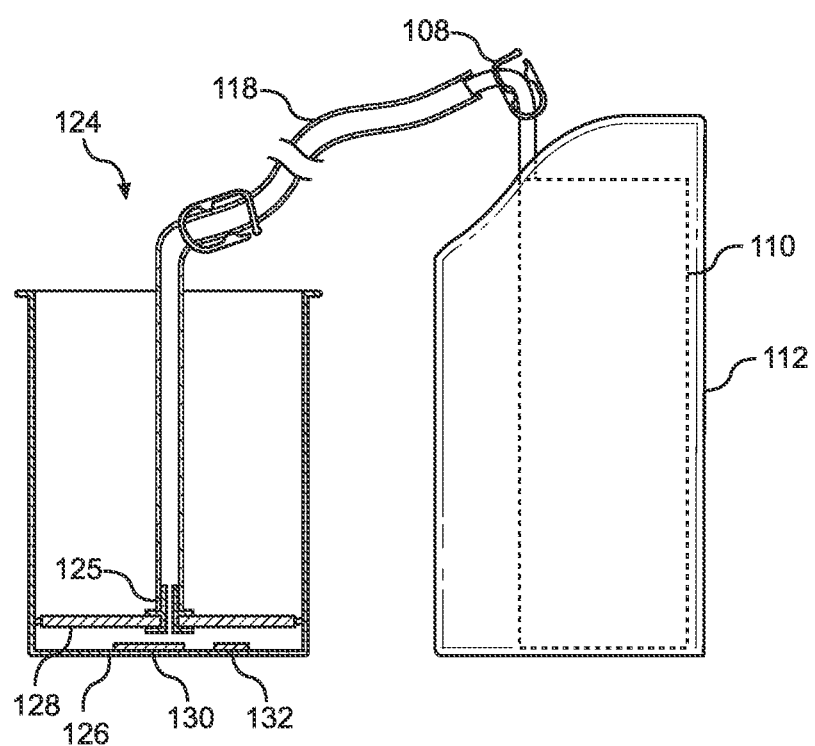

Another method for replenishing the bladder 14 could be by use of an inert gas production canister, such as that indicated at 60 in FIGS. 18 through 20D or that indicated at 124 in FIGS. 29A through 29C relative to an alternative embodiment of the invention. In such inert gas production canisters 60 and 124, ambient oxygen-rich air can be converted to oxygen-poor air, mainly nitrogen, by use of CO2 and oxygen absorbing materials retained within the canister 60 or 124 and in communication with the open inner volume thereof. The resulting gas is thus a preservative gas that can be transferred to the bladder 14 for subsequent use pursuant to the disclosed method. It should be noted that it could be possible and is within the scope of the invention except as it might be expressly limited by the claims to combine the bladder 14 and the inert gas production canister capabilities by enabling the retention of CO2 and oxygen absorbing materials in fluidic communication with the inner volume of the bladder 14. It should be further noted that use of the term production in the sense that the inert gas production canister 60 can yield or produce a volume of substantially inert gas from a volume of air.

The inert gas production canister 60 of FIGS. 18 through 20D has a resiliently compressible shell 62 that, in this embodiment, is ovoid in shape with truncated poles. In one practice of the invention, the shell 62 had a volume of approximately one liter, but the volume can vary depending on, among other things, the application at hand. The shell 62 has a rim 64 that sealingly engages a cap 66, such as by a gasketed and threaded connection therebetween. A valve connector 74 is retained by the cap 66 in fluidic communication with the inner volume of the shell 62. A capsule 70, which can be perforated or otherwise open to the inner volume of the shell 62, is removably and replaceably retained within the open inner volume of the shell 62. The capsule 70 has a first compartment retaining a volume of material 72, such as calcium hydroxide, with CO2 absorbing capacity and a second compartment retaining a volume of material 73 with oxygen absorbing capacity, such as a mixture of iron powder and sodium chloride. The capsule 70 or multiple separate or combined capsules or packets can be disposed in the inner volume of the shell 62 in a fixed or a free-floating manner. The capsule 70 and, additionally or alternatively, the volumes of material 72 and 73 can be removed and replaced when the materials 72 and 74 are spent.

So configured, the inert gas production canister 60 can transform air retained in the inner volume of the shell 62 that is initially composed of, for example, 79% nitrogen, 20% oxygen, 0.5% argon, and 0.5% trace other gases into an environment mainly composed of nitrogen with a small percentage of argon and a very small volume of oxygen, such as 0.1% or less. After a given time period, such as approximately eight hours, the transformation results in a reduction in volume of the contained gases so that the shell 62 will naturally tend to compress from the initial condition shown in FIG. 20A to a partially compressed condition as illustrated in FIG. 20B. With the inner volume of the shell 62 now effectively forming a preservative gas comprised nearly entirely of nitrogen and argon, the valve connector 30 of the bladder 14 can be connected to the valve connector 74 of the inert gas production canister 60 and the bladder 14 can be filled with preservative gas by squeezing the shell 62. Once the bladder 14 is sufficiently filled, the valve connectors 30 and 74 can be disconnected thereby to close the valve connector 30 and seal the preservative gas in the bladder 14 pending use in the volumetric displacement method taught herein.

Figure 28:
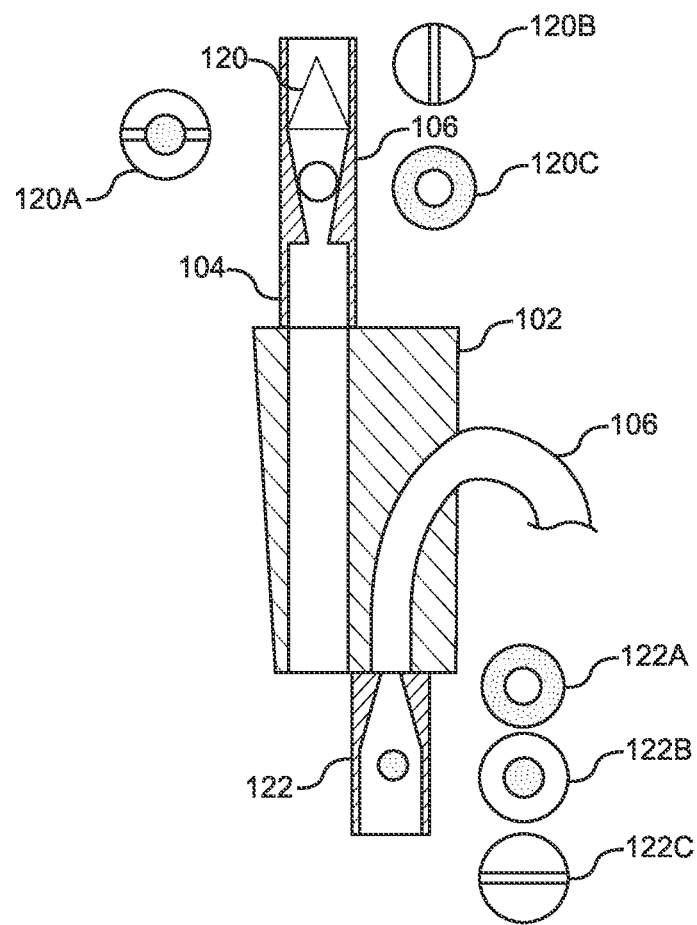
FIG. 28 is a longitudinal cross section of an alternative fluid exchange stopper according to the invention.

As noted previously, the volumetric displacement preservation system and method taught herein are subject to further embodiments within the scope of the invention. One such further volumetric displacement preservation system according to the invention is indicated generally at 100 in FIGS. 24A through 25C. There, the volumetric displacement preservation system 100 is again applied to a vessel 200, which again comprises a wine bottle 200. The volumetric displacement preservation system 100 has a stopper 102 with a fluidic exhaust pathway established by a first, fluid exhaust conduit 104 through the stopper 102 and a fluidic inlet pathway established by a second, fluid inlet conduit 106 through the stopper 102. The second conduit 106 establishing the fluidic inlet pathway is fluidically connected to an expandable and compressible bladder 110, such as by a flexible conduit 118, and a clamp 108 operates to selectively close the fluidic inlet pathway between the stopper 102 and the bladder 110. A cap 105, a clamp (not shown), a valve 120 as shown in FIG. 28, and, additionally or alternatively, any other mechanism can be used to selectively close the fluidic outlet pathway, such as during storage. A valve 122, which could be a one-way valve, can be disposed along the fluidic inlet pathway.

Figure 27:
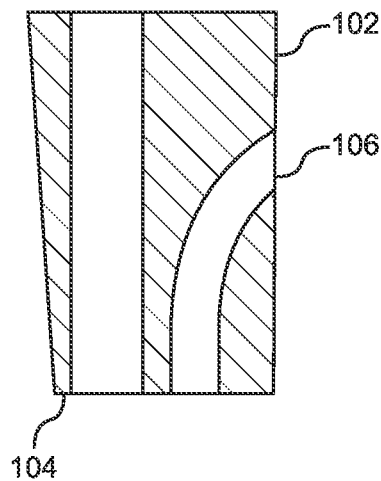
FIG. 27 is a longitudinal cross section of a fluid exchange stopper according to the invention.

Embodiments of the stopper 102 are shown alone in FIGS. 27 and 28. In the embodiment of FIG. 27, the stopper 102 merely has a longitudinal borehole forming the fluidic exhaust conduit 104 and a curved borehole forming the fluidic inlet conduit 106. In the embodiment of FIG. 28, the stopper 102 has the same longitudinal and curved boreholes, except that tubes pass therethrough to act as the fluidic exhaust conduit 104 and the fluidic inlet conduit 106. The cap 106 can be fixed or removable and can have a valve 120 retained thereby, and a valve 122 is retained along the fluidic pathway of the fluidic inlet conduit, such as at the base of the stopper 102. The valves 120 and 122 can be of a variety of types. For instance, the valves 120 and 122 can be check valves allowing fluid flow only in exhaust from the fluidic exhaust conduit 104 and only in incoming flow along the fluidic inlet conduit 106. The valve 120 could have lateral cross sections over its length as illustrated at 120A, 120B, and 120C, and the valve 122 could have lateral cross sections over its length as illustrated at 122A, 122B, and 122C. Either or both valves 120 and 122 can be removable to facilitate, for example, the reverse volumetric displacement process for harvesting preservative gas from the inner volume of the vessel 200.

The bladder 110 and the remainder of the volumetric displacement preservation system 100 could again be used in an unprotected fashion. However, the bladder 110 could be partially, substantially, or entirely enveloped in a protective shell 112 as seen, for instance, in FIGS. 24A through 24C. As before, the protective shell 112 can be retained in place relative to the volumetric displacement preservation system 100 in any effective manner, including but not limited to the illustrated first and second arcuate wings 114 and 116. The wings 114 and 116, which can be fixed or resilient, are fixed to the protective shell 112 to receive and engage the vessel 200. For instance, a wine bottle 200 could be slid longitudinally into engagement with the protective shell 112 and the wings 114 or 116, or the wings 114 or 116 could be outwardly biased and the wine bottle 200 inserted therebetween. With the protective shell 112 disposed to encase or envelop all or part of the bladder 110, inadvertent compression, displacement, or damage to the bladder 110 can be prevented.

Under this construction, a process for preserving the contents of a vessel 200 can be practiced. In this example, the original cork has been removed from the wine bottle 200 and the stopper 102 of the volumetric displacement preservation system 100 has been inserted in its stead. With the bladder 110 sufficiently filled with preservative gas, the vessel 200 can be disposed in a dispensing condition, such as by being tilted over a receiving vessel 204, and the cap 106 can be removed and the clamp 108 adjusted to an open condition. With that, the fluidic inlet and exhaust pathways will be opened. A volume of liquid 202 can then be exhausted, such as by the force of gravity, as progressively shown in FIGS. 25A through 25C. However, it will be appreciated that the application of a compressive pressure on the bladder 110 could additionally or alternatively be used to force preservative gas into the open inner volume of the vessel 200. As liquid 202 is passed from the inner volume of the vessel 200 through the fluidic exhaust pathway, preservative gas will pass into the inner volume of the vessel 200 from the bladder 110 in volumetric displacement. The bladder 110 progressively deflates as the volume of liquid 202 is dispensed as illustrated by the drawings. The inner volume of the vessel 200 will then retain the received volume of preservative gas in protection of the remaining contents of the vessel 200 against degradation. The cap 106 can be reapplied and the clamp 108 can be adjusted to a closed position, potentially during the dispensing of liquid 202 from the vessel 200 to prevent the introduction of ambient air into the inner volume of the vessel 200.

Figure 26A:
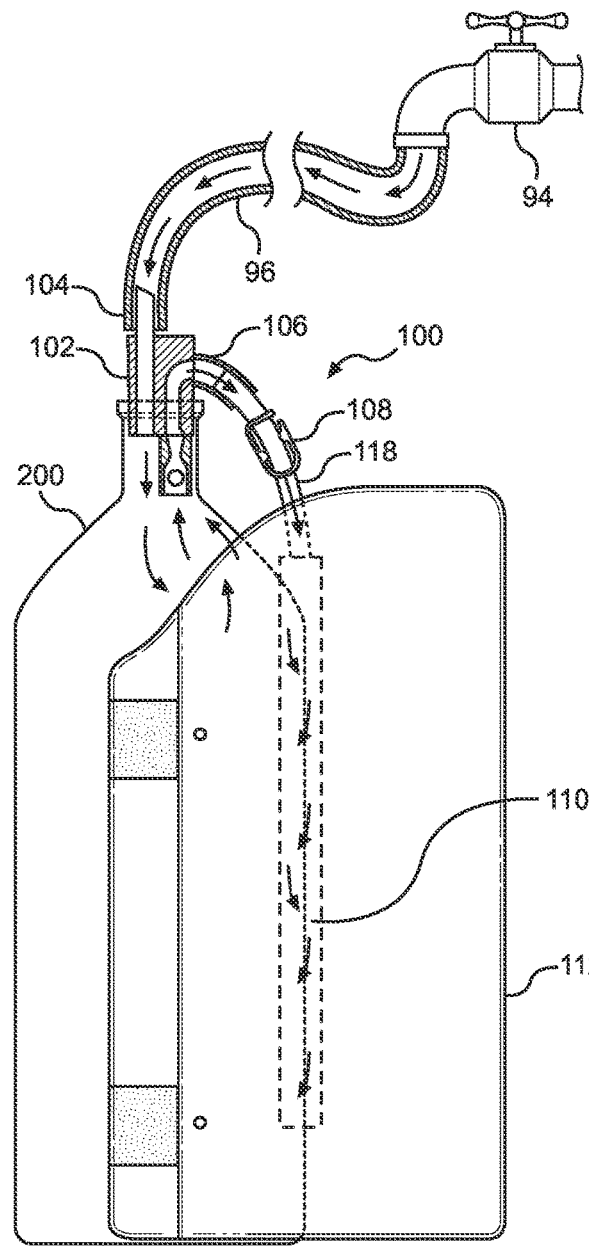
FIGS. 26A through 26C depict the preservation system of FIG. 24A during a series of steps in a process of gas retrieval by volumetric displacement.
Figure 26B:
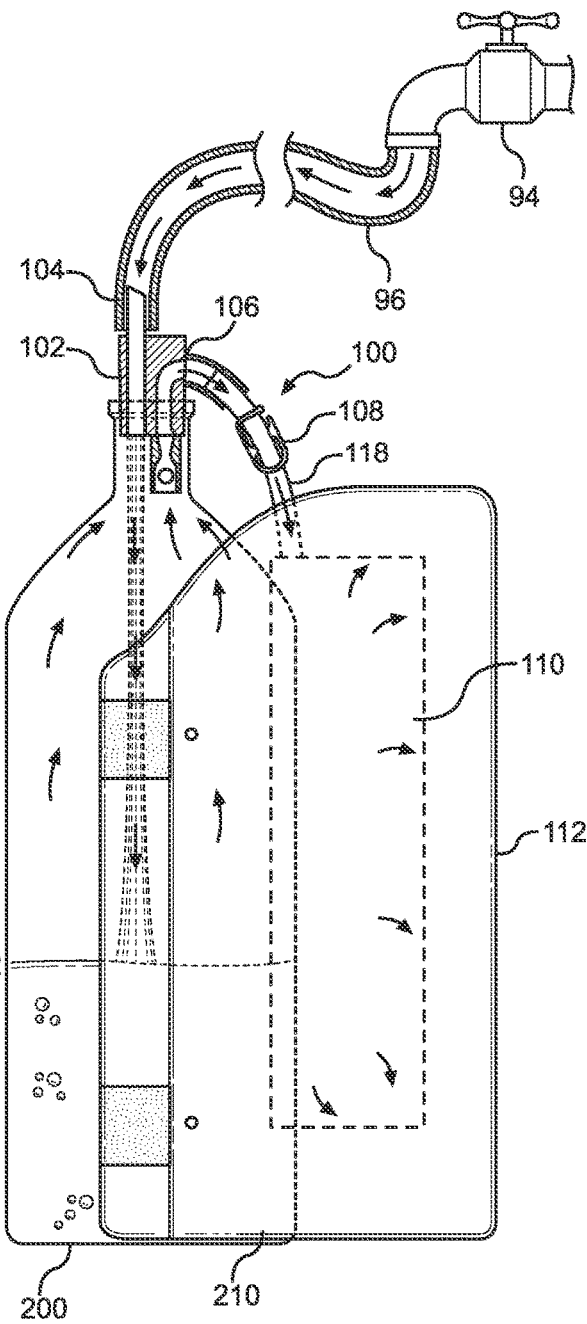
Figure 26C:
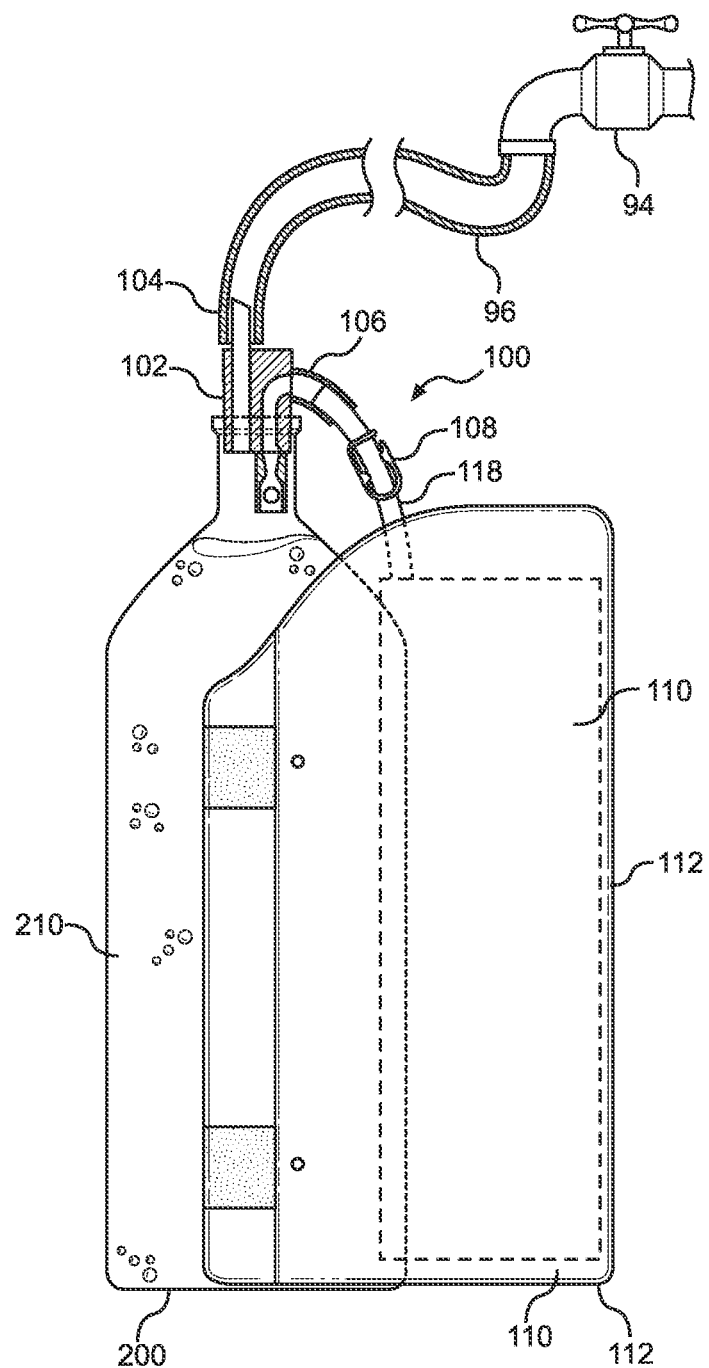

As with the earlier embodiment of the preservation system 10, the bladder 110 could be replenished or replaced when exhausted. As illustrated in FIGS. 26A through 26C, a reverse volumetric displacement process can again be employed to harvest preservative gas from the open inner volume of the bottle 200 and return it to the open inner volume of the bladder 110. To do so, the exhaust conduit 104 can be connected to a source of displacement liquid, such as water or any other liquid, by a conduit 96. While any source of displacement liquid could be employed, one illustrated source is a faucet 94, and another source could be a displacement vessel as illustrated and described previously holding a volume of displacement liquid. Displacement liquid 210 can be caused to flow into the inner volume of the vessel 200 through the exhaust conduit 96 and the fluidic exhaust pathway in communication therewith. The displacement liquid 210 could simply flow under the force of gravity, or it could be supplied under a given pressure. By volumetric displacement, the incoming displacement liquid 210 forces the preservative gas from within the inner volume of the vessel 200 back into the bladder 110. With that, the same preservative gas, or at least some portion thereof, can be reused.

The bladder 110 could again be partially or completely filled or replenished by use of an inert gas production canister, which could be as previously shown and described, as indicated generally at 124 in FIGS. 29A through 29C, or in some other form. In the embodiment of FIGS. 29A through 29C, ambient oxygen-rich air is again converted to oxygen-poor air, mainly nitrogen, by use of CO2 and oxygen absorbing materials retained within the canister 124 and in communication with the open inner volume thereof. The resulting gas is thus a preservative gas that can be transferred to the bladder 110 for subsequent use pursuant to the disclosed method.

The inert gas production canister 124 has a shell 126, which can be rigid, and a lid 128 that is sealingly engaged with the inner surface of the wall or walls of the shell 126 in a slidable manner whereby the inner volume of the canister 124 can be adjusted by a sliding of the lid 128 relative to the shell 126, much like a plunger in a syringe. The shell 126 and the lid 128 can have a variety of cross-sectional shapes, including round, square, or some other shape. A fluidic connector 125 is retained by the lid 128 in fluidic communication with the inner volume of the shell 126. A volume of material 130, such as calcium hydroxide, with CO2 absorbing capacity can be retained in the inner volume of the shell 126, and a volume of material 132 with oxygen absorbing capacity, such as a mixture of iron powder and sodium chloride, can also be retained in the inner volume of the shell 126. The materials 130 and 132 can be disposed in the inner volume of the shell 126 in a fixed or a free-floating manner, and the materials 130 and 132 can be replaced when spent.

It will again be understood that numerous other embodiments of the canister 124 are possible. By way of example and not limitation, other canisters could be expand and contract in a bellows construction or any other preferably expandable and compressible construction. Moreover, the canister 124 can be of any suitable volume. It will be noted, though, that the canister 124 should have a volume larger than the desired resulting volume of preservative gas since the volume of oxygen in the initially present air will be lost. For example, to make 800 milliliters of preservative gas, a 1000 milliliter canister 124 is required since approximately 200 milliliters of volume will be lost as oxygen is removed from the air.

So configured, the inert gas production canister 124 can transform air retained in the inner volume of the shell 126 that is initially composed of, for example, 79% nitrogen, 20% oxygen, 0.5% argon, and 0.5% trace other gases into an environment mainly composed of nitrogen with a small percentage of argon and a very small volume of oxygen, such as 0.1% or less. After a given time period, the transformation results in a reduction in volume of the contained gases so that the shell 126 will naturally tend to compress from the initial condition shown in FIG. 29A to a partially compressed condition. With the inner volume of the shell 126 now effectively forming a preservative gas comprised nearly entirely of nitrogen and argon, the fluidic connector 125 can be connected to the fluidic conduit 118 and, through it, to the bladder 110. The bladder 110 can be filled with preservative gas by pressing on the lid 128 to reduce the volume within the canister 124. Once the bladder 110 is sufficiently filled, the clamp 108 can be closed to seal the preservative gas in the bladder 110 pending use in the volumetric displacement method taught herein.

In each embodiment of the volumetric displacement preservation system 10 and 100 disclosed, a symbiosis is thus created between the vessel 200 and the system 10 or 100 to enhance the consuming experience. Where wine is the substance to be preserved, for example, the components cooperate to help the wine drinker pour and decant the wine 202 as it pours out of the dispensing nozzle 36 or the fluid exhaust conduit 104. The fluidic exhaust pathway so established is narrow enough to exhaust a narrow stream of wine from the bottle 200 to start the decanting process of wine instantly. Moreover, wine passing through the separate conduit joining passageways 48A and 48B and then joined to pass through the nozzle 36 of the fluidic exchange valve 32 will be further aerated to be placed in optimal drinking condition. Still further, the tip of the dispensing nozzle 36 or the exhaust conduit 104 can have a beveled edge to prevent dripping.

As described above, once exhausted of preservative gas, the expandable and compressible bladder 14 could be refilled with preservative gas for subsequent usage by a number of methods. For instance, the reverse volumetric displacement process of FIG. 23 could be employed to harvest preservative gas from the inner volume of a vessel 200 whose liquid contents have been dispensed and volumetrically replaced by preservative gas. It would also possible to use a compressed gas supply 76 with a compressed gas cylinder 86 containing a volume of preservative gas as suggested in FIGS. 21A and 21B. Additionally disclosed above are systems and methods for replenishing the bladder 14 could be by use of an preservative gas production canister external to the bladder 14. Such external preservative gas production canisters are, for example, indicated at 60 in FIGS. 18 through 20D or that indicated at 124 in FIGS. 29A through 29C.

Figure 30:
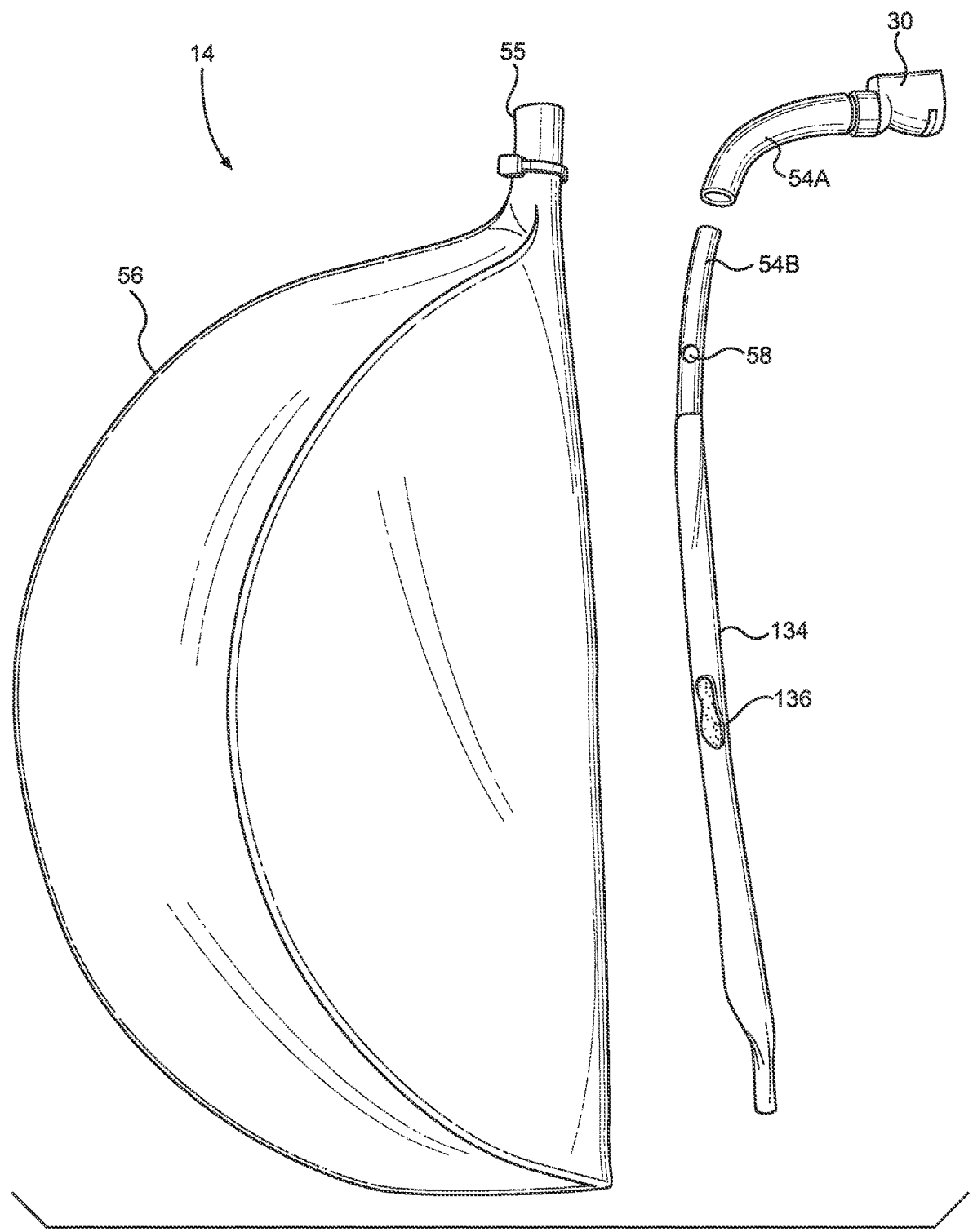
FIG. 30 is a view in front elevation of an external preservative supply bladder according to the invention with an inert gas harvesting member as taught herein.

The foregoing systems and methods are certainly viable and effective. However, one of the present inventors has further appreciated that it could be advantageous if the preservative gas production or harvesting capabilities were incorporated internally within the expandable and compressible bladder 14 itself. Such a bladder 14 is depicted in FIG. 30 in a partially disassembled form. There, the bladder 14 is again founded on a shell 56, which can be of a flexible and substantially gas impermeable material. As previously described, numerous such materials are possible, each within the scope of the invention. By way of a nonrestrictive example, the shell 56 of the bladder 14 can be a polymeric material with or without a lining layer and could take the form of a foil with polymeric material and an aluminum lining.

The shell 56 is sealed but for an orifice 55. A tube structure is formed by first and second tubes 54A and 54B. The first tube 54A in this embodiment has an arcuate portion and has a proximal end and a distal end, and the second tube 54B in this example is generally straight. A valve coupling 30 is disposed to the distal end of the first tube 54A, and the proximal end of the first tube 54A can be selectively engaged with the distal end of the second tube 54B. For example, the tubes 54A and 54B can have inner and outer diameters chosen to permit a substantially sealed arrangement to be achieved therebetween with the distal end of the second tube 54B matingly received into the proximal end of the first tube 54A as shown, for instance, in FIG. 31. Where the tubes 54A and 54B are so disposed and configured, an annular shoulder 138 will thus be established where the tube structure transitions from the narrower outside diameter of the second tube 54B to the larger outside diameter of the first tube 54A.

One or more apertures 58 can be disposed along the tube structure formed by the first and second tubes 54A and 54B to facilitate gas flow. In this example, the aperture or apertures 58 are disposed adjacent to the proximal end of the second tube 54B. With this, the valve coupling 30 and a valve coupling 28 (as in FIGS. 2B and 3B, for instance) can be in fluidic communication with the inner volume of the bladder 14 even where the distal end of the second tube 54B is plugged. Again, the valve coupling 30 can have an automatically sealed condition when not engaged with the valve coupling 28 of the fluid exchange structure 12 and an automatically bidirectionally open condition when engaged with the valve coupling 28.

Figure 34:
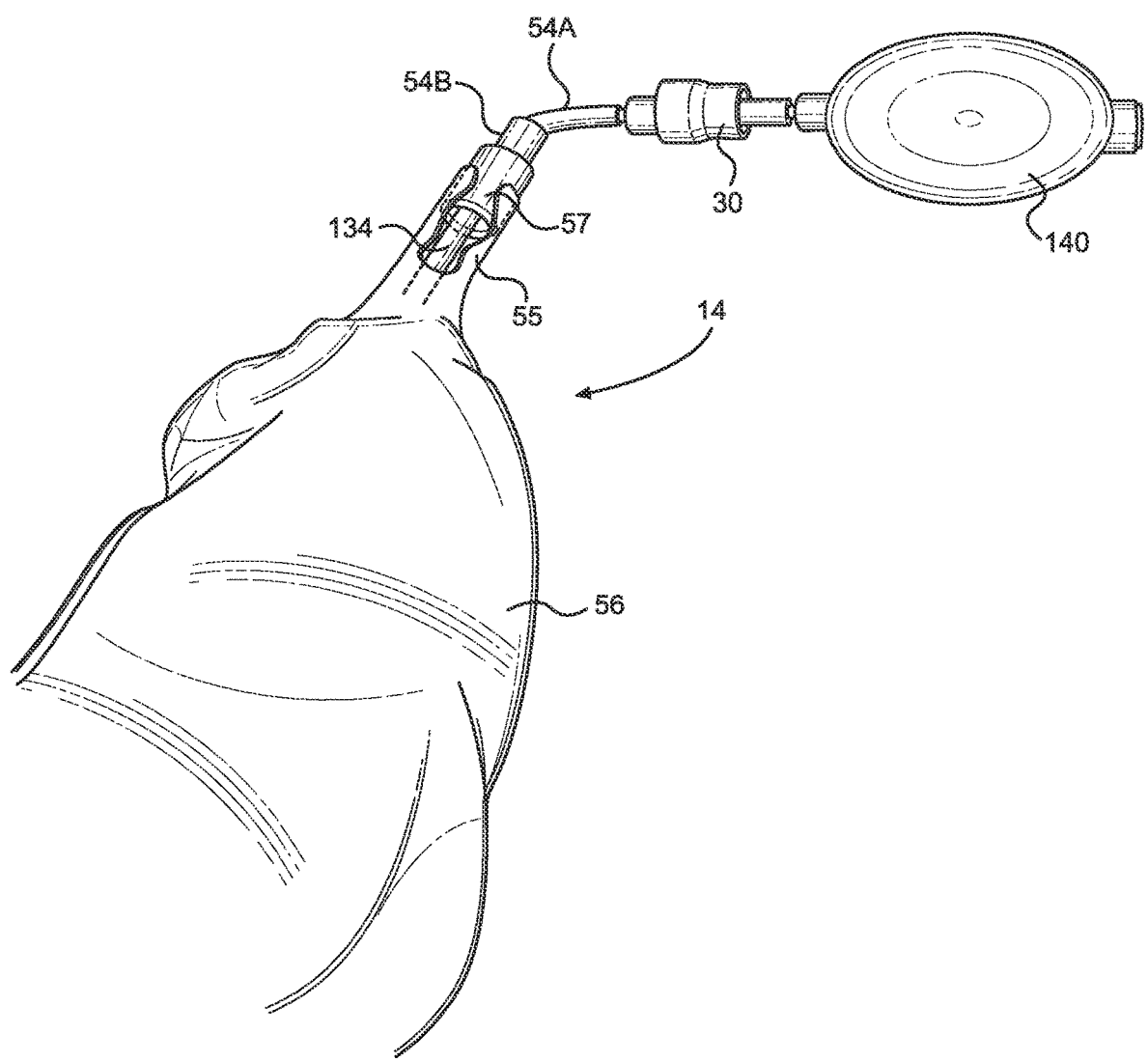
FIG. 34 is a perspective view of the external preservative supply bladder with an inert gas harvesting member during a filling with air.

One or more preservative gas production members 134 can be selectively inserted into and, potentially, removed from the inner volume of the bladder 14. With such a preservative gas production member 134 inserted directly into the inner volume of the bladder 14, the bladder 14 can simply be filled with a volume of ambient oxygen-rich air, and that air can be converted to oxygen-poor air, mainly nitrogen, by use of $CO_2$ and/or oxygen absorbing materials forming all or part of the inter gas production member 134. With sufficient time and $CO_2$ and/or oxygen absorbing material, the resulting gas within the bladder 14 will thus be a preservative gas that can be used pursuant to the disclosed method. The bladder 14 can be filled with air in any effective manner. For example, as FIG. 34 shows, the bladder 14 could be inflated with ambient air by a simple manual air pump 140, in this case a squeeze-bulb pump, or any other type of filling mechanism.

The preservative gas production member 134 could, by way of example, retain a volume of material 136 with $CO_2$ absorbing capacity, such as calcium hydroxide and, additionally or alternatively, a volume of material 136 with oxygen absorbing capacity, such as oxygen-absorbing iron or a mixture of iron powder and sodium chloride. It would be possible for the preservative gas production member 134 or multiple separate or combined members to be disposed in the inner volume of the bladder 14 in a fixed or a free-floating manner. If necessary or desirable, the preservative gas production member or members 134 can be removed and replaced when the materials are spent.

So configured, the preservative gas production member 134 can transform air retained in the inner volume of the bladder 14 that is initially composed of, for example, 79% nitrogen, 20% oxygen, 0.5% argon, and 0.5% trace other gases into an environment mainly composed of nitrogen with a small percentage of argon and a very small volume of oxygen, such as 0.1% or less. After a given time period, such as approximately eighteen hours in one practice of the invention, the transformation results in a reduction in volume of the contained gases so that the bladder 14 will naturally tend to compress from the initial condition to a partially compressed condition. Losses of volume of approximately 20% have been exhibited. The inner volume of the bladder 14 will thus retain a preservative gas comprised nearly entirely of nitrogen and argon pending use in the volumetric displacement method taught herein.

Figure 31:
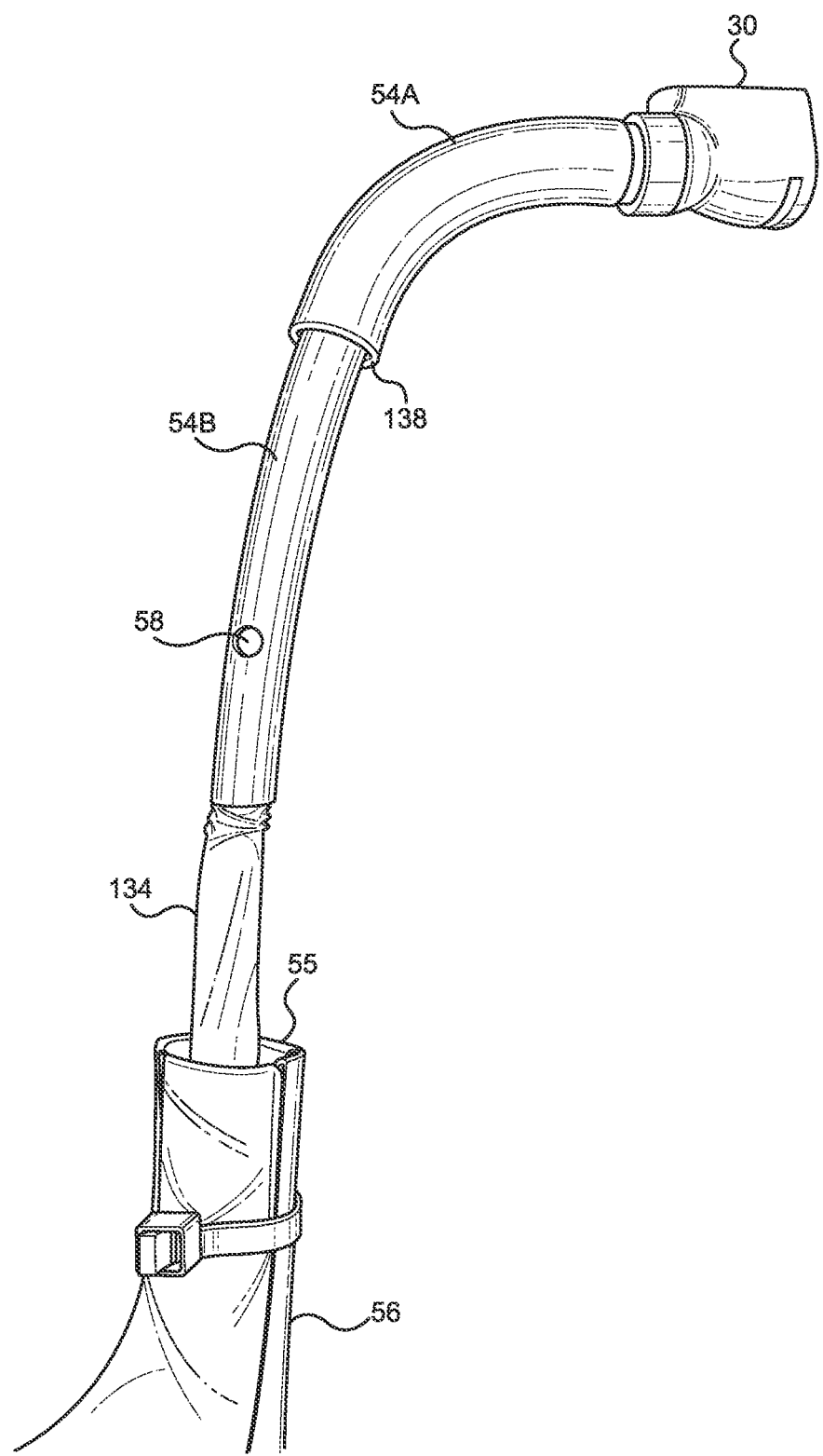
FIG. 31 is an amplified view in front elevation of a distal portion of the external preservative supply bladder with an inert gas harvesting member of FIG. 30.
Figure 33:
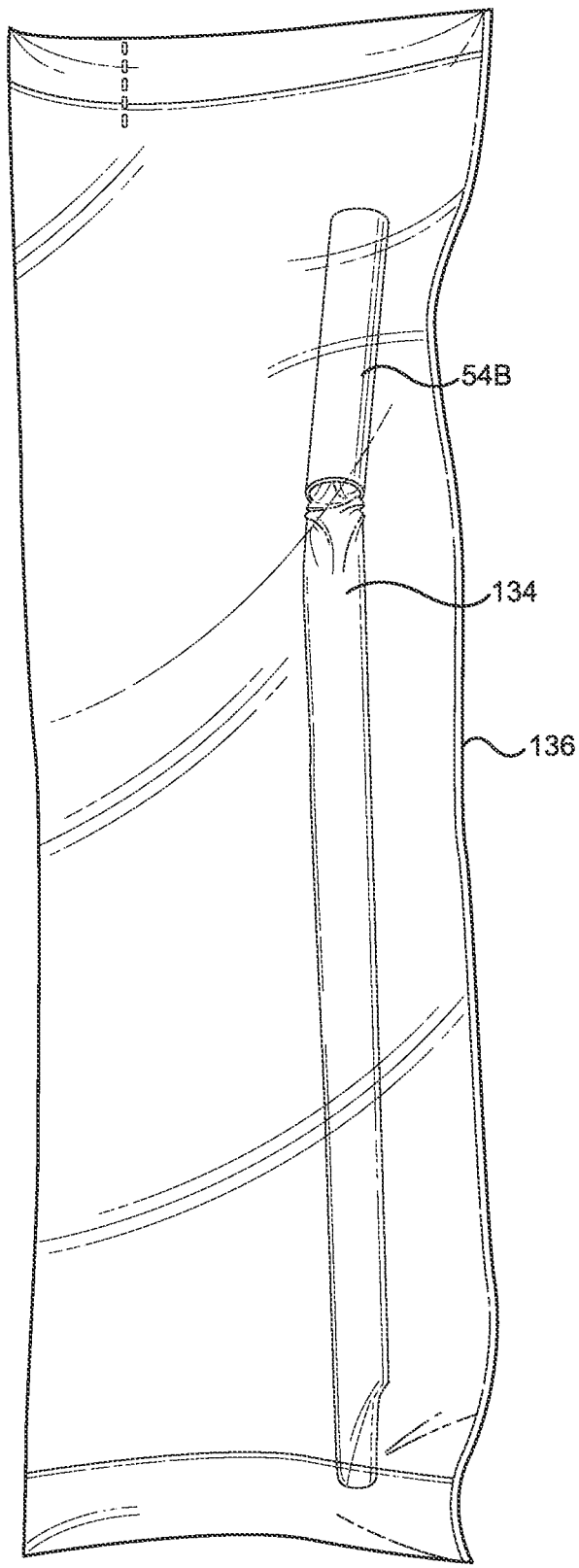
FIG. 33 is a view in front elevation of the inert gas harvesting member in sealed packaging.

In the present embodiment, the preservative gas production member 134 comprises an elongate member that is generally rod-like in shape. The preservative gas production member 134 has an effective diameter sized to be received through the orifice 55 in the bladder 14 and sized to be received into the proximal end of the second tube 55B in an interference fit. With this, the preservative gas production member 134 can be engaged with the proximal end of the second tube 55B as is depicted in FIG. 31, for instance, and the preservative gas production member 134 and the proximal end of the second tube 55B can be inserted through the orifice 55 and into the inner volume of the bladder 14. The preservative gas production member 134 could, in certain examples of the invention, be formed with a sleeve of, for example, thin lamina, paper, or plastic capable of freely allowing gas exchange between the chemical substance or substances inside the sleeve and the inner volume of the bladder 14. In practice, such preservative gas production members 134 can be stored pending use in a vacuum-sealed sleeve 136 as is shown, for instance, in FIG. 33.

Figure 32:
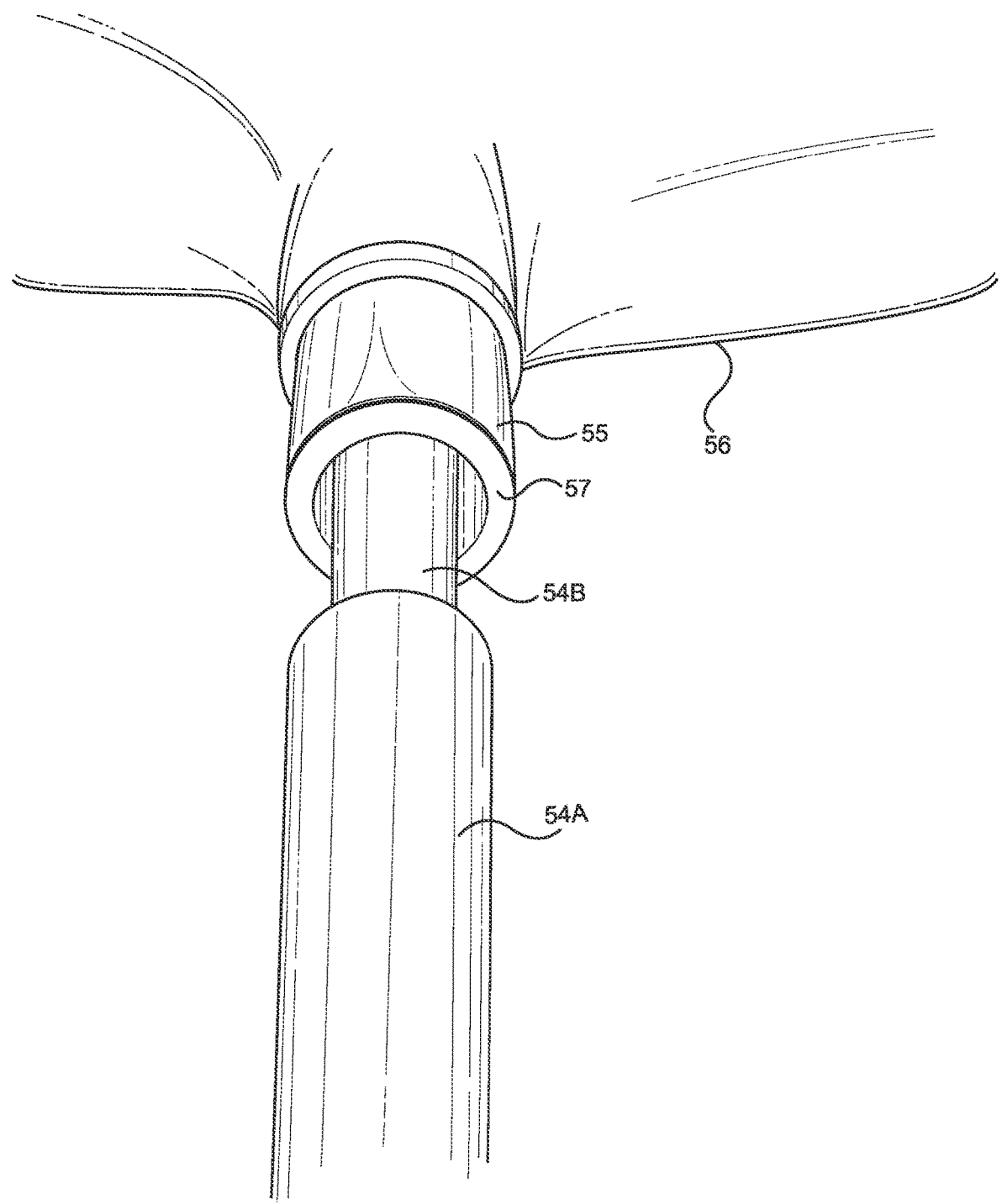
FIG. 32 is an amplified perspective view of a distal portion of the external preservative supply bladder with an inert gas harvesting member showing engagement between the first and second tubes and the collar of the orifice of the supply bladder.

As seen in FIG. 32, for instance, the orifice 55 of the bladder 14 can have a collar 57. The collar 57 can have an inner diameter sized to produce an interference fit between the collar 57 and the outer diameter of the first tube 54A. With that, the preservative gas production member 134 and the proximal portion of the second tube 54B can be slid through the orifice 55 and into the inner volume of the bladder 14, and the proximal portion of the first tube 54A can be received into the collar 57 in a substantially sealed relationship. With the preservative gas production member 134 so disposed, simple ambient air can be converted to a volume of gas mainly composed of nitrogen with a small percentage of argon and a very small volume of oxygen, and the bladder 14 can be used in the preservative process disclosed herein. When desired, such as when some or all of the preservative gas has been dispensed into a bottle 200, the spent preservative gas production member 134 can be removed and replaced simply by pulling the tube structure formed by the first and second tubes 54A and 54B from the collar 57, removing the preservative gas production member 134 from the proximal end of the second tube 54B, and inserting a new preservative gas production member 134 to permit a repetition of the process. It would also be possible to use the bladder 14 just shown and described to replenish a deflated second bladder (not shown) with preservative gas.

Yet another structure of a bladder for use in the volumetric displacement process disclosed herein is indicated generally at 14 in FIGS. 35A through 35D. There, the bladder 14 again defines an open inner volume for retaining a volume of gas. The bladder 14 is again sealed but for the orifice 55. Here, however, the bladder 14 is defined by a wall structure with at least one flexible portion 56A that can expand and contract or collapse and at least one substantially rigid portion 56B that resists contracting or collapsing. The flexible and rigid portions 56A and 56B could be formed from any airtight materials. For example, the flexible portion 56A could be of a polymeric and foil layered material, and the rigid portion 56B could be formed from metal, plastic, or any other suitable material or combination of materials.

In the depicted embodiment, the flexible and rigid portions 56A and 56B each comprise roughly one-half of the overall bladder shape, which of course could vary widely within the scope of the invention. In this example, the rigid portion 56B forms a bulbous rigid shell portion that includes the orifice 55, and the flexible portion 56A, when expanded, forms a bulbous flexible shell portion. The flexible and rigid portions 56A and 56B are mutually sealed along their edges to define a sealed inner volume.

Figure 35A:
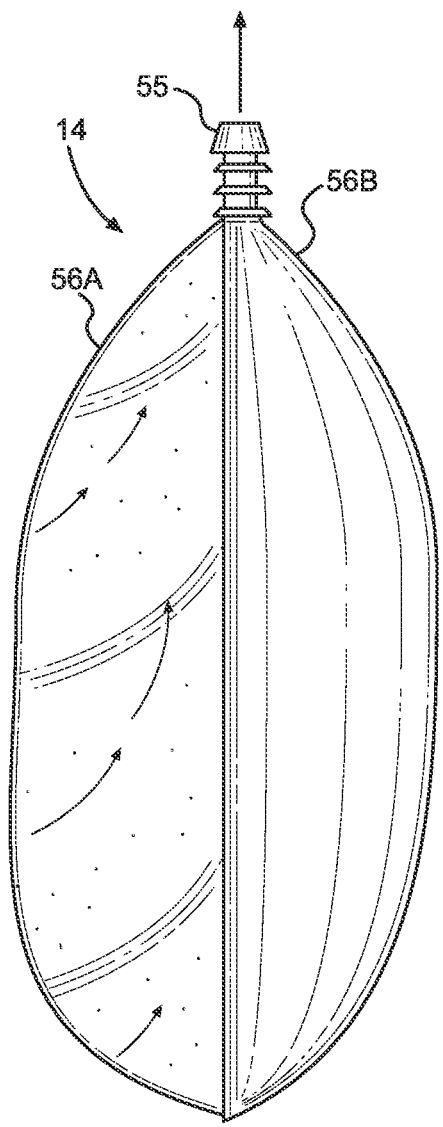
FIGS. 35A through 35D depict an alternative external preservative supply bladder in sequential stages of deflation.
Figure 35B:
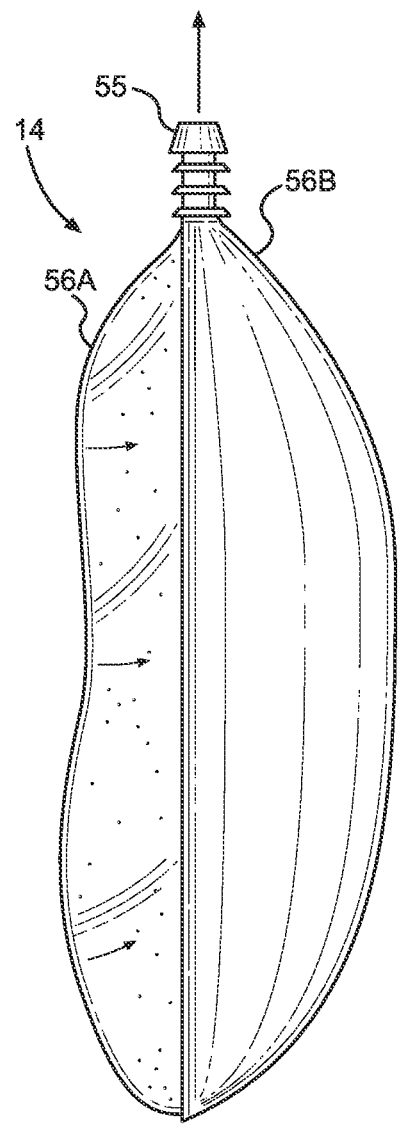
Figure 35C:
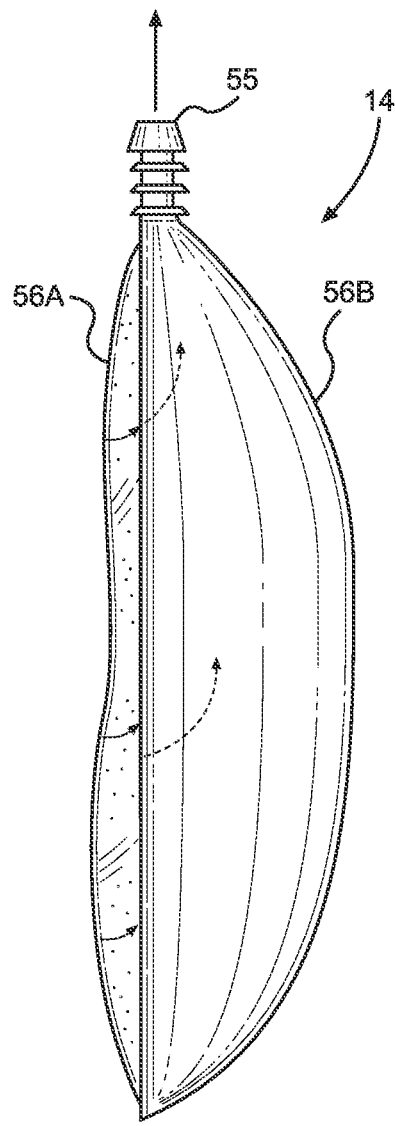
Figure 35D:
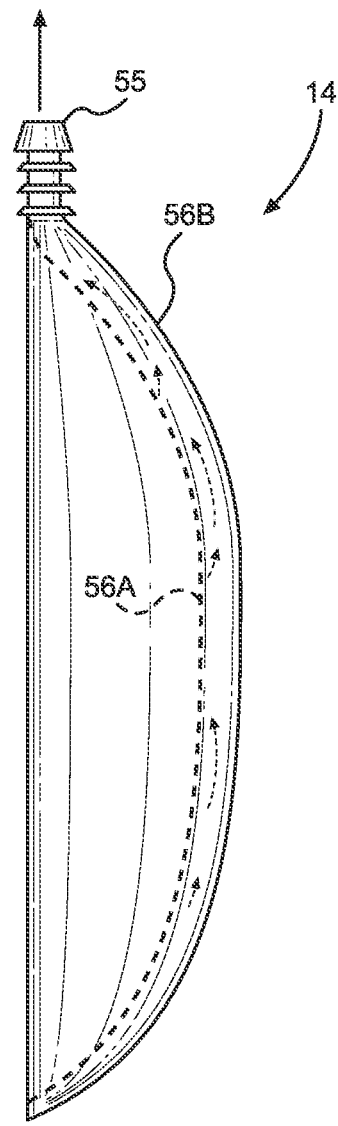

With a bladder 14 formed with such flexible and rigid portions 56A and 56B, the bladder 14 can transition between the inflated state of FIG. 35A and the substantially deflated state of FIG. 35B. As the bladder 14 undergoes deflation, for example, the flexible portion 56A will begin as a bulbous shape as in FIG. 35A so that the flexible and rigid portions 56A and 56B will generally correspond in shape. With progressive degrees of deflation of the bladder 14, the rigid portion 56B will retain its shape, but the flexible portion 56A will tend to collapse toward the rigid portion 56B through the progressively collapsed configurations of FIGS. 35B and 35C to the substantially collapsed configuration of FIG. 35D where the flexible portion 56A has bowed in to the concavity of the rigid portion 56B.

Figure 36:
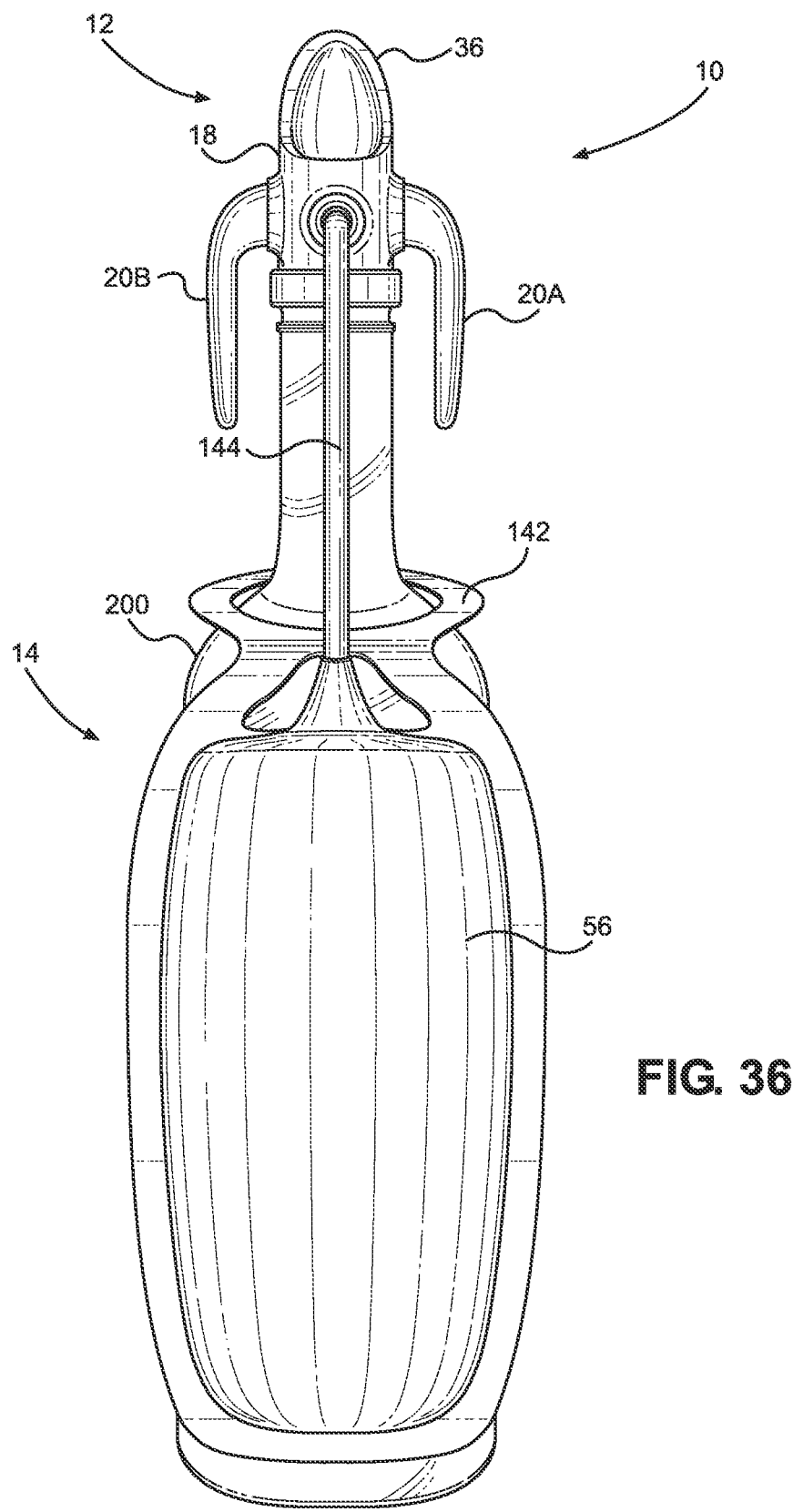
FIG. 36 is a view in front elevation of another volumetric displacement preservation system according to the invention with an alternative external preservative supply bladder and an alternative fluid exchange structure.
Figure 37:
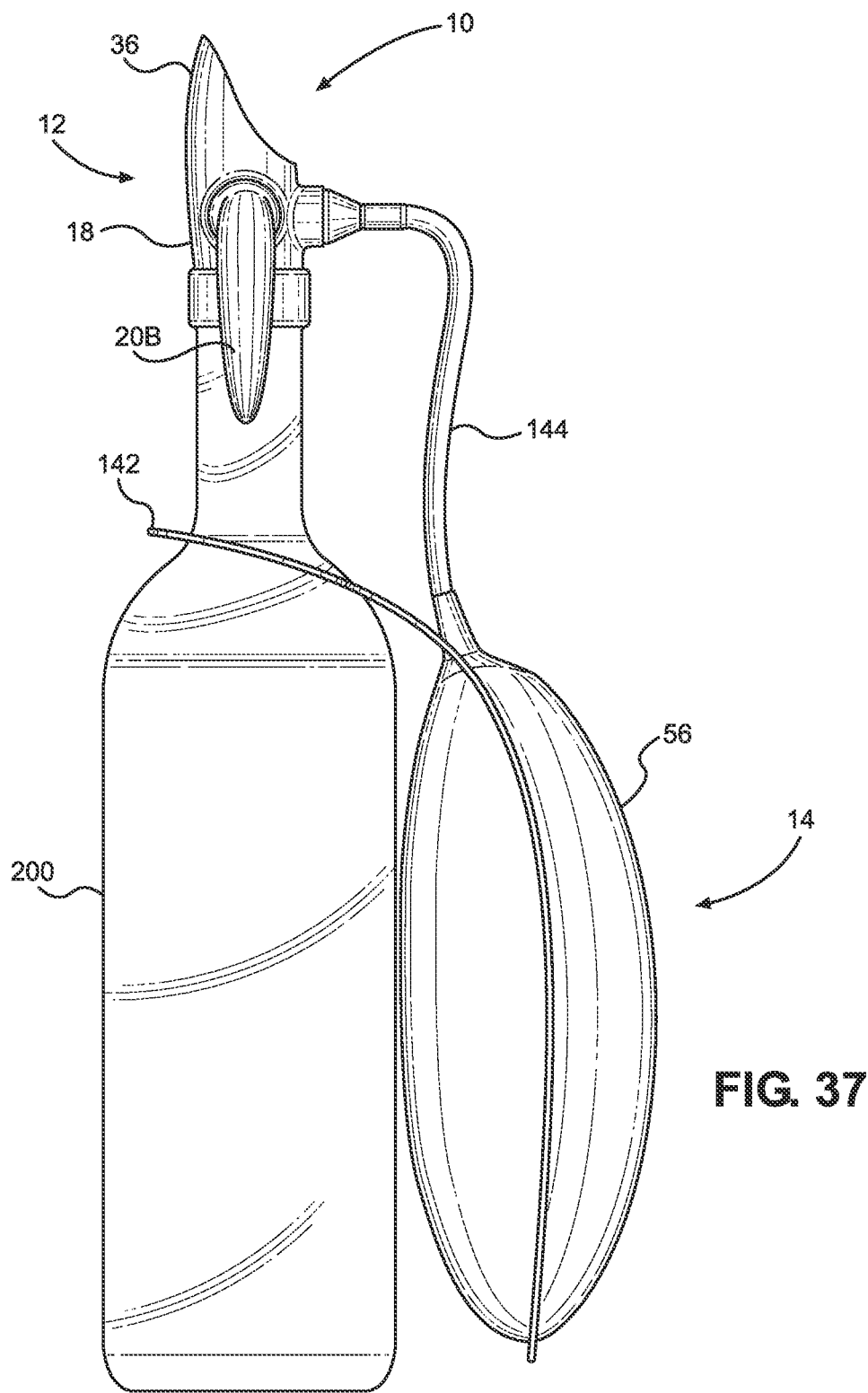
FIG. 37 is a view in side elevation of the volumetric displacement preservation system of FIG. 36.
Figure 38:
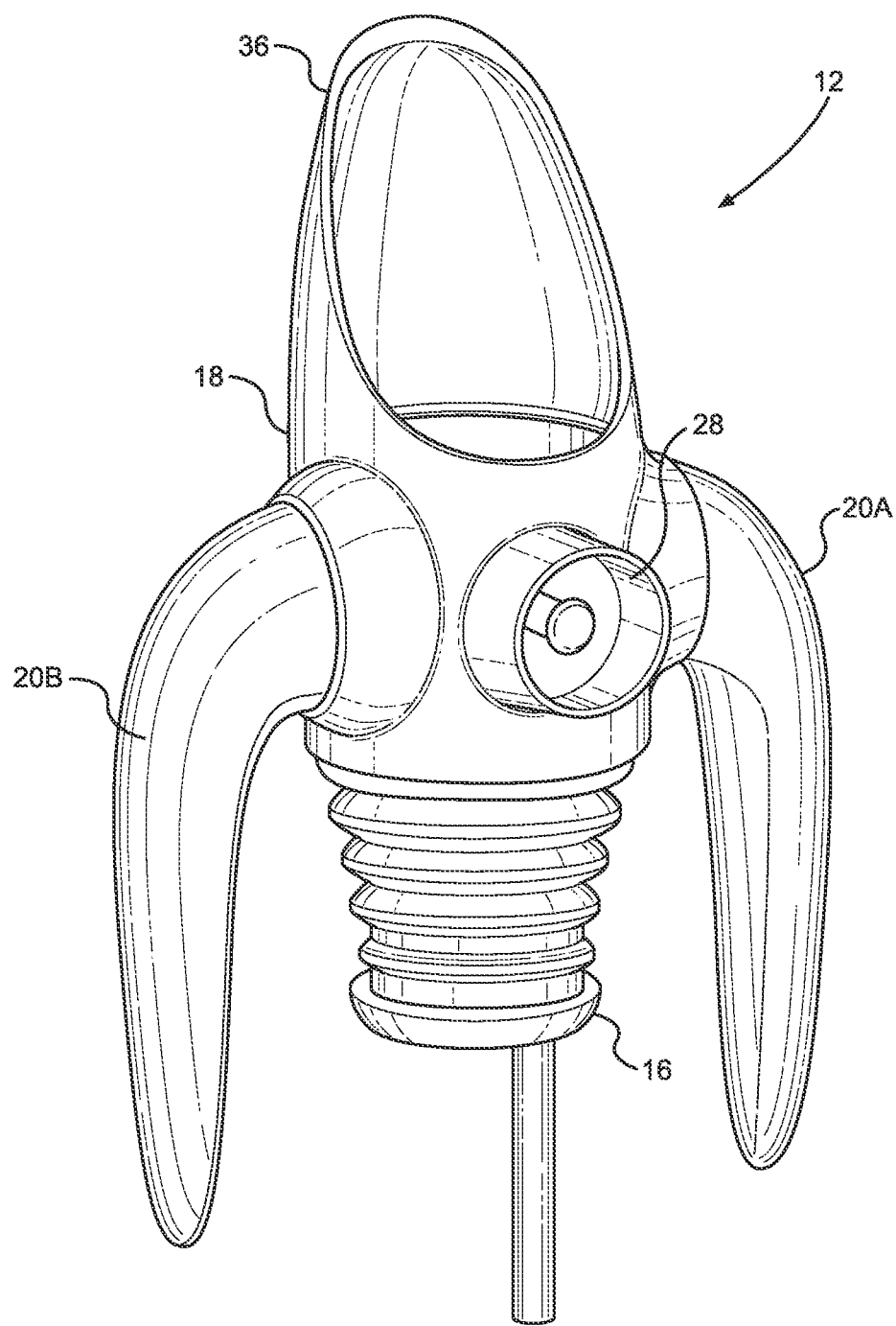
FIG. 38 is a perspective view of the fluid exchange structure of FIG. 36.
Figure 39:
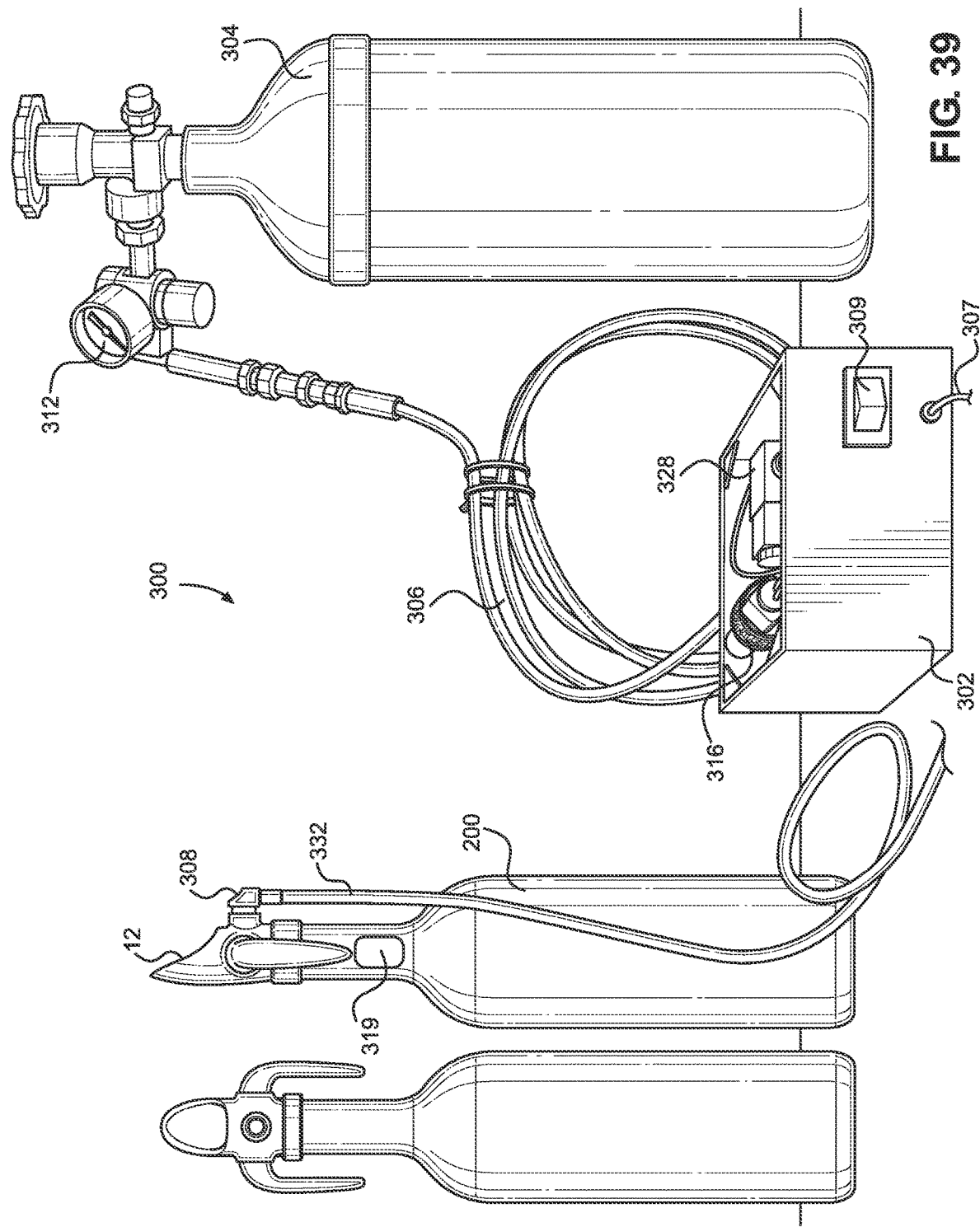
FIG. 39 is a perspective view of an automatic preservative gas replenishing system according to the invention.
Figure 40:
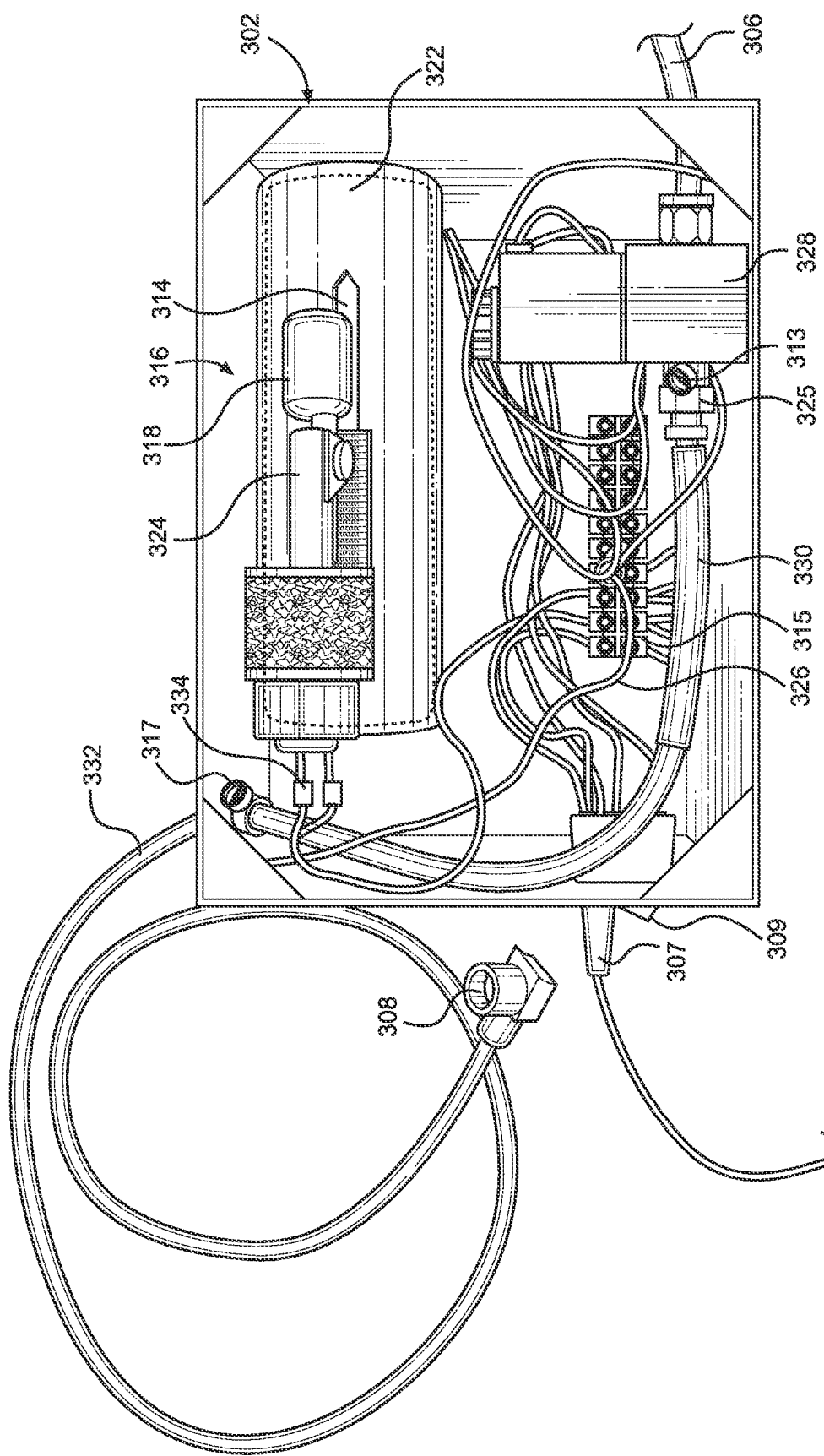
FIG. 40 is a top plan view of the housing of the automatic preservative gas replenishing system.
Figure 41:
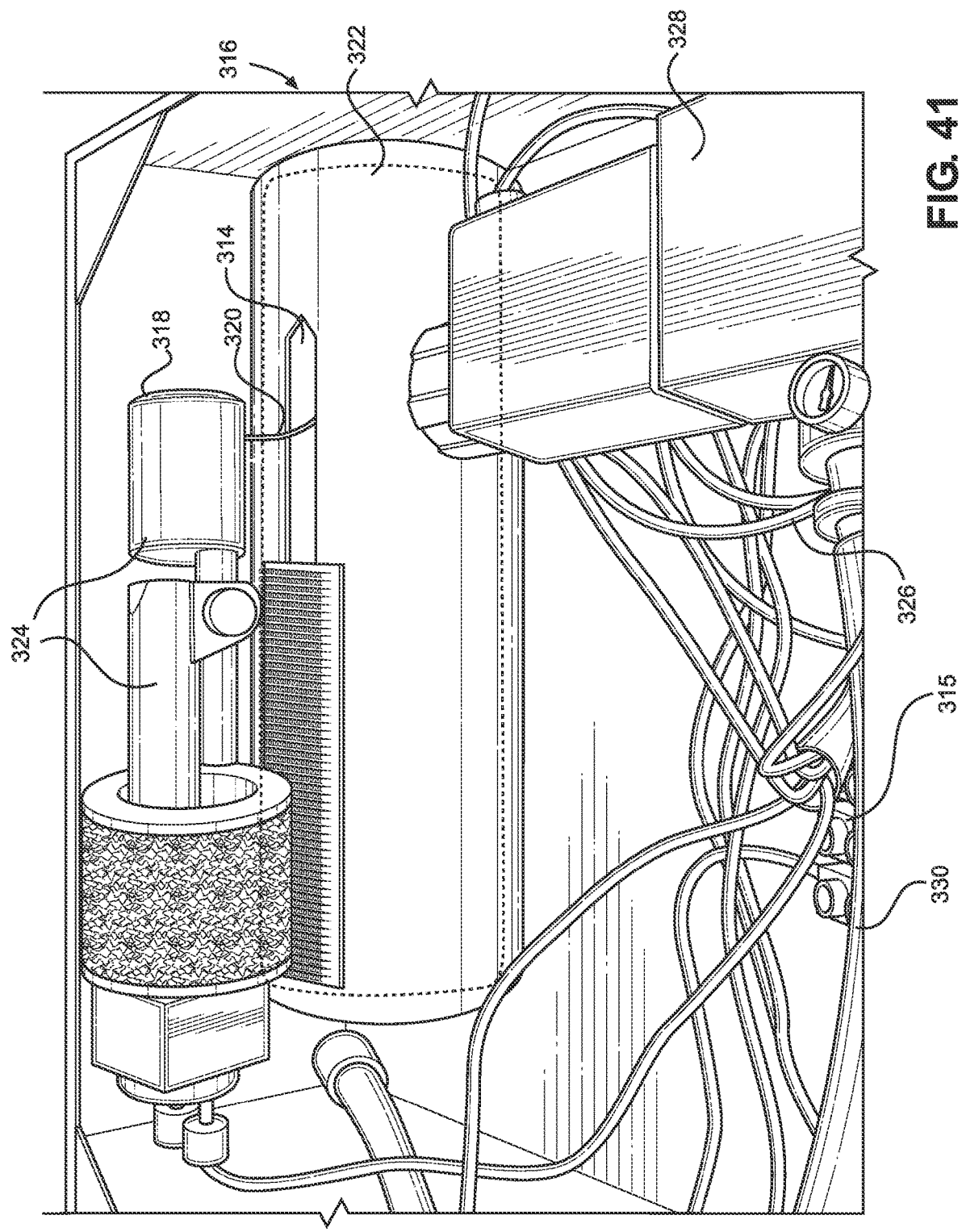
FIG. 41 is a perspective view of an actuation mechanism for the automatic preservative gas replenishing system in an actuated condition.
Figure 42:
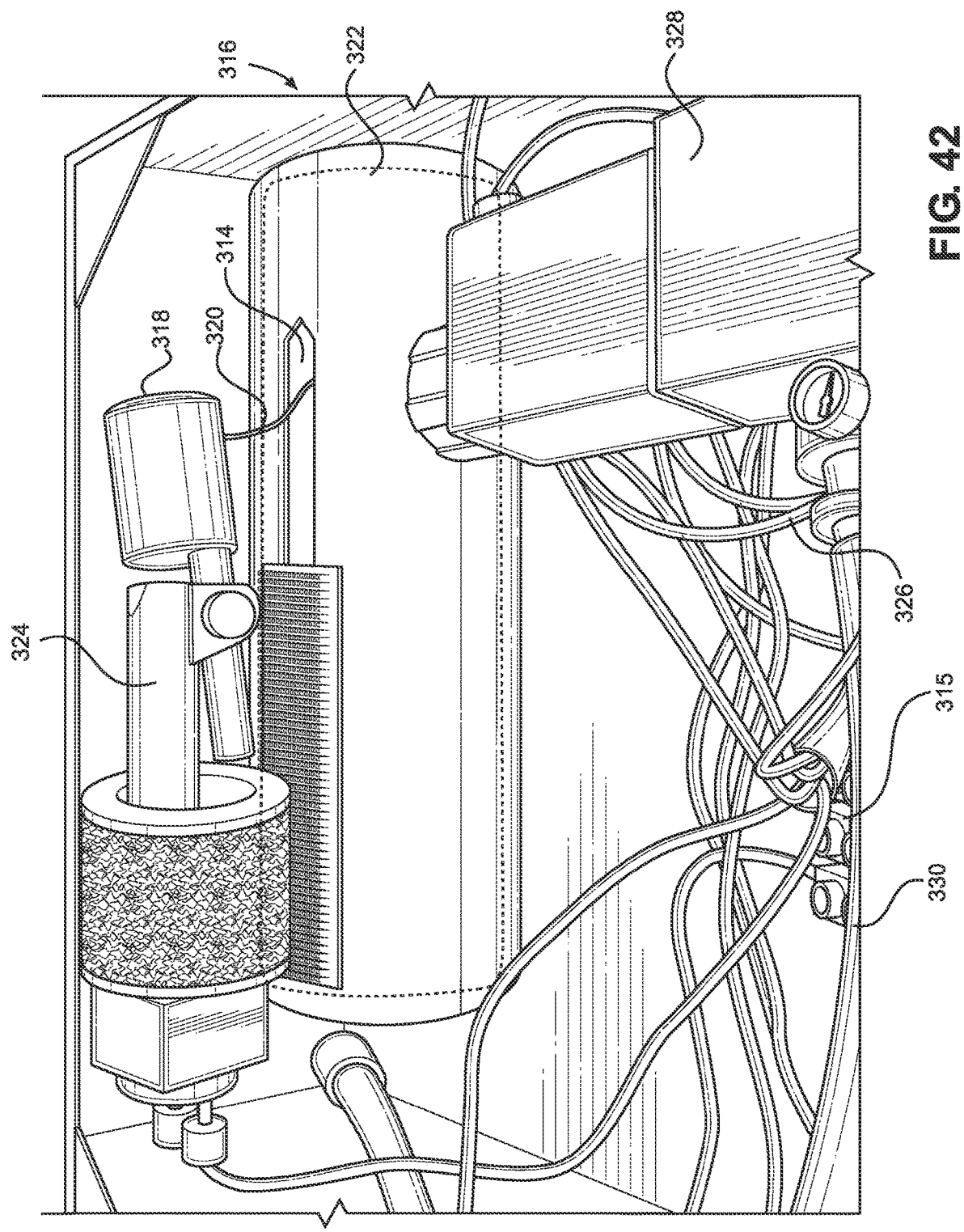
FIG. 42 is a perspective view of the actuation mechanism for the automatic preservative gas replenishing system in non-actuated condition.

An alternative embodiment of the volumetric displacement system 10 is shown in FIGS. 36 and 37, and the fluid exchange structure 12 thereof is shown apart in FIG. 38. There, the fluid exchange structure 12 again selectively and, potentially in a substantially simultaneous event, establishes and closes the inlet and exhaust pathways previously described. The fluid exchange structure 12 again has a stopper 16 with a plurality of annular sealing ridges 22 therealong that cooperate to create a sealing engagement with the vessel 200 and a head portion 18 accessible from external to the vessel 200. The fluid exchange structure 12 has a dispensing nozzle 36 that projects longitudinally to be aligned with the neck of the bottle 200. In a manner as shown and described previously, the fluid exchange structure 12 is operable by a pivoting of either or both of first and second lever arms 20A and 20B.

The lever arms 20A and 20B are substantially equal in size and shape with each having a smooth, arcuate shape that tapers to a tip. With this, the arms 20A and 20B are operative as stabilizing legs when in an orthogonal position. With that, a bottle 200 or other vessel can be stably rested on a support surface with the arms 20A and 20B cooperating to support the upper end of the bottle 200. Each arm 20A and 20B can have a length from its pivot axis to its distal end calibrated to correspond to the radius of the base of a typical wine bottle 200 such that the bottle 200 could be retained horizontally or at some desired angle of incline or decline.

Preservative gas is again supplied to the inner volume of the vessel 200 during a dispensing of liquid 202 from an expandable and compressible bladder 14. The bladder 14 is founded on a shell 56 of a flexible and substantially gas impermeable material as described previously. Here, however, the bladder 14 is fluidically coupled to the fluid exchange structure 12 by an elongate tube 144 such that the shell 56 of the bladder is spaced from the fluid exchange structure. The bladder 14 has a collar portion 142 secured to the shell 56. The collar portion 142 can thus be employed to surround the bottle 200 thereby to assist in retaining the bladder 14 in place. The collar portion 142 can comprise a disc or other ring of material and could include an inner volume for retaining air or produced preservative gas. For example, all or a portion of the shell 56 could be incorporated into an annular shape to form the collar portion 142 with the shell 56 potentially having, for example, a torroidal shape or a sleeve or jacket with an inner volume. The collar portion 142 is illustrated in FIGS. 36 and 37 as comprising a simple ring.

As noted above, while the foregoing systems and methods are highly advantageous, one of the present inventors has appreciated that there are circumstances where continually refilling or replacing preservative gas within a compressible bladder can be inconvenient or where greater volumes of preservative gas may be required than can be practically retained in a bladder retaining a given volume of gas. By way of example and not limitation, in bars, restaurants, and other locations where there is a continual high demand for preservative gas from the compressible reservoir to preserve the wine in multiple wine bottles concomitantly, it is desirable to be able to replenish preservative gas in a compressible bladder consistently and automatically. However, it is further recognized that, although the compressible bladder must be consistently replenished to provide an available supply of preservative gas, the introduction of excess pressure into the bladder that would interfere with the drawing of gas from the bladder and into the vessel under the natural force of gravity in non-pressurized volumetric displacement of the vessel contents. Pressurization of the preservative gas in the compressible bladder would cause the vessel contents to tend to be ejected under pressure, much as is undesirably the case with prior art pressurized preservation systems and methods.

With an awareness of the foregoing needs and requirements, one of the present inventors devised of a system for automatically replenishing preservative gas within a compressible bladder for supply to the inner volume of a vessel in volumetric displacement as the contents of the vessel are dispensed under the natural force of gravity. The system can be understood with reference to FIGS. 39 through 45 where embodiments of the system are indicated generally at 300. The system 300 can be considered to be founded on a system housing 302 that is, during operation of the system 300, coupled to a source of compressed preservative gas, in this case a compressed gas tank 304, through a supply conduit 306 to receive preservative gas from the tank 304. The system 300 is capable of providing preservative gas to an inner volume of a vessel 200 through a discharge conduit 332 that can be selectively coupled to a fluidic connector 28 of a fluid exchange structure 12 via a fluidic connector 308 disposed at a distal end of the discharge conduit 332. The discharge conduit 332, which may alternatively be referred to as a distribution conduit 332, is connected to a fluidic connector 346 comprising an output port disposed to receive preservative gas from the compressible bladder 314.

The fluidic exchange structure 12 can be generally according to embodiments disclosed hereinabove. Accordingly, for efficiency of the present disclosure, certain components of the system 300 will be described with combined reference to the previously-described drawings. With reference to FIGS. 1 through 16 and 45, for example, wherein the fluid exchange structure is indicated at 12, the fluid exchange structure 12 can likewise have a stopper 16 with a plurality of annular sealing ridges 22 therealong that cooperate to create a sealing engagement with the vessel 200, in this case with the neck 206 of the wine bottle 200. While separate valves could be provided within the scope of the invention for opening and closing inlet and exhaust pathways of the fluid exchange structure 12, one depicted embodiment provides a fluid exchange valve 32 that has a first condition, depicted in FIGS. 2A and 2B, wherein the inlet and exhaust pathways are substantially sealed and a second condition, depicted in FIGS. 3A and 3B, wherein the inlet and exhaust pathways are opened.

Preservative gas is supplied to the inner volume of the vessel 200 through the inlet pathway during a dispensing of liquid 202 from an expandable and compressible bladder, which is indicated at 314 in FIGS. 39 through 45. There, the bladder 314 in this embodiment comprises an expandable and compressible shell that is disposed within a sub-housing 322 that generally corresponds in size and shape with a fully expanded size and shape of the bladder 314. The shell of the bladder 314 is of a flexible and substantially gas impermeable material. Again, numerous such materials are possible, each within the scope of the invention. In one embodiment, for example, the shell of the bladder 314 can be a flexible polymeric material with or without a lining layer. The material defining the shell 314 could, for example, comprise a foil formed by one or more layers of polymeric material with an aluminum lining. The bladder 314 and the sub-housing 322 are disposed within the main housing 302. The bladder 314 is fluidically connected, such as through an aperture, to a preservative gas supply conduit 330 that receives preservative gas from the compressed preservative gas tank 304 through a flow control subsystem 328, which may alternatively be referred to as a valve system 328. The bladder 314 is fluidically connected, such as through the same or a different aperture, to the discharge conduit 332 to provide gas in a volumetric displacement process to a vessel 200 through the fluidic connector 308 coupled to the fluid exchange structure 12.

The fluid exchange valve 32 can be pivoted from a first, closed position with the dispensing nozzle 36 orthogonal to a longitudinal axis of the stopper 16 and a second, open position with the dispensing nozzle 36 in line with the longitudinal axis of the stopper 16. The fluid exchange valve 32 could be manipulated between the first and second positions by, for instance, first and second lever arms 20A and 20B that are fixed to pivot with opposed ends of the base portion 34. The stopper 16 has a liquid exhaust conduit 24 and a gas inlet conduit 26. Orientation of the fluid exchange valve 32 in the closed position as in FIGS. 2A, 2B, and 4 will cause the solid wall portions 42 and 44 of the fluid exchange valve 32 to seal the ends of the liquid exhaust conduit 24 and the gas inlet conduit 26 of the stopper 16, and the dispensing nozzle 36 will be disposed in a storage position against the radially communicating lower surface of the valve positioning pathway 50. With that, the inner volume of the vessel 200 is sealed; liquid cannot be exhausted, and gas cannot enter. Adjustment of the fluid exchange valve 32 to the open position rotates the solid wall portions 42 and 44 out of alignment with the conduits 24 and 26. The conduit joining channel 46 and the conduit joining passageways 48A and 48B are rotated into the positions illustrated. An open fluidic inlet pathway is provided from the inner volume of the vessel 200, through the conduit 26, the conduit joining channel 46, the distal conduit portion 40, and the valve coupling 28. Simultaneously, an open fluidic exhaust pathway is created from the inner volume of the vessel 200, through the conduit 24, the conduit joining passageways 48A and 48B, and the dispensing nozzle 36. With the fluidic pathways open and the fluid exchange structure 12 coupled to the compressible bladder 314 through the fluidic connector 308 and the discharge conduit 332 of the system 300 during operation as disclosed herein, liquid exhausted through the open exhaust pathway will naturally draw in and be replaced by preservative gas drawn into the inner volume of the vessel 200 through the open inlet pathway from the compressible bladder 314.

In preferred practices of the invention, the volume of preservative gas in the compressible bladder 314 is retained substantially at ambient pressure. As liquid in a vessel 200 is displaced with preservative gas received from the bladder 314, the volume of preservative gas in the compressible bladder 314 will tend to be depleted. As taught herein, the compressible bladder 314 is automatically replenished with preservative gas substantially at ambient pressure under operation of an inflation detection system 316. The inflation detection system 316 has a first condition wherein replenishing preservative gas is not supplied to the compressible bladder 314 and a second condition wherein replenishing gas is supplied to the compressible bladder 314. The first condition can be a condition wherein the compressible bladder 314 is inflated with preservative gas to a certain predetermined state of inflation, and the second condition can be a condition wherein the compressible bladder 314 is inflated with preservative gas below the predetermined state of inflation. The inflation detection system 316 is operative to detect when the compressible bladder 314 has reached the predetermined state of inflation. In embodiments of the invention, the compressible bladder 314 can be considered to have a fully inflated condition, and the inflation detection system 316 detects when the compressible bladder 314 is inflated to the fully inflated condition or to within a predetermined range of the fully inflated condition. By way of example and not limitation, the inflation detection system 316 can detect when the bladder 314 is inflated with preservative gas at or above a threshold inflation level.

After reviewing the present disclosure, one skilled in the art may appreciate a plurality of different mechanisms that would operate as inflation detection systems 316 to detect when the compressible bladder 314 is inflated to the predetermined state of inflation. Each such mechanism is within the scope of the invention except as it may be expressly limited by the claims. Inflation detection mechanisms could comprise mechanical systems, optical systems, electro-mechanical systems, sound-activated systems, movement sensors, light sensors, and any other type of system effective to detect when the compressible bladder 314 is inflated to a predetermined state of inflation.

In the present example of the invention, the inflation detection system 316 comprises an electro-mechanical system for detecting when the bladder 314 is filled to the predetermined state of inflation. The inflation detection system 316 has a contact member 320 disposed to contact the compressible bladder 314 through an aperture in the sub-housing 322. The contact member 320 is fixed to a deflection switch 318 that is supported by a retaining member 324. Here, the deflection switch 318 is pivotally connected to the retaining member 324, but it would be readily possible for the deflection switch 318 to be otherwise movably coupled to the retaining member 324, such as by being positioned to be depressed, rotated, or otherwise actuated. The contact member 320 could, for instance, be fixed to the deflection switch 318, or the contact member 320 could be a portion of the deflection switch 318. The deflection switch 318 and the contact member 320 are biased, such as by spring force, under the force of gravity, by resiliency, or any other biasing method or combination thereof toward the compressible bladder 314.

The deflection switch 318 has an activated state when the deflection switch 318 is moved, such as by pivoting, extension, or other movement, in an inward direction toward the inner volume of the compressible bladder 314. The deflection switch 318 is permitted to move inwardly in the direction toward the compressible bladder 314 to the activated state when the volume of preservative gas in the compressible bladder 314 falls below the predetermined state of inflation such that the outside wall of the compressible bladder 314 is in a condition sufficient, such as what might be considered a softened condition, to be deflected and to permit such movement. The deflection switch 318 has a deactivated state when the deflection switch 318 is moved, such as by pivoting, retraction, or other movement in an outward direction away from the compressible bladder 314. The deflection switch 318 is moved outwardly to the deactivated state when the volume of preservative gas in the compressible bladder 314 reaches the predetermined state of inflation such that the outside wall of the compressible bladder 314 is advanced outwardly by the volume of preservative gas in the compressible bladder 314. For instance, where the deflection switch 318 is a pivoting switch as in this embodiment, expansion of the bladder 314 will press the outer wall of the bladder 314 outwardly to pivot the switch 318 to the deactivated state.

When the volume of preservative gas in the compressible bladder 314 falls below the predetermined threshold value, such as below the predetermined state of inflation, the deflection switch 318 moves to the activated state by virtue of the biasing thereof. In the activated state, a valve system 328 fluidically disposed between the source 304 of preservative gas and the compressible bladder 314 is opened to permit preservative gas to flow from the source 304 through the supply conduit 306 and into the compressible bladder 314. When the volume of preservative gas in the compressible bladder 314 reaches the predetermined threshold value, such as at or above the predetermined state of inflation, the deflection switch 318 is moved by the wall of the bladder 314 to the deactivated state. In the deactivated state, the valve system 328 is closed to prevent the flow of preservative gas from the source 304 to the compressible bladder 314.

Over-inflation of the compressible bladder 314 can thus be prevented, such as at or within a given range of the maximum volume of the compressible bladder 314. With that, pressurization of preservative gas within the compressible bladder 314 can be limited, such as not to exceed approximately ambient pressure. It will be understood, however, that embodiments of the invention might calibrate the deflection switch 318 to be induced to the actuation condition at some other predetermined inflation condition or pressure, including potentially a pressure or inflation condition in excess of ambient pressure or to some inflation condition well below the maximum volume of the compressible bladder 314. The valve system 328 can be electrical, mechanical, electro-mechanical, or otherwise configured and constructed.

In the present embodiment, the valve system 328 comprises a solenoid valve that is in electrical communication, such as through electrical connections 326, with the deflection switch 318. The valve system 328 can include a one-way valve. An electrical control system 315, which can include electrical circuitry, electronic memory, wiring, and other electrical control and connection components, cooperates with the inflation detection system 316 to induce the solenoid valve of the valve system 328 to an open condition to permit the flow of preservative gas from the source 304 when the deflection switch 318 is in the activated state. The electrical control system 315 can receive power from a power source 307, which could be a source of alternating current, a source of direct current such as a battery power source, or some other source of electric power. The flow of electrical power from the power source 307 can be controlled by a power switch 309. Accordingly, the solenoid valve of the valve system 328 is induced by the inflation detection system 316 and the electrical control system 315 to a closed condition to prevent the flow of preservative gas from the source 304 when the deflection switch 318 is in the deactivated state. Each of the components referenced herein can be further combined or separated within the scope of the invention.

An electrical circuit is established. In one contemplated embodiment, the solenoid valve of the valve system 328 is electrically opened when the electrical circuit is closed by the deflection switch 328 of the inflation detection system 316 moving to the activated condition. The solenoid valve of the valve system 328 is automatically closed to prevent further filling of the compressible bladder 314 when the electrical circuit is opened by the deflection switch 328 being moved to the deactivated condition, which can be indicative that the compressible bladder 314 is filled to the predetermined state of inflation. In the non-limiting example of the invention where the deflection switch 328 comprises a pivoting switch, an open electrical circuit is established where no electricity flows when the deflection switch 328 is sufficiently pivoted away from the bladder 314 and the solenoid valve of the valve system 328 is in a closed position. When the deflection switch 328 is sufficiently advanced or otherwise moved, such as by pivoting, toward the bladder 314 indicating that the bladder 314 has fallen below the predetermined state of inflation, the electrical circuit is closed to permit the flow of electricity to actuate the solenoid valve of the valve system 328 to an open condition so that preservative gas can flow to fill the compressible bladder 314.

Figure 43:
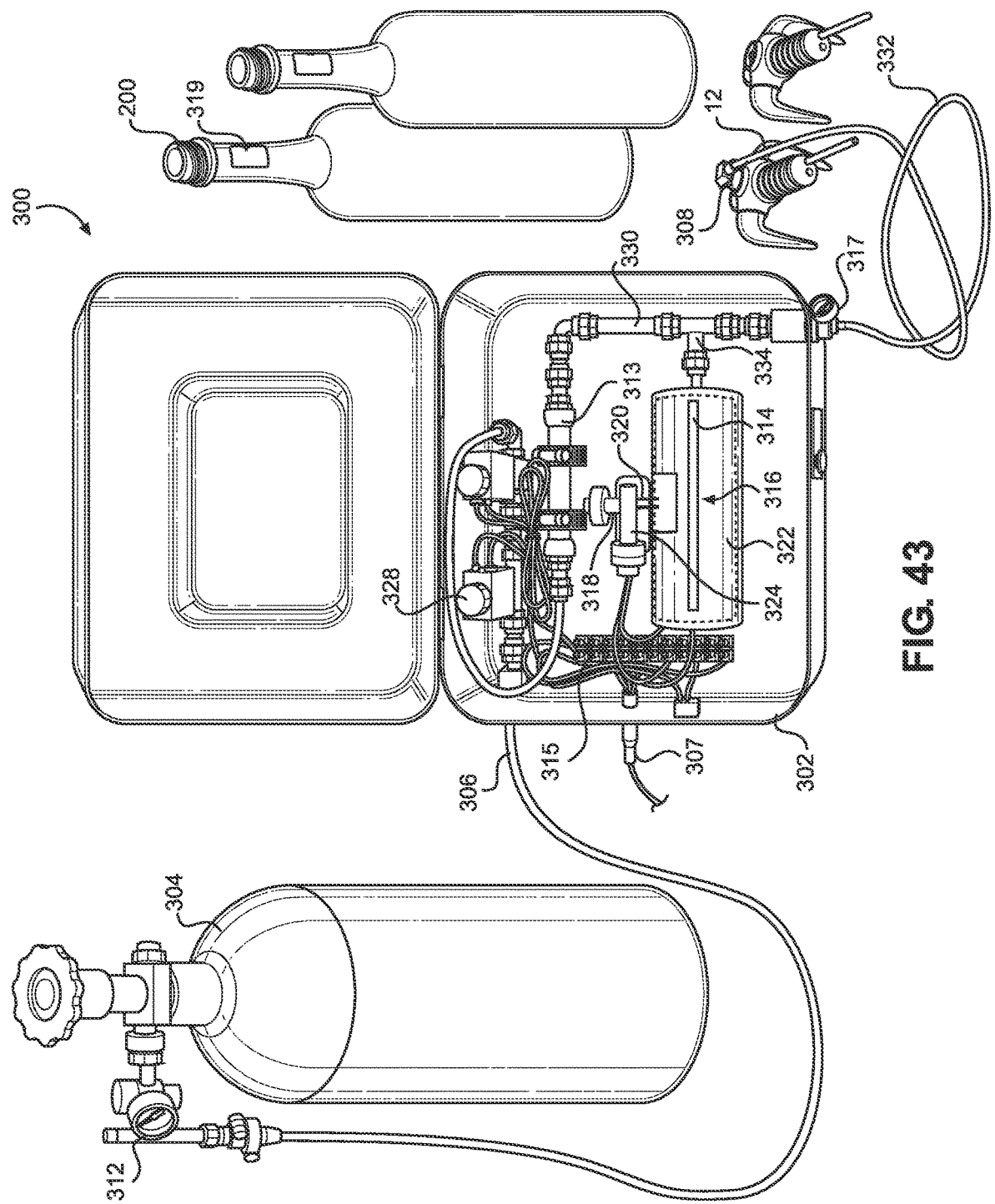
FIG. 43 is a perspective view of an alternative automatic preservative gas replenishing system according to the invention.
Figure 44:
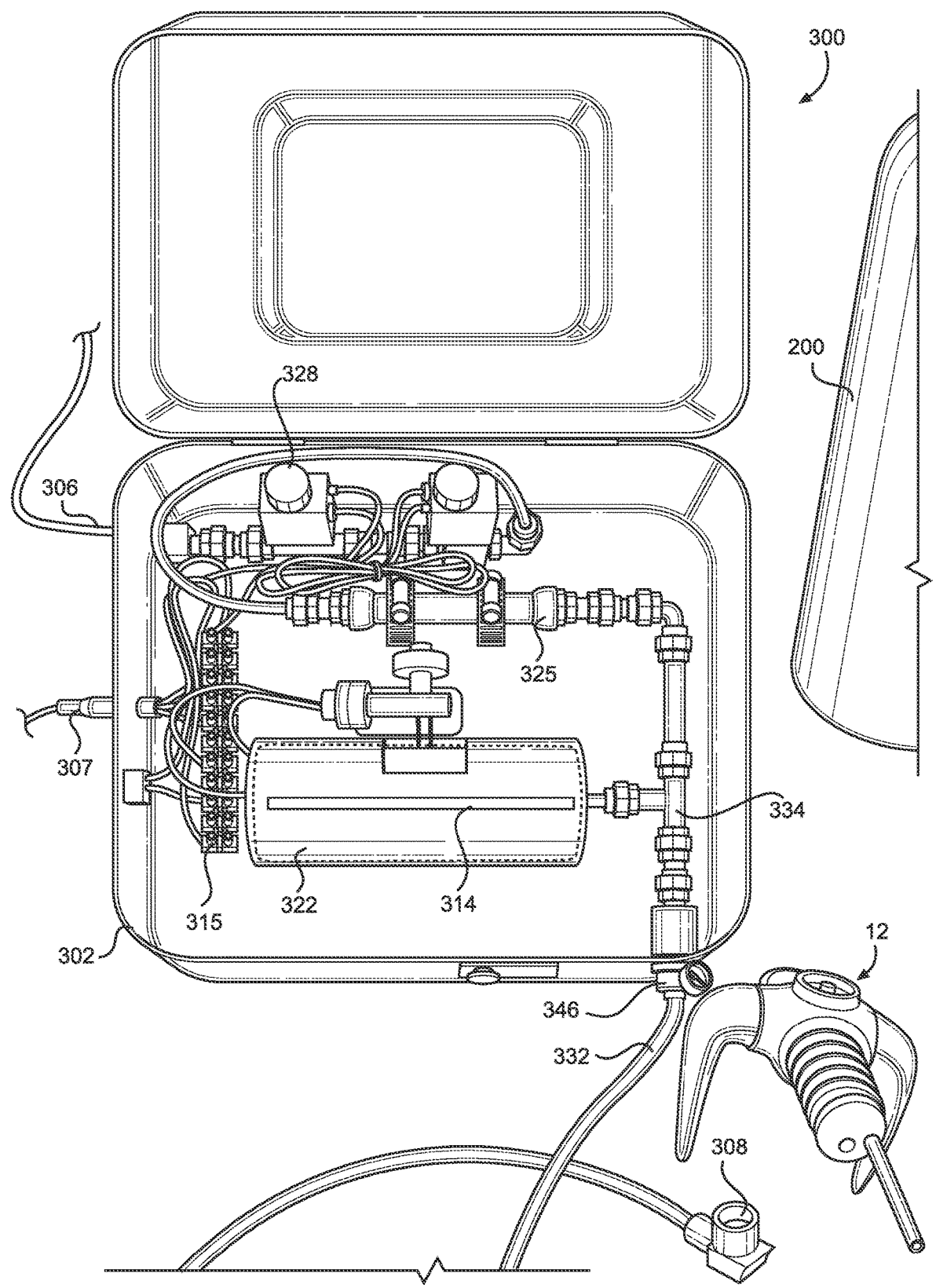
FIG. 44 is a perspective view of the housing of the alternative automatic preservative gas replenishing system of FIG. 43.

It will be understood that numerous possible fluidic connections and connection combinations and configurations could be possible between and including the several components of the fluidic system, including the source 304 of preservative gas through the supply conduit 306, the valve system 328, the conduit 330 fluidically interposed between the valve system 328 and the compressible bladder 314, and the distribution conduit 332 fluidically connected to the valve connector 308. For example, in possible manifestations of the invention, as FIGS. 43 and 44 illustrate, a T-shaped fluidic connector 334 can have a stem of the T-shape fluidically coupled to an orifice of the compressible bladder 314, a first arm of the T-shape connected to the source 304 of preservative gas through conduit 330 with the valve system 328 interposed therebetween, and a second arm of the T-shape fluidically connected to the distribution conduit 332. Preservative gas from the source 304 can thus be automatically supplied to the bladder 314 when the valve system 328 is triggered to an open condition by the switch 328, and preservative gas substantially at ambient pressure can be supplied from the compressible bladder 314 through the distribution conduit 332 when the valve connector 308 is connected to a fluid exchange structure 12 that is received into the neck of a vessel 200.

Even when the valve system 328 is in an open condition, the rate of flow, the pressure of flow, or both the pressure and rate of flow of preservative gas from the source 304 to the compressible bladder 314 can be limited, such as by a flow-limiting connector 325. By way of a non-limiting example, the flow-limiting connector 325 could limit the flow rate of preservative gas from the source 304 to the compressible bladder 314 to a predetermined flow rate. By way of an illustrative example, the flow rate can be limited to less than 1 liter per minute or any other flow rate. The flow-limiting connector 325 could, for example, include a narrow-diameter tube connector, such as a connector having an inner diameter of 0.02 mm or some other dimension reduced as compared to other conduit connections within the fluidic system. Under such embodiments, rapid changes in pressure within the compressible bladder 314 are prevented on opening of the valve system 328, and excessively rapid inflation of the compressible bladder 314 is prevented.

In operation of the disclosed automatic preservative gas replenishing system 300, the compressible bladder 314 will automatically be filled to the predetermined state of inflation by a supply of preservative gas from the source 304. When a liquid or other material within a vessel 200 is to be preserved, a fluid exchange structure 12 can be affixed thereto, such as by being pressed into the neck of the vessel 200. Wine can be used as a non-limiting example. The fluid exchange structure 12 can be induced into an open condition wherein the fluid pathways are open. Wine within the vessel 200 can be poured from the vessel 200 under the natural force of gravity. As the wine is poured from the vessel 200 through one fluidic pathway of the fluid exchange structure 12, preservative gas is drawn from the compressible bladder 314 through the distribution conduit 332 in volumetric displacement of the exhausted wine so that the inner volume of the vessel 200 previously occupied by the wine is now occupied by preservative gas. When the volume of gas within the compressible bladder 314 falls below the predetermined state of inflation, the inflation detection system 316 will detect the same and trigger the valve system 328 to an open condition. Limited-rate flow of preservative gas will then be permitted from the source 304 of preservative gas so that the compressible bladder 314 will be freshly supplied and filled with preservative gas until the predetermined state of inflation is reached. When the predetermined state of inflation is reached, the inflation detection system 316 will detect the same and trigger the valve system 328 to a closed condition to prevent the further supply of preservative gas to the bladder 314 from the source 304 until a further requirement is detected. The compressible bladder 314 is thus automatically supplied with preservative gas while excess pressurization of the preservative gas in the bladder 314 is automatically prevented.

Figure 45:
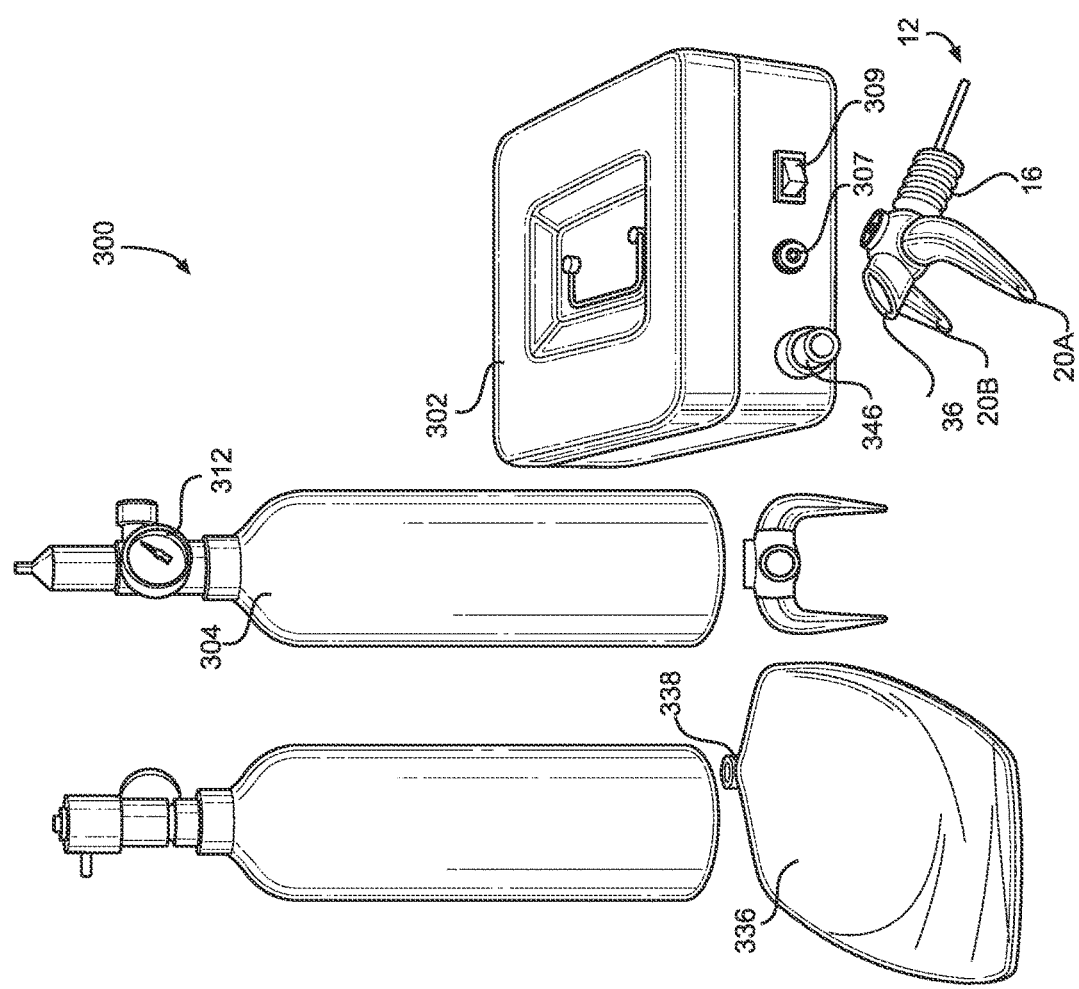
FIG. 45 is a further perspective view of the automatic preservative gas replenishing system of FIG. 43.

Looking further to FIG. 45, it would further be possible to use the automatic replenishing system 300 to replenish a separate compressible bladder 336 with a connection valve 338. So filled, preservative gas within the bladder 336 can then be used for conducting volumetric displacement preservation as taught herein.

Also according to the embodiments of the invention, the automatic preservative gas replenishing system 300 can be employed to practice a method of measuring the volume of liquid or other material displaced in volumetric displacement. For example, the system 300 can measure the flow of preservative gas, which provides an indication of the corresponding volume of liquid or other material displaced through volumetric displacement. By way of non-limiting example, a volumetric measuring flow meter 312 could be connected to the source 304 of preservative gas. Additionally or alternatively, one or more flow meters 313 could be retained within the housing 302 along the path of gaseous flow through the system 300. For instance, a flow meter 313 could be disposed to measure preservative gas passing through the valve system 328. A flow meter 317 could further or alternatively be disposed between the compressible bladder 314 and the distribution conduit 332. Still further, a flow meter could be incorporated into the fluid exchange structure 12.

In any event, by measuring the volume of preservative gas supplied to a vessel or vessels 200 by the system 300, one can determine the volume of wine or other material dispensed from the vessel or vessels 200. Indeed, through electronic memory and software operating on the electrical system 315 or in communication therewith, the system 300 can harvest, process, and analyze data from use of the system 300. The volume of liquid or other material dispensed from multiple separate individual vessels 200 can be measured and tracked. For example, by determining the volume of material dispensed from a given vessel 200 and obtaining the original volume of material within the vessel 200, one can further determine the volume of material remaining within the vessel 200. Other dispensing and usage characteristics can be measured, tracked, and exploited. One can, for instance, determine the volume of liquid dispensed from and remaining in one or more vessels simultaneously. One can track the time of dispensing operations and the time of opening of a given vessel 200. Inventory and product ordering can be controlled and improved, potentially through automatic reordering based on measured material that has been dispensed. Individual dispensing operations can be tracked and analyzed, including to control and verify portions dispensed. Planning and accounting can be facilitated, and cost and waste, such as through spoilage, can be minimized.

Vessels 200 can be individually identified, such as through a unique identifier 319, which can be numeric, electronic, coded, visual, one and two-dimensional bar codes, RFID chips, or any other unique identifier. Flow meters 312, 313, 317 or other tracking mechanisms having a temporary or permanent allocation to a specific vessel 200 can be tracked in computer memory within the electrical system 315 and/or external to the system 300, such as via software operating on an electronic computer. Data regarding material dispensed can be tracked and transmitted in certain practices of the invention, such as through electronic memory, wired communication, wireless communication, such as but not limited to Wifi or Bluetooth protocols, or any other form of data exploitation. Since measuring either the volume of preservative gas supplied or the volume of material dispensed can give permit determination of the exact volume of the other, a digitalized inventory can be maintained, such as through electronic wired and wireless devices, including the flow meters 312, 313, and 317. Data regarding individual vessels 200 can be obtained and exploited, and it could be maintained, controlled, and analyzed remotely, such as through the cloud. The liquid leaving an individual vessel can be determined, such as for marketing, commerce, accounting, and restocking inventory purposes. The system 300 could, for instance, obtain a unique identification of the vessel 200 to be tracked and can track its contents, the volume dispensed, and the time and date of opening and dispensing.

As used herein, references to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, for example, the term "or" should generally be understood to mean "and/or." Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," and the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics should be understood to contemplate a range of deviations that would be appreciated by one of ordinary skill in the art to operate satisfactorily for a corresponding use, function, or purpose. The use of any and all examples or exemplary language, as in "such as" or the like, provided herein, is intended merely to better illuminate the embodiments and does not pose a limitation on the scope of the embodiments. No language in the specification should be construed as indicating any unclaimed element as essential to the practice of the embodiments. In the description, it is understood that terms such as "first," "second," "top," "bottom," "upper," "lower," and the like are words of convenience and are not to be construed as limiting terms.

With certain details and embodiments of the present inventions for an automatic system for the conservation of gas and other substances, the system for preserving and dispensing wine and other perishable substances, and the automatic preservative gas replenishing system disclosed, it will be appreciated by one skilled in the art that numerous changes and additions could be made thereto without deviating from the spirit or scope of the invention. This is particularly true when one bears in mind that the presently preferred embodiments merely exemplify the broader invention revealed herein. Accordingly, it will be clear that those with major features of the invention in mind could craft embodiments that incorporate those major features while not incorporating all of the features included in the preferred embodiments.

Therefore, the following claims shall define the scope of protection to be afforded to the invention. Those claims shall be deemed to include equivalent constructions insofar as they do not depart from the spirit and scope of the invention. It must be further noted that a plurality of the following claims may express, or be interpreted to express, certain elements as means for performing a specific function, at times without the recital of structure or material. As the law demands, any such claims shall be construed to cover not only the corresponding structure and material expressly described in this specification but also all legally-cognizable equivalents thereof.

We claim as deserving the protection of Letters Patent:
1. A system for the conservation of oxygen supplied to a patient, the system comprising:
an expandable and compressible donor reservoir with an outer wall, an inner volume for retaining a volume of oxygen, and at least one orifice for allowing a passage of oxygen into and out of the inner volume, wherein the outer wall of the donor reservoir comprises a shell formed from a lightweight, flexible foil;
a supply conduit adapted to receive oxygen from a source of oxygen wherein the supply conduit has a first end for supplying oxygen to the donor reservoir and a second end for being fluidically connected to the source of oxygen;

an ambient pressure conduit adapted to supply oxygen along a fluid path from the donor reservoir to a recipient wherein the ambient pressure conduit has a first end in fluidic communication with the donor reservoir for receiving oxygen from the donor reservoir and a second end for being fluidically connected to the recipient;

an inflation detection system operable to detect a first condition wherein the donor reservoir is inflated with oxygen to a predetermined state of inflation and a second condition wherein the donor reservoir is below the predetermined state of inflation; and a valve system for being disposed between the source of oxygen and the donor reservoir wherein the valve system is operative when in a closed condition to prevent oxygen from flowing from the source of oxygen and into the donor reservoir when the donor reservoir is in the first condition, wherein the valve system is operative in an open condition to permit oxygen to flow from the source of oxygen and into the donor reservoir when the donor reservoir is in the second condition, and wherein the valve system and the inflation detection system are operative to maintain the volume of oxygen in the donor reservoir substantially at ambient pressure.

2. The system for the conservation of oxygen of claim 1, wherein the donor reservoir has a fully inflated condition, wherein the inflation detection system is operative to detect when the donor reservoir is inflated to within a predetermined range of the fully inflated condition, wherein the inflation detection system detects the first condition when the donor reservoir is inflated to within the predetermined range of the fully inflated condition, and wherein the inflation detection system detects the second condition when the donor reservoir is inflated below the predetermined range of the fully inflated condition.

3. The system for the conservation of oxygen of claim 1 further comprising a source of oxygen.

4. The system for the conservation of oxygen of claim 1, wherein the inflation detection system comprises an electro-mechanical system.

5. The system for the conservation of oxygen of claim 4, wherein the inflation detection system comprises a switch disposed to be moved by the outer wall of the donor reservoir when the donor reservoir is inflated with oxygen to the predetermined state of inflation.

6. The system for the conservation of oxygen of claim 5, wherein the switch is biased toward the donor reservoir.

7. The system for the conservation of oxygen of claim 5, wherein the switch has an activated state wherein the switch is disposed at or beyond an inward position with respect to the inner volume of the donor reservoir and a deactivated state when the switch is moved outwardly by the outer wall of the donor reservoir when the volume of oxygen in the donor reservoir reaches the predetermined state of inflation, wherein the valve system is operative to prevent oxygen from flowing from the source of oxygen and into the donor reservoir when the switch is in the deactivated state and wherein the valve system is operative to permit oxygen to flow from the source of oxygen and into the donor reservoir when the switch is in the activated state.

8. The system for the conservation of oxygen of claim 7, wherein the switch comprises a float switch.

9. The system for the conservation of oxygen of claim 8, wherein the float switch comprises a contact structure with a collar that is extendable and retractable relative to a central column and wherein the collar retains a magnet and wherein the central column retains electrical contacts that are brought into electrical contact by a proximity to the magnet when the switch is in the activated state.

10. The system for the conservation of oxygen of claim 1, wherein the valve system comprises a solenoid valve that is in electrical communication with the inflation detection system.

11. The system for the conservation of oxygen of claim 10, wherein the solenoid valve is induced by the inflation detection system to a closed condition to prevent the flow of oxygen from the source of oxygen to the donor reservoir when the donor reservoir is in the first condition and wherein the solenoid valve is induced by the inflation detection system to an open condition to permit the flow of oxygen from the source of oxygen to the donor reservoir when the donor reservoir is in the second condition.

12. The system for the conservation of oxygen of claim 1, further comprising a recipient delivery device coupled to the second end of the ambient pressure conduit.

13. The system for the conservation of oxygen of claim 12, wherein the recipient delivery device comprises a breathing mask.

14. The system for the conservation of oxygen of claim 1, wherein the donor reservoir is disposed within a housing.

15. The system for the conservation of oxygen of claim 14, wherein the inflation detection system comprises an electro-mechanical system with a switch supported by the housing and disposed to be moved by the outer wall of the donor reservoir when the donor reservoir is inflated with oxygen to the predetermined state of inflation.

16. The system for the conservation of oxygen of claim 14, wherein the housing is transparent whereby the state of inflation of the donor reservoir can be visually perceived.

17. The system for the conservation of oxygen of claim 1, further comprising a one-way inspiratory valve disposed along the fluid path from the donor reservoir to the recipient wherein the one-way inspiratory valve is operative to enable oxygen to flow from the donor reservoir, through the ambient pressure conduit, and to the recipient but to prevent reverse flow of oxygen.

18. The system for the conservation of oxygen of claim 1, wherein the inflation detection system comprises a contactless detection system.

19. The system for the conservation of oxygen of claim 18, wherein the inflation detection system comprises an optical detection system.

20. A system for providing a supply of gas, the system comprising:

an expandable and compressible reservoir with an outer wall, an inner volume for retaining a volume of gas, and at least one orifice for allowing a passage of gas into and out of the inner volume, wherein the outer wall of the reservoir comprises a shell formed from a lightweight, flexible foil;

a supply conduit adapted to receive gas from a source of gas wherein the supply conduit has a first end for supplying gas to the reservoir and a second end for being fluidically connected to the source of gas;

an ambient pressure conduit adapted to supply gas along a fluid path from the reservoir to a recipient wherein the ambient pressure conduit has a first end in fluidic communication with the reservoir for receiving gas from the reservoir and a second end for being fluidically connected to the recipient;

an inflation detection system operable to detect a first condition wherein the reservoir is inflated with gas to a predetermined state of inflation and a second condition wherein the reservoir is below the predetermined state of inflation; and a valve system for being disposed between the source of gas and the reservoir wherein the valve system is operative when in a closed condition to prevent gas from flowing from the source of gas and into the reservoir when the reservoir is in the first condition, and wherein the valve system is operative in an open condition to permit gas to flow from the source of gas and into the reservoir when the reservoir is in the second condition, and wherein the valve system and the inflation detection system are operative to maintain the volume of oxygen in the donor reservoir substantially at ambient pressure.

21. The system of claim 20, wherein the reservoir has a fully inflated condition, wherein the inflation detection system is operative to detect when the reservoir is inflated to within a predetermined range of the fully inflated condition, wherein the inflation detection system detects the first condition when the reservoir is inflated to within the predetermined range of the fully inflated condition, and wherein the inflation detection system detects the second condition when the reservoir is inflated below the predetermined range of the fully inflated condition.

22. The system of claim 20, wherein the inflation detection system comprises a switch disposed to be moved by the outer wall of the reservoir when the reservoir is inflated to the predetermined state of inflation.

23. The system of claim 22, wherein the switch has an activated state wherein the switch is disposed at or beyond an inward position with respect to the inner volume of the reservoir and a deactivated state when the switch is moved outwardly by the outer wall of the reservoir when the volume of gas in the reservoir reaches the predetermined state of inflation, wherein the valve system is operative to prevent gas from flowing from the source of gas and into the reservoir when the switch is in the deactivated state and wherein the valve system is operative to permit gas to flow from the source of gas and into the reservoir when the switch is in the activated state.

24. The system of claim 23, wherein the switch comprises a float switch.

25. The system of claim 20, wherein the inflation detection system comprises a contactless detection system.

26. The system of claim 25, wherein the inflation detection system comprises an optical detection system.

27. The system for the conservation of oxygen of claim 1, wherein the lightweight, flexible foil that forms the donor reservoir comprises a layer of polymeric material.

28. The system for the conservation of oxygen of claim 27, wherein the lightweight, flexible foil that forms the donor reservoir further comprises a lining.

29. The system for the conservation of oxygen of claim 28, wherein the lining comprises an aluminum lining.

30. The system for the conservation of oxygen of claim 1, further comprising a fluidic connector, wherein the fluidic connector has a first port in fluidic communication with the donor reservoir, a second port in fluidic communication with the ambient pressure conduit and, through the ambient pressure conduit, to the recipient, and a third port in fluidic communication with the supply conduit adapted to receive oxygen from the source of oxygen, wherein the first, second, and third ports are in fluidic communication with one another within the fluidic connector.

31. The system for the conservation of oxygen of claim 30, further comprising a one-way inspiratory valve fluidically connected to the second port of the fluidic connector whereby the one-way inspiratory valve is interposed between the donor reservoir and the recipient, wherein the one-way inspiratory valve is operative to enable oxygen to flow from the donor reservoir, through the ambient pressure conduit, and to the recipient but to prevent reverse oxygen flow from the recipient and into the donor reservoir.

32. The system of claim 31, wherein the reservoir is sealed but for an entry orifice in the reservoir and wherein the first port of the fluidic connector is in fluidic communication with the entry orifice in the reservoir.

33. The system of claim 32, wherein the third port is disposed between the first and second ports.

* * * * *